(12) United States Patent
Smurro

(10) Patent No.: US 11,961,624 B2
(45) Date of Patent: Apr. 16, 2024

(54) AUGMENTING CLINICAL INTELLIGENCE WITH FEDERATED LEARNING, IMAGING ANALYTICS AND OUTCOMES DECISION SUPPORT

(71) Applicant: James Paul Smurro, San Clemente, CA (US)

(72) Inventor: James Paul Smurro, San Clemente, CA (US)

( * ) Notice: Subject to any disclaimer, the term of this patent is extended or adjusted under 35 U.S.C. 154(b) by 133 days.

(21) Appl. No.: 17/353,791

(22) Filed: Jun. 21, 2021

(65) Prior Publication Data

US 2021/0313077 A1  Oct. 7, 2021

Related U.S. Application Data

(63) Continuation-in-part of application No. 16/450,974, filed on Jun. 24, 2019, now Pat. No. 11,043,307, which is a continuation-in-part of application No. 15/731,201, filed on May 2, 2017, now Pat. No. 10,332,639, which is a continuation-in-part of
(Continued)

(51) Int. Cl.
| | |
|---|---|
| *G16H 80/00* | (2018.01) |
| *G16H 10/60* | (2018.01) |
| *G16H 40/20* | (2018.01) |
| *G16H 50/20* | (2018.01) |
| *H04L 12/18* | (2006.01) |

(52) U.S. Cl.
CPC ............ *G16H 80/00* (2018.01); *G16H 10/60* (2018.01); *G16H 40/20* (2018.01); *G16H 50/20* (2018.01); *H04L 12/1822* (2013.01); *H04L 12/1827* (2013.01)

(58) Field of Classification Search
CPC ....................................................... G16H 80/00
See application file for complete search history.

(56) References Cited

U.S. PATENT DOCUMENTS

| | | | |
|---|---|---|---|
| 2003/0208477 A1* | 11/2003 | Smirniotopoulos | ... G16H 40/67 |
| 2017/0178320 A1* | 6/2017 | Saalbach | ............... G06T 7/0012 |

* cited by examiner

*Primary Examiner* — Olisa Anwah

(57) ABSTRACT

The invention integrates emerging applications, tools and techniques for machine learning in medicine with videoconference networking technology in novel business methods that support rapid adaptive learning for medical minds and machines. These methods can leverage domain knowledge and clinical expertise with networked cognitive collaboration, augmented clinical intelligence and cybernetic workflow streams for learning health care systems. The invention enables multimodal clinical communications, collaboration, consultation and instruction between and among heterogeneous networked teams of persons, machines, devices, neural networks, robots and algorithms. It provides for both synchronous and asynchronous cognitive collaboration with multichannel, multiplexed imagery data streams during various stages of medical disease and injury management—detection, diagnosis, prognosis, treatment, measurement, monitoring and reporting, as well as workflow optimization with operational analytics for outcomes, performance, results, resource utilization, resource consumption and costs. The invention enables cognitively-enriched, annotation and tagging, as well as encapsulation, saving and sharing of collaborated imagery data streams as packetized clinical intelligence.

21 Claims, 85 Drawing Sheets

Related U.S. Application Data application No. 14/544,807, filed on Feb. 18, 2015, now Pat. No. 9,641,799, which is a continuation-in-part of application No. 13/999,688, filed on Mar. 15, 2014, now abandoned.

(60) Provisional application No. 61/967,323, filed on Mar. 15, 2014, provisional application No. 61/852,625, filed on Mar. 15, 2013.

FIG. 9

Alternative Network Architectures for TIMS Clini-Pod Deployment:
Point-to-Point vs Hub-and-Spoke vs Chord

Semantic Metadata Registry (MDR)

▶ Metadata for Semantic Interoperability

- annotate the information models of different systems
  - with the same set of *data elements* residing in the *metadata registries*
- early approach: bottom-up
- takes root from several other disciplines like linguistics, compilers etc...

FIG. 29

Semantic Trails can be built over a Web of Semantic (Meta)Data extracted (manually, semi-automatically and automatically) and gleaned from

- Structured data (e.g., NCBI databases)
- Semi-structured data (e.g., XML based and semantic metadata standards for domain specific data representations and exchanges)
- Unstructured data (e.g., Pubmed and other biomedical literature) and
- Various modalities (experimental data, medical images, etc.)

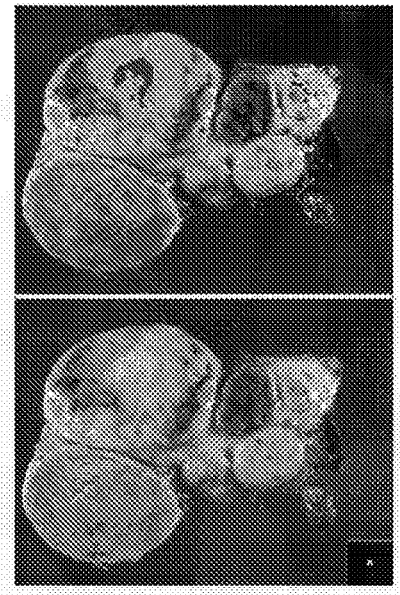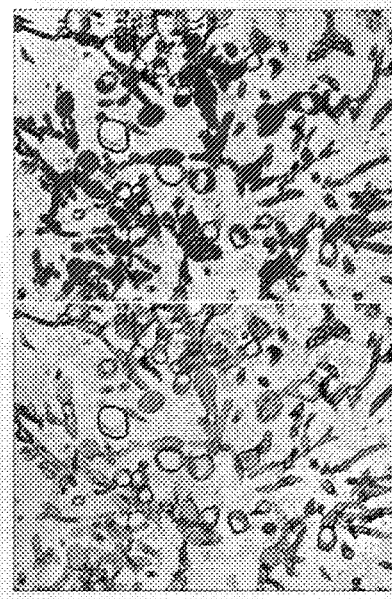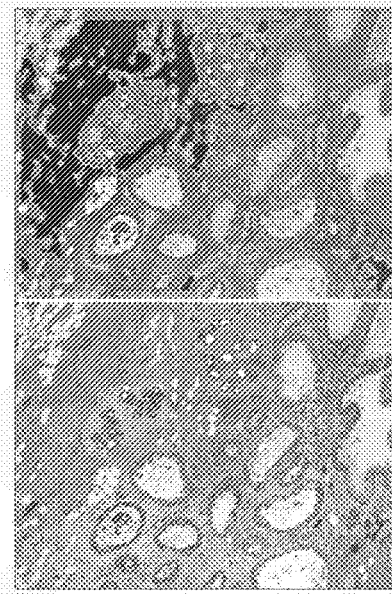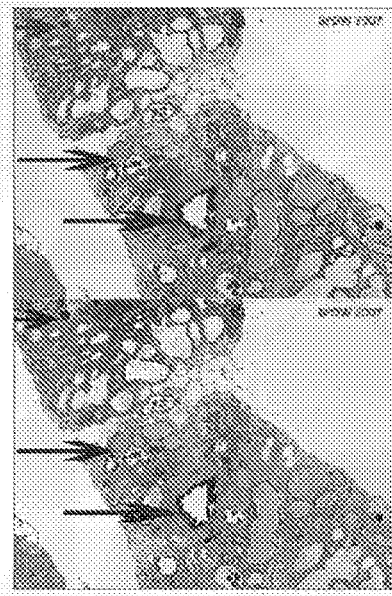
FIG. 42

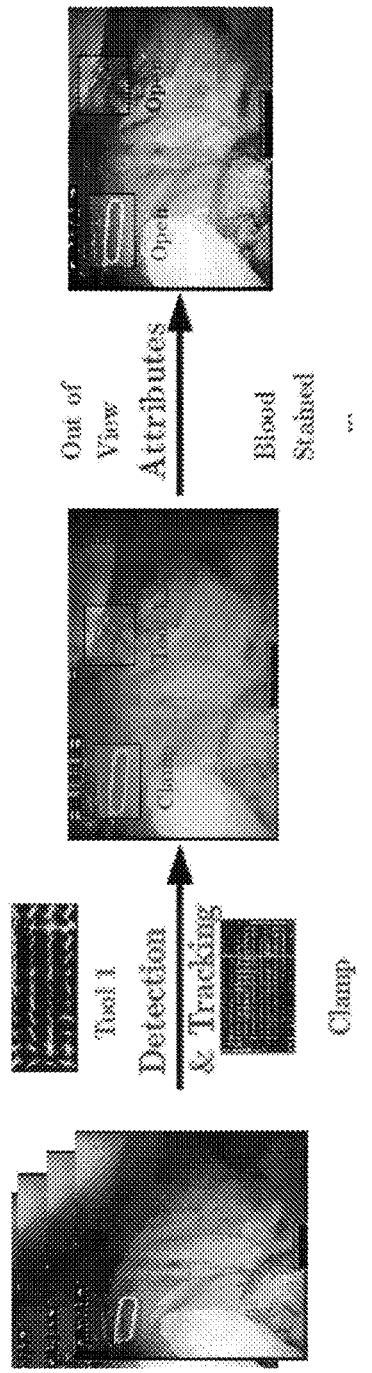
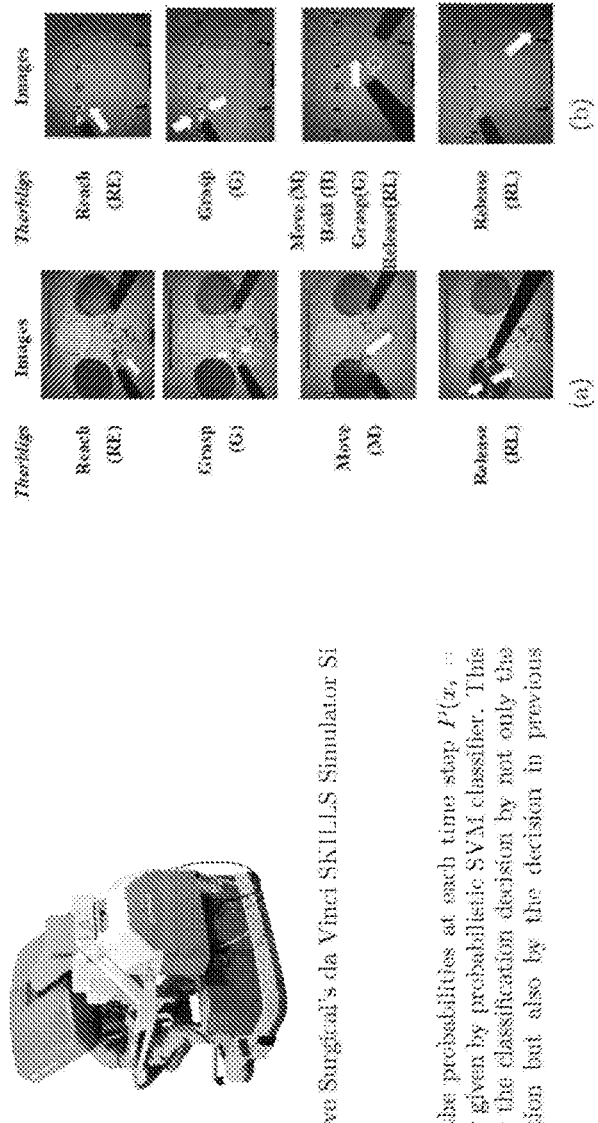
FIG. 58

Complex procedures don't need to be described, but can in fact be demonstrated.

Highlights:

- Realistic MIS instruments to demonstrate complex surgical procedures.
- The ability to cut, retract and suture a *live video feed*.

AUGMENTING CLINICAL INTELLIGENCE WITH FEDERATED LEARNING, IMAGING ANALYTICS AND OUTCOMES DECISION SUPPORT

FIELD

The invention generally relates to a network system and methods for receiving and transmitting streaming imagery data, including medical images, waveforms, audio and haptic signals, biomedical and clinical documents, both live and asynchronously, and allowing operators to concurrently curate, annotate, tag, encapsulate and save that imagery data, together with those annotations and searchable metadata tags in single file format structures. The invention acquires streaming imagery data through network-connected imagery-enabled devices, and allows a variety of cognitive collaborants, singly or together, to concurrently communicate, collaborate, consult and instruct, generally by curating, annotating and tagging, telestrating, sketching image overlays on streaming imagery data, and saving those images together with collaborated annotations and metadata, as streaming augmented intelligence for rapid adaptive learning, specialist skills acquisition and informatics-enriched innovation with multimodal clinical instruction and value chain knowledge exchange.

IMPROVEMENT OVER PRIOR ART

As used herein, "cognitive collaborant" refers to one or more cognitive collaborators, human or non-human, including persons, machines, devices, neural networks, robots and algorithms, as well as heterogeneous networked teams of persons, machines, devices, neural networks, robots and algorithms.

The invention enables multichannel multiplexed communications, collaboration, consultation and instruction with streaming imagery data by cognitive collaborants, including heterogeneous networked teams of persons, machines, devices, neural networks, robots and algorithms. The invention enables both synchronous and asynchronous multimodal clinical communications, collaboration, consultation and instruction during various stages of medical disease and injury management, including detection, diagnosis, prognosis, treatment, measurement, monitoring and reporting, as well as workflow optimization with operational analytics for outcomes, performance, results, resource utilization, resource consumption and costs.

The invention enables pluribus network encoding with multichannel multiplexed steaming imagery data from signals, sensors and devices, including packets, waveforms and streams, along with space shifting, time shifting and format shifting media synchronization. The invention enables heterogeneous networked teams of cognitive collaborants to recursively curate, annotate and tag, encapsulate, save and share multichannel multiplexed imagery data streams, including multisensory data stream visualizations, and bi-directional value chain knowledge exchange, with streaming imagery data from heterogeneous spatial and temporal sources, locations, modalities and scales. The invention can acquire both live stream and archived medical imagery data from network-connected medical devices, cameras, signals and sensors. The network system can also acquire multiomic data—phenotypic, genomic and metabolomic, as well as pathomic, radiomic, radiopathomic and radiogenomic—from structured reports and clinical documents, as well as biometric maps, movies, data stream visualizations, haptic maps and heat maps. The network system can also acquire packetized clinical informatics from imagery data repositories, from clinical workstations and mobile medical devices, as well as from wearable computing devices, signals and sensors.

The invention enables networked teams to interactively communicate, concurrently collaborate and bi-directionally exchange multichannel multiplexed imagery data streams, singly or together, in real time or asynchronously, generally by curating, annotating and tagging imagery information objects. The invention encapsulates and saves collaborated imagery data streams, together with collaborated clinical annotations, imaging metadata, as well as semantic metadata and annotations, and privacy protected metadata identifying personal health information [PHI], in standard known file formats as clinical cognitive vismemes—encapsulated packets, waveforms and streams. Clinical cognitive vismemes preserve packetized imagery information objects, clinical annotations and metadata tags in native file format structures, including PDF, MPEG, JPEG, XML, XMPP, TIFF, RDF, RDF/XML, QR, SVG and DAE, as well as DICOM. When clinical cognitive vismemes are encapsulated and saved in formats compliant with standards for digital communications in medicine [DICOM], they can also be referred to as medical dicom vismemes.

Clinical cognitive vismemes allow for recursive cognitive enrichment through recursive curation, annotation, tagging, encapsulation and saving, together with value chain knowledge exchange. Value chain knowledge exchange includes knowledge creation and acquisition, knowledge visualization and sharing, knowledge replication and integration, knowledge protection and destruction, as well as outcomes performance evaluation and learning, all of which can accelerate outcomes-driven innovation.

The invention also enables informatics-enriched innovation and value chain knowledge exchange with multimodal clinical communications and multisensory data stream visualization. Multimodal clinical communications, collaboration, consultation and instruction includes multisensory [sight-sound-touch] digital data exchange with vision, audition and sensation, including semiotics, semantics and somesthetics [haptics].

The invention enables live stream multicasting of N-way multi-party collaborations, including multisensory data stream visualization and bi-directional knowledge exchange, with multichannel multiplexed imagery data streams, and concurrent transmission of secure, encrypted clinical cognitive vismemes across collaborative file sharing data networks for informatics-enriched learning, specialist skills acquisition and accelerated knowledge exchange. Principal areas of clinical application include cognitively-enriched enterprise imaging with streaming imagery informatics, collaborative precision medicine with multiomic data analytics, informatics-enriched imagery guided intervention, including robotic-assisted surgery, along with newly-emerging disciplines for machine learning with medical imaging, including deep learning, transfer learning, reinforcement learning, convolutional neural networks, recurrent neural networks, long short term memory networks and natural language processing, along with emerging techniques for precision guided biomedical nanorobotics and precision targeted theranostic nanomedicine.

The novelty of the present invention enables multiparty networked clinical communications, collaboration, consultation and instruction with streaming imagery data by integrating videoconferencing systems technology with emerging applications and techniques for machine learning in medicine.

In addition to these the present invention supports several additional improvements over prior art, which are briefly described below:

1. Federated Learning (FL) is a Machine Learning Setting where Many Clients Collaboratively Train a Model Under the Orchestration of a Central Server, while Keeping the Training Data Decentralized.

"Federated learning is a machine learning setting where multiple entities (clients) collaborate in solving a machine learning problem, under the coordination of a central server or service provider. Each client's raw data is stored locally and not exchanged or transferred; instead, focused updates intended for immediate aggregation are used to achieve the learning objective."

Cross-silo applications for electronic health records mining and medical data segmentation Cross-Silo Federated Learning, Fully Decentralized/Peer-to-Peer Distributed Learning and Federated transfer learning Federated learning with edge computing, which affords greater data security, where its data is separately stored and processed in the edge node, as well as containerization, that provides management of all the various execution environments that devices in the edge federated learning setting will utilize.

The combination of edge computing and federated learning, along with more collaborative training methods for edge federated learning, can provides for better user experience and privacy protection.

2. Integration with Imaging Analytics for Preparing Medical Imaging Data for Machine Learning Image analysis is one of the most promising applications of artificial intelligence (AI) in health care, potentially improving prediction, diagnosis, and treatment of diseases. Federated artificial intelligence (AI)-based medical image analysis for the application of AI to large-scale clinical imaging data with decentralized local execution of data analyses can solve many obstacles of cross-site collaboration.

Supervised artificial intelligence (AI) methods for evaluation of medical images require a curation process for data to optimally train, validate, and test algorithms. The chief obstacles to development and clinical implementation of AI algorithms include availability of sufficiently large, curated, and representative training data that includes expert labeling (eg, annotations).

New approaches such as federated learning, interactive reporting, and synoptic reporting may help to address data availability in the future; however, curating and annotating data, as well as computational requirements, are substantial barriers.

Advanced imaging analytics and the extraction of high-dimensional data from medical images, called radiomics, is emerging as the other side of the personalization coin. By adding an individual patients' tumor phenotypic (structural) information coupled with the patients' genetic data, drug developers can create more precise therapies.

By using artificial intelligence (AI) to discern and compute data from medical images, radiomics enables drug developers to profile a patient, tumor, and therapy across multiple dimensions to find patterns and similarities that would otherwise be unobtainable.

3. Support for Interactive ("Visually Embedded") Annotations, as Well as Semantically Meaningful Segmentation, Parametric Maps and Structured Reports Traditionally, different annotation mechanisms have been provided in DICOM for the purpose of encoding, transporting and querying for clinically generated and machine generated image-related results. Some of these are purely focused on consistent rendering and appearance, and require visual human interpretation, while others are structured, coded and semantically meaningful, but require more work on the authoring side.

Modern AI workflow scenarios require more complex semantically meaningful payloads and interactions with the users, for training and testing, as well as for clinical operation. To the extent that DICOM payloads and protocols can be reused for both types of scenario, the existing standard should be leveraged to implement new AI applications and existing templates and code sets.

The workflow has traditionally focused on human creation and display rather than automated analysis and consumption. Identify the workflow of annotation creation and use in Al using DICOM protocols and payloads.

Diagnostic and evidential static image, video clip, and sound multimedia are captured during routine clinical care in cardiology, dermatology, ophthalmology, pathology, physiatry, radiation oncology, radiology, endoscopic procedural specialties, and other medical disciplines.

4. Interactive Multimedia Report (IMR) Creation and Ingestion into Electronic Health Records.

One consensus definition of IMR is

"interactive medical documentation that combines clinical images, videos, sound, imaging metadata, and/or image annotations with text, typographic emphases, tables, graphs, event timelines, anatomic maps, hyperlinks, and/or educational resources to optimize communication between medical professionals, and between medical professionals and their patients."

Providers typically describe the multimedia findings in contemporaneous electronic health record clinical notes or associate a textual interpretative report. Visual communication aids commonly used to connect, synthesize, and supplement multimedia and descriptive text outside medicine remain technically challenging to integrate into patient care.

Such beneficial interactive elements may include hyperlinks between text, multimedia elements, alphanumeric and geometric annotations, tables, graphs, timelines, diagrams, anatomic maps, and hyperlinks to external educational references that patients or provider consumers may find valuable.

5. Support for IHE Radiology Newly Emerging Supports for AI Interoperability in Imaging

BACKGROUND

Machine Learning in Medicine

Digital clinical data, captured and stored on electronic medical records by hospitals and clinics, along with ever growing volumes of medical imaging data, have sparked growing interest and applications of machine learning in medicine.

In recent years there has been a proliferation of artificial intelligence (AI) tools and resources available in medicine, especially with ever increasing computing power and a growing acceptance of cloud computing by hospitals and clinicians. Imaging analysis and clinical decision support are two particularly popular applications of machine learning in medicine, with tools that support diagnosis, treatment, care coordination and remote monitoring.

There is much promise in the utilization of AI methodologies such as machine learning and deep learning for augmented biomedical image interpretation in radiology, cardiology, pathology, dermatology, ophthalmology and genomic medicine.

One example of machine learning for medical imaging involves differential diagnosis of breast cancer enabled by joint analysis of functional genomic information and pathology images (pathogenomics) within a biomedical imaging informatics framework consisting of image extraction, feature combination, and classification.

Algorithms based on deep convolutional neural networks have been used to detect diabetic retinopathy in retinal fundus photographs with high specificity and sensitivity, as good as with board-certified ophthalmologists in making diagnoses.

Personalized precision medicine with all its complexity and enormity of data to be analyzed is particularly well suited for the portfolio of AI methodologies, including deep learning, which can be used to identify and assess patients with similar genotype-phenotype characteristics. In genomic diagnostics, clinicians are often frustrated by the tedious nature of searching for genotype-phenotype interrelationships among syndromes, especially for extremely rare diseases. Now, geneticists may be able to use visual diagnostic decision support systems that employ machine learning algorithms and digital imaging processing techniques in a hybrid approach for automated detection and diagnosis in medical genetics.

An essential part of the precision medicine paradigm is individualized therapy based on genotype-phenotype coupling and pharmacogenomic profiles. There are many potential applications of deep learning for large datasets in pharmaceutical research, such as physicochemical property prediction, formulation prediction, and properties such as absorption, distribution, metabolism, excretion, toxicity, and even target prediction.

Surgical robotics have advanced to include 3D visualization and informatics-enriched imagery guided interventions.

Machine learning algorithms can also be applied to large-scale wearable sensor data in neurological disorders such as Parkinson's disease to significantly improve clinical diagnosis and management. Sensor-based, quantitative and objective systems for assessing Parkinson's disease have the potential to replace traditional qualitative and subjective ratings by human interpretation.

An essential part of digital medicine and wearable devices is the data mining of the incoming data for anomaly detection, prediction, diagnosis and clinical decision making. Data mining processes for data streams from wearable devices typically include feature extraction/selection processes to improve detection, prediction, and decision making by clinicians.

Machine learning techniques include supervised methodologies such as neural networks, support vector machines, naïve Bayesian classifiers, and hidden Markov models, as well as semi-supervised methods that can be used with less labeled data. These techniques can be applied to molecular imaging modalities with promising application for clinical diagnosis.

Four types of machine learning—deep learning, reinforcement learning, transfer learning and one-shot learning—may figure prominently in future applications of AI in medicine.

Deep learning with all its myriad capabilities may well be used for many applications in medical data analytics. The multiple layers of neural nets can be assigned to the many phenotypic as well as genomic expressions of conditions such as clinical measurements, biomarkers, imaging data, genomic information and disease subtypes.

Reinforcement learning is ideally designed for the many decision making aspects of medicine since it readily accommodates recognition of complex patterns, long-term planning, and many decision-making processes in clinical practice.

Transfer learning occurs when a network that is trained for one task is then used to configure the network for another task.

One-shot learning can bring a special dimension to unique cases in medicine as it does not require the usual large dimensionality of data that the other types of machine learning techniques typically require.

Natural language processing [NLP] includes machine learning techniques for speech recognition and identification, as well as language understanding and generation. Medical NLP may become increasingly useful for collaborative curation, annotation and tagging of medical imagery data by heterogeneous teams of medical minds and machines. Curated medical images, annotated and tagged as medical "ground truth", will become increasingly important not only for clinical detection, diagnosis and decision support, but also for the training, testing and validation at scale of machine learning algorithms requiring voluminous imagery data sets. Recurrent Neural Networks [RNN] and Long Short Term Memory [LSTM] networks have been successfully applied to a variety of problems in speech recognition, language modeling and translation, image captioning and image annotation.

Personalized precision medicine may require disruptive computational platforms for new biomedical knowledge discovery, and scalable computational frameworks that can leverage hypergraph-based data models and query languages that may be well-suited for representing complex multi-lateral, multi-scalar, and multi-dimensional relationships. Hypergraph-like stores of clinical information (e.g., from disease registries) can be combined with an individual patient's genomic and other phenotypic information (such as imaging data) to create more precise and personalized genome-based knowledge stores for clinical translation and discovery. Patients of very similar genomic and clinical elements could then be better discovered and matched for diagnostic and therapeutic strategies.

Cloud computing and storage can facilitate a full range of AI techniques for multi-institutional collaborations that may become essential to driving future applications of AI in biomedicine and healthcare. The internet of medical things (IoMT) may also provide the critical data sources for medicine in the form of wearable and monitoring devices from both hospital and home.

Clinical data analytics will increasingly rely on machine learning tools and techniques to answer many clinical questions for intelligence-based medicine, rather than current best practices of principally relying upon published medical reports for evidence-based medicine.

There is a compelling need for informatics-enriched innovation with AI-powered technologies that can improve diagnostics and therapeutics, and help deliver value-based care. The convergence of "big data" stores, improved AI algorithms, increasing use of graphical processing computational power (GPU), and cloud storage has begun to produce some intriguing machine learning projects with promising results for biomedicine and healthcare. Perhaps more importantly, continuing advances with AI-powered tools and techniques in healthcare will require efforts to ensure more collaborative teamwork and better sharing of curated datasets among the various stakeholders.

Productive AI strategies may involve synergistic collaborations of humans and machines—clinicians and data scientists, empowered with AI—so that machine learning in medicine may become a key enabler of new clinical knowledge and augmented clinical intelligence for learning health care systems.

Collaborative Clinical Workflows with Enterprise Imaging

The HIMSS-SIIM Collaborative Workgroup has defined Enterprise Imaging as:

"The management of all clinically relevant content, including imaging and multimedia, for the purposes of enhancing the electronic health record through a set of strategies and initiatives designed and implemented across the healthcare enterprise. These strategies and initiatives are based on departmental and specialty workflows for all clinical imaging content, and include methods for capture, indexing, management, storage, access for retrieval, viewing, exchange and analytics."

Enterprise imaging (EI) platforms typically provide the infrastructure, modalities, devices, and integration points, as well as a standards-based repository for storage of both DICOM and non-DICOM clinical images and video. Those centralized image repositories—e.g., a vendor neutral archive or an enterprise wide PACS system—typically include indices of both image and metadata-information contents held in the archive.

Medical imaging archives are increasingly becoming modality agnostic, modality vendor agnostic, specialty and service line agnostic, and viewer agnostic. Standards-based interfaces and communications, including DICOM, HL7, and standards-based Web Services, connect, enable, and support image acquisition workflows across modalities and departments. Image acquisition devices that support these standards may store their images, with meta-information, into the VNA. Acquisition devices that are supported include departmental DICOM imaging modalities, point-of-care acquisition modalities, handheld device photo or video apps, digital capture systems in procedure rooms, image exchange gateways, and software designed to import content saved on a disk or received by referring or patient portals.

Clinical content and multimedia content span four broad categories of medical workflows within Enterprise Imaging: diagnostic imaging, procedural imaging, evidence imaging, and image-based clinical reports.

Medical workflows across many departments capture and create a variety of types of "multimedia" information that is important to preserve, correlate with the images, and make accessible via the patient medical record. Multimedia content includes waveforms, audio or video clips, as well as other forms of graphical content that summarize imaging results with the results from other medical procedures and tests. Non-radiological examples can be found in many specialties including Cardiology, Neurology, Gastroenterology, Ophthalmology and Obstetrics. Graphical "report-style" results from various medical departments are increasingly being created and saved as PDF objects. These can include embedded images that show key findings, graphical diagrams that show the area of interest, or other measurement or test result information that correlates with the images.

Other examples of related multimedia content include time-based waveforms such as those produced by ECG or EEG devices. These may be treated as documents or image-like objects. Waveforms may be recorded and stored in a raw or processed form that requires an application to display them, or in some human-readable rendered form (like a PDF or screenshot). Like images, waveforms too can be classified as both evidence and diagnostic. Waveforms are the graphical representation of discrete data points but may be used as the sole basis of interpretation when other tools for analysis of discrete data points are not available or routinely incorporated within the interpretation protocol.

Most types of multimedia content, including waveforms, PDF reports, MPEG video clips, and JPEG photos, can be DICOM wrapped and stored as DICOM objects or they can be treated as a native document type (e.g., PDF, JPEG, MPEG, etc.) and saved in systems that can manage them as native objects. An important consideration is how this information will be managed, correlated, accessed, and viewed by physicians and patients. Wherever possible, related patient images and multimedia content could be made readily discoverable and shown together in a useful, natural way.

DICOM provides support for encoding both generic identification and modality and specialty-specific acquisition context for all enterprise imaging modalities. DICOM-like metadata can also be added to other image file formats like JPEG or TIFF. Other alternatives include encapsulating the image in a different standard format, such as HL7 Clinical Document Architecture (CDA), as is defined by the IRE Scanned Document (XDS-SD) profile, so that metadata remains directly associated with their related medical images. The invention described herein supports both approaches to encapsulating and saving medical metadata together with their associated medical imagery.

Video Collaboration with Medical Imaging

This invention relates to a videoconferencing system for 'live', i.e., real time, near real time or minimally latent, viewing of streaming medical imagery, and more particularly, to a network system and methods of using said videoconferencing system with both medical and non-medical imagery, and multiple input operators (participant "cognitive collaborants"), each viewing the other's inputs collaboratively and concurrently.

In the past, video conferencing systems could be summarized as enabling a plurality of users systems connected to each other, each being adapted to display a work area on a display screen or connected through a computer network. Collaboration of work is done on each system by use of a management table for registered node identification codes given for each system user. That is, every computer system, or one system, requires storage of collaboration user identifier in at least one of the user's computer system. The novelty of the current invention—a system and methods of multimodal clinical communications, collaboration, consultation and instruction for use with medical imagery—has improved upon prior art by allowing modular and scalable network clusters of gateway streamer servers that enable dynamic control allowing for faster and more efficient performance, as well as enabling multiparty cognitive collaboration with medical imagery in a Digital Imaging and Communications in Medicine environment, hereinafter referred to as DICOM.

The DICOM Standard pertains to the field of medical imaging informatics. The DICOM Standard is well known in the arts and facilitates interoperability of medical imaging equipment by specifying a set of protocols to be followed by devices claiming conformance to the standard. The DICOM Standard outlines syntax and semantic of commands and associated information which can be exchanged using these protocols. For media communication, it provides a set of media storage services to be followed by devices claiming conformance to the DICOM Standard, as well as a file format and medical dictionary structure to facilitate access to the images and related information stored on interchange media. DICOM data file format is data formatted in groups of information, known as Data Sets. The DICOM Standard provides a means to encapsulate in a single file format structure the Data Set related to a DICOM information object. The DICOM Standard requires a single file format structure, as the DICOM Standard specifies that each DICOM file contain both File Meta Information and a properly formatted Data Set (as specified in DICOM Standard 3.10). The DICOM Standard further specifies that the byte stream of the DICOM Data Set be placed into the file after the DICOM File Meta Information (as specified in PS 3.10 DICOM Part10: Media Storage and File format for Media Interchange).

The DICOM Standard specifies the rules for encapsulating DICOM Data Sets in the requisite DICOM File format. The DICOM Standard requires that a file meta information header be present in every DICOM file, and that the file meta information includes identifying information of the Data Set (PS 3.7-1). The DICOM Standard requires that the Data Set conform to the service-object pair (SOP) Class specified in the file meta information. "The DICOM File format provides a means to encapsulate a File the Data Set representing a SOP Instance relating to a DICOM Information Object." The DICOM Standard provides for the encapsulation of waveform data (PS 3.5 Part 5: Data Structures and Encoding), and for the encapsulation of structured reports (Supplement 114: DICOM Encapsulation of Clinical Document Architecture Documents) within imagery bit streams to facilitate the interchange of information between digital imaging computer systems in medical environments.

The DICOM File Meta Information includes identifying information on the encapsulated DICOM Data Set. The DICOM Standard requires that a file header of identifying information be present in every DICOM file. The DICOM file header consisting of a 128 byte File preamble, followed by a 4 byte DICOM prefix, followed by the File Meta Elements. This means, for example, that a DICOM file of a chest x-ray image actually contains the patient identification within the file, so that the image can never be separated from patient information by mistake. A DICOM file contains both the image and a large amount of patient information about whom, where, and how the image was acquired, known in the arts as patient metadata.

However, DICOM files often contain little information about the content of the imagery or meaning of the imagery pixels, the encapsulated waveform data used for audio clinical notes, or the encapsulated structured reports used for clinical documents, all of which are used for clinical detection, diagnosis and treatment of disease. This network system improves upon and applies in a collaborative environment which provides for capture, retrieval and concurrent viewing of both live and archived medical imagery streams for communication, collaboration and consultation with one or more sources of streaming imagery data by one or more users, also known as participant cognitive collaborants. Collaborated medical imagery streams comprise one or more sources of streaming imagery data, including DICOM imagery files. As used herein, DICOM imagery files include modality information objects, (e.g. streaming video), waveform information objects (e.g. voice audio, echocardiogram), and structured report document information objects (e.g. clinical documents), as specified in PS 3.3 Part 3: Information Object Definitions of the DICOM Standard.

Medical imagery streams include DICOM imagery files. This network system allows for each user to collaborate simultaneously with all users viewing every other users' work product, as the work product is being created, all coincident with one or more streams of streaming imagery data wherein each server manages streams of medical imagery together with participant cognitive collaborant input illustrations for use with DICOM imagery files. The network system provides live video and audio communication, as well as a method of viewing, recording and transmitting streaming imagery data, which include DICOM imagery files, in DICOM format, which requires a single file format structure. Streaming imagery data includes both live and archived imagery data. As used herein, multi-channel streaming imagery data is defined as a collection of one or more sources of streaming imagery data each of which comprise at least one image frame that defines a time progression of output from various sources, which include video, encapsulated waveform data, and encapsulated structured reports.

The network system provides multi-channel multiplexed capability for capture, retrieval and concurrent viewing of both live and archived medical imagery streams for communications, collaboration, consultation and instruction with one or more sources of streaming imagery data by participant cognitive collaborants. Participant cognitive collaborant input illustrations as defined herein include, but are not limited to telestrations, drawings, sketches, text annotations, including letter character text and numeric character text, image annotations, wave form annotations, voice annotations, video annotations, augmented reality imagery annotations, 3D/4D imagery annotations, outcomes annotations, costs annotations, resource consumption/utilization annotations, haptic annotations, patient metadata, imagery metadata, semantic metadata and annotations, appended patient metadata, appended imagery metadata and appended semantic metadata and annotations. The network system appends participant cognitive collaborant input illustrations to streaming imagery data, and encapsulates and saves those input illustrations, together with streaming imagery data, and relevant imagery metadata and semantic metadata and annotations, including appended imagery metadata and appended semantic metadata and annotations, from the collaboration session in single file format structures, known as collaborated imagery files. The 'single file encapsulate and save' functionality of the network system encapsulates and saves collaborated imagery files in single file format structures, as may be required or allowed by standards for clinical documentation or medical records storage, including those as specified in the DICOM Standard (e.g. as DICOM files).

The network system appends metadata tags to participant cognitive collaborant input illustrations and encapsulates and saves those tagged input illustrations together with the Data Set from the streaming imagery data and relevant metadata information from the metadata header in single file format structures for use within a DICOM imagery environment, including those as specified in the DICOM Standard. The network system appends metadata tags to alphanumeric text annotations, image annotations, wave form annotations, voice annotations, video annotations, augmented reality imagery annotations, 3D/4D imagery annotations, outcomes annotations, costs annotations, resource consumption/utilization annotations, haptic annotations and clinical documents and encapsulates those alpha-numeric text annotations, image annotations, wave form annotations, voice annotations, video annotations, augmented reality imagery annotations, 3D/4D imagery annotations, outcomes annotations, costs annotations, resource consumption/utilization annotations, haptic annotations and clinical documents and saves those as DICOM files. The network system can also append annotation files encapsulated as DICOM files to the Data Set for streaming imagery data, and encapsulate them together with relevant metadata information from the metadata header for streaming imagery data, and save in single file format structures as collaborated imagery files (CIF).

Collaborated imagery files, also known as CIFs, conform to the DICOM Standard and can be stored, archived, queried, and retrieved as DICOM files. CIFs can be stored locally in media libraries and later retrieved for subsequent use in collaboration sessions. CIFs conform to the DICOM Standard [3.10] and can be encrypted and/or transmitted over networks for remote viewing, communication and collaboration. CIFs conform to specifications of the DICOM Standard for secure encapsulation of DICOM objects in a clinical document architecture (CDA). As such CIFs can be stored as in archives conforming to health level seven (HL7), integrating the healthcare enterprise (IHE), cross-enterprise document sharing (XDS), cross-enterprise document sharing for imaging (XDS-I), Extensible Markup Language (XML), in Tagged Image file format (TIFF), as well as in RDF triples and RDF/XML for metadata model specification.

CIF's can also contain encapsulated and saved haptic imagery and annotations in COLLADA-compliant dae files. COLLADA (collaborative design activity) is an interchange file format for interactive 3D applications that has been adopted by ISO as a publicly available specification, ISO/PAS 17506. COLLADA defines an open standard XML schema for exchanging digital assets among various graphics software applications that might otherwise store their assets in incompatible file formats. COLLADA documents that describe digital assets are XML files, usually identified with a .dae (digital asset exchange) filename extension.

CIFs conform to specifications of the DICOM Standard for encapsulation of audio with imagery data sets. CIFs conform to specifications to the DICOM Standard for DICOM structured reporting. CIFs can be viewed as stand-alone medical imagery, or embedded into other CIFs as video, audio and haptic annotations. The network system can create collaborated imagery studies, also known as CIS's, which include one or more collaborated imagery files, encapsulated and saved in single file format structures, as may be required or allowed by standards for clinical documentation or medical records storage, including those as specified in the DICOM Standard format. Collaborated Imagery Studies, also known as 'Clini-DOCx' are visual story boards can be used for capture, display, file exchange, publication and distribution of collections of clinical cognitive vismemes.

The DICOM Standard defines the characteristics of a medical study performed on a patient as, "a collection of one or more series of medical images, presentation states, SR documents, overlays and/or curves that are logically related for the purpose of diagnosing a patient. Each study is associated with exactly one patient" (PS 3.3 A.1.2.2 STUDY IE). Streaming imagery data can include both collaborated imagery files and collaborated imagery studies. Both CIFs and Clini-DOCx can be incorporated into medical image streams of live or archived streaming imagery data for use during synchronous or asynchronous collaboration sessions.

The traditional way of capturing an image from a medical imaging device commonly called a modality, generally consisted of an operator or technician first conducting a scan. Then, using the modality to save the image, in still or motion video format, into the modality memory or into a main image storage database. The next step in the process typically involved downloading the image into a hospital database, known in the arts as a Picture Archiving and Communications System, hereinafter referred to as PACS or PACS server. PACS is a medical imaging technology which provides economical storage of, and convenient access to, images from multiple modalities (source machine types). Electronic images, including patient information known in the arts as patient metadata, are transmitted digitally to and from PACS, eliminating the need to manually file, retrieve or transport film jackets. The universal form of PACS image file storage and transfer is the DICOM Standard, and is well known in the arts. PACS can be further defined by a storage and management system for medical images.

In the medical field, images such as x-rays, MRI's and CAT scans typically require a greater amount of storage than other images in other industries. A clinician would access the PACS system to retrieve the image, view and review the image, and conceivably develop a diagnosis based on the information from the image. This system imagery is viewed by a user and diagnosis made without image delay and the user accomplishes all these tasks live. "Live" referring to events simulated by a computer at the same speed that they would normally occur in real life. In graphics animation, for example, a live program (such as this inventor's system) would display objects moving across the display at the same time they would actually move, or in the case of this invention, a cognitive collaborant views the image live and collaborates from cognitive collaborant to cognitive collaborant with no perceivable delay to any of them.

The inventor has developed a novel and simple network system and methods of using the same, to allow a group of cognitive collaborants to concurrently collaborate on a computer system, with each participant cognitive collaborant viewing each other's telestrations, drawings, and annotations and saving them together with streaming imagery data, annotations and relevant imagery metadata, including appended imagery metadata and semantic metadata and annotations, and saving them together in single file format structures as may be required or allowed by standards for clinical documentation or biomedical records storage, including those as specified in DICOM, C-CDA and FHIR Standards for interoperable health information exchange.

SUMMARY

A network system and methods for using the same for concurrent collaboration between users, collaborating by a variety of input illustrations, which include video, audio, telestrations, drawings and annotations, as well as collaborating on medical images that are typically accessed on a storage server database, imaging archives, or continuous streaming video.

The invention relates generally to a multimedia collaborative conferencing system and methods of using the same for generating input illustrations, which include telestrations, drawings and annotations on medical images concurrently with other users and saving participant cognitive collaborant input illustrations with streaming imagery data, annotations and relevant imagery metadata, including appended imagery metadata in single file format structures, including those as specified in the DICOM Standard. Applicant's network system is known as the TIMS Clinical Network System. It is comprised of three essential components: one called TIMS Clini-Pod Network Servers (CNS); another called TIMS Clini-Ports; and a third called TIMS Clini-Docks, as depicted in FIG. 1. A Tele-Visual Imagery Informatics Management System is hereinafter referred to as TIMS. TIMS Clini-Pod Network Servers (CNS) are computers that manage users, security, authentication, authorization, image streams, channels and sessions within the TIMS Clinical Network System (i.e. the invention described herein) that allows for multiple users in multiple locations to concurrently collaborate on the images, each user to input highlighted graphic electronic traces and annotations over the medical image, encapsulate and single file save each and all input illustrations from participant cognitive collaborants, which include telestrations, drawings, and annotations together with streaming imagery data, annotations and relevant imagery metadata, including appended imagery metadata and semantic metadata and annotations, from collaboration sessions in single file format structures, known as collaborated imagery files, as may be required or allowed by standards for clinical documentation or medical records storage, including those as specified in the DICOM Standard. DICOM compliant files must contain both imagery data sets and metadata information.

TIMS Clini-Docks include a medical image acquisition system adapted for receiving and transmitting medical images, constructed from, a computer having communications capability adapted for acquisition and transmission of a plurality of medical imaging and video signals. Wherein the medical image and video signals are acquired at the medical device's native resolutions, transmitting the signals at their native resolutions and native frame rates to a receiving device, receiving the medical imaging video signals in analog or digital form, and if required, compressing and scaling the signal, converting the signal to digital form for transmission, and transmitting the digital signals using secure encryption protocols to a display device. TIMS Clini-Docks are capable of concurrently acquiring signals from a plurality of medical imaging systems, as depicted in FIG. 1, including but not limited to, ultrasound, Computer Tomography (CT) scan, fluoroscopy, endoscopy, magnetic resonance imaging, nuclear medicine, echocardiogram ultrasound and microscopy. Medical imaging equipment is also referred to as modalities. A more complete list of sources for DICOM imagery streams can be found in the DICOM Standard [PS 3.3 Part 3: Information Object definitions], which include video (imaging), audio (waveform), and clinical documents (structured reports).

TIMS Clini-Docks can also receive the video image signal from a plurality of video sources, including but not limited to, S-video, composite color and monochrome, component red blue green video (RGB, three additive primary colors), Digital Visual Interface (DVI), any video transport protocol including digital and analog protocols, high definition multimedia interface (HDMI, compact audio video interface uncompressed digital data), serial digital interface (SDI), and DICOM video in their native, enhanced or reduced resolutions or their native, enhanced or reduced frame rates. The component, known in this invention as TIMS Clini-Pod Network Servers (CNS), manage communications between all acquisition systems (TIMS Clini-Docks), between all TIMS Clini-Ports, the computer workstations used by cognitive collaborants during collaboration sessions, between hospital servers, located on site or remotely, that store hospital images, and hospital networks in both local area and wide area configurations.

TIMS Clini-Pod Network Servers (CNS) manage both live and archived streaming imagery data acquired from TIMS Clini-Docks, and archived imagery, including collaborated imagery files, retrieved in predetermined digital single file format structures, including those as specified in DICOM Standard, and stored locally in media libraries on participant cognitive collaborants computer storage devices, in image data repositories on tele-visual imagery informatics management system servers, in image data repositories on cloud storage devices and locations, in image data repositories on picture archiving and communications system repositories, on other image data repositories compliant with standards for digital imaging and communications in medicine, or on any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

A participant or user computer can be defined as typically made of several components such as a main circuit board assembly having a central processing unit, memory storage to store programs and files, other storage devices such as hard drives, and portable memory storage, a power supply, a sound and video circuit board assembly, a display, and an input device such as a keyboard, mouse, stylus pen and the like allowing control of the computer graphics user interface display, where any two or more of such components may be physically integrated or may be separate. In one depiction, a remote location communicates with the networked computer, for the purpose of collaborating and conferencing with medical streaming imagery data.

TIMS Servers (CNS) manage the master control functionality of the TIMS Clinical Network System. This functionality is achieved via the connection of TIMS Servers (CNS) to TIMS Clini-Docks and allows multiple users in multiple locations to view live all telestrations, and annotations from each of the users during collaboration sessions, as depicted in FIG. 1. Telestrations and annotations are added as appended layers over the source video and do not alter the source imagery. In addition, when multiple TIMS Clini-Docks are connected to multiple medical modalities, as shown in FIG. 1, TIMS Clini-Pod Network Servers (CNS) enable concurrent collaboration with each and all of these multiple sources of streaming imagery data. TIMS Clini-Pod Network Servers (CNS) dynamically control which of the multiple sources of streaming imagery data each TIMS Clini-Port wishes to view, as depicted in FIG. 3.

TIMS Clini-Pod Network Servers (CNS) are typically deployed in several configurations: Clini-Pod or pairs, typically 1-2 Clini-Pods (hub-and-spoke or peer-to-peer); Clini-Pod Quads, or teams [typically 2-4 Clini-Pods); Clini-Pod Squads, (typically four Quads, or 16 Pods) and Clini-Pod Hives [4 Clini-Pod Squads]. Local CNS network servers connect individual cognitive collaborants, also known as pod team members to devices in their Clini-Pod, as depicted in FIG. 13. Team CNS network servers interconnect four Clini-Pods each other to allow for four-party tele-visual communication and live synchronous collaboration with shared work products, as depicted in FIG. 14. Hive CNS network servers connect four or more team network servers as depicted in FIG. 15. TIMS Clini-Pod Network Servers can be deployed in point-to-point, hub-and-spoke and mesh chord networks, as depicted in FIG. 16, as well as in other network configurations described in the Bellcore Telecommunications Management Network [TMN] architecture. In particular, TIMS Clini-Pod Network Servers can be deployed in core-spine-leaf network topologies, as depicted in FIG. 17, as well as in 2-tier, 3-tier or N-tier application architectures, as depicted in FIG. 18.

TIMS Clini-Port software applications allow participant cognitive collaborants to add other sources of streaming imagery data by selecting the "add+" channel selection tab, and viewed on the channel tabs of the multi stream viewer as shown in FIG. 3, (channel 1X . . . ). The multi-channel stream view capability of TIMS Clini-Port software applications allow concurrent viewing of multiple channels of both live and archived medical imagery streams as depicted in FIG. 7. The multi-channel stream view selection capability is depicted in FIG. 9, and again in FIG. 10 with multiple channels of both live ("stream") and archived (image "81420095249.jpg, and image "99200982617.mpg") medical imagery streams selected for capture, retrieval and concurrent viewing during a collaboration session. TIMS Clini-Port software applications include DICOM view capability, which allows participant cognitive collaborants to view, communicate, collaborate, consult and instruct with DICOM imagery streams. TIMS Clini-Port software applications include capabilities to view non-DICOM imagery as well, which allows participant cognitive collaborants to view, communicate, collaborate, consult and instruct with non-DICOM imagery streams. The multi-channel stream view capability of TIMS Clini-Port software applications allows participant cognitive collaborants to capture, retrieve and concurrently view both live and archived medical imagery streams for communication, collaboration, consultation and instruction with one or more sources of streaming imagery data by one or more participant cognitive collaborants, with both DICOM and non-DICOM imagery streams during collaboration sessions. Each participant cognitive collaborant, some of whom may be located remotely to the imaging modalities, is able to view, analyze, discuss and comment on each of the input illustrations from participant cognitive collaborants concurrently, live, and save such analysis or discussion as may be clinically relevant.

In one embodiment, the connection of TIMS Clini-Pod Network Servers (CNS) to TIMS Clini-Docks allows TIMS Clini-Ports to customize preferences for capture, retrieval, and viewing of streaming imagery data while the patient is still on the examination table. TIMS Clini-Ports can have direct access and control of the streaming imagery data and maintain the native resolution and frame rate output from the medical modality. If desired, TIMS Clini-Ports can adjust the native resolution, frame rate, and compression of the streaming imagery data specific to the user's preferences. In addition, TIMS Clini-Ports are able to live instruct clinicians who are controlling streaming imagery data at their respective modality sources, and view the results of those instructions to ensure that imagery acquired is consistent with user preferences, as depicted in FIG. 3. Those instructions are conveyed via two way communication between user and clinician with voice, text, video or telestrations within the TIMS Clini-Pod Network System and are not reliant upon any external communications network.

Without access to master control of TIMS Clini-Docks by TIMS Clini-Pod Network Servers (CNS), imagery viewed by a remote client using another invention is limited to the quality of the view and capture settings specified by others, which may be different than those desired or required by the remote client. TIMS Clini-Docks are multichannel streamer stacks that allow live capture and archived retrieval for tele-visual communications with: (1) streaming video; (2) medical imagery modalities and waveforms; (3) electronic medical records; and (4) clinical and multiomic maps and biometric data stream visualizations.

As used herein, "streaming medical imagery" includes all information objects described in the DICOM Standard, including images, video, modality imaging and waveforms—audio, visual and haptic wave forms and files, medical records and clinical documents, multiomic—phenotypic, genomic, metabolomic, pathomic, radiomic, radiopathomic and radiogenomic—maps and clinical data sets, including those as described in the Institute of Medicine's *Towards Precision Medicine—A New Taxonomy of Disease*; along with biometric data stream visualizations from connected medical devices, signals and sensors used for local and remote patient monitoring.

In one embodiment TIMS Clini-Docks can be deployed in four (4) dual channel streamer stacks to accommodate both live and archived streaming imagery data from these four principal modalities for tele-visual communications and collaboration with imagery informatics. Clini-Dock streamer Channel (1) is typically reserved for video communications and conferencing among team members and other cognitive collaborants. Channel (2) normally designated for electronic medical records and patient monitoring; Channel (3) for medical imaging modalities and wave forms. Channel (4) for data mapping and interactive biometric data stream visualizations, including virtual reality and augmented reality displays. The TIMS Clini-Port typically has one or more multi-channel monitors for connected devices, which can be situated locally, within the Clini-Pod, or at remote locations, including other Clini-Pods.

TIMS Clini-Docks, due to its novel capabilities, can acquire analog or digital video signals, standard or non-standard video resolutions, medical or non-medical imagery, live or archived imagery, and compressed or uncompressed imagery formats. TIMS Clini-Docks converts analog sources of streaming imagery data, as well as non-standard sources of streaming imagery data into digital imagery data sets for use by participant cognitive collaborants during collaboration sessions. TIMS Clini-Docks can also convert non DICOM digital imagery data sets, including non DICOM modality imaging (e.g. video), waveform data (e.g. voice, audio, haptic), and structured reports (DICOM-SR from PACS) and clinical documents (CCD, CCR from EHR medical records systems) into DICOM imagery streams for use by participant cognitive collaborants during collaboration sessions. The TIMS Clini-Dock stack depicted in FIG. 1 allows for capture of multiple sources of streaming imagery data in any and all combinations of the preceding specifications, (e.g. both DICOM and non-DICOM imagery streams, standard and non-standard imagery streams, and compressed and uncompressed imagery streams) and allows TIMS Clini-Ports concurrent viewing of multiple sources of streaming imagery data. TIMS Clini-Docks incorporate approved medical device components that processes any video output from a video source into an image stream, including but not limited to streaming imagery data from medical modalities, as depicted in FIG. 1.

TIMS Clini-Docks are connected directly to multiple sources of streaming imagery data, as depicted in FIG. 1, and continuously streams images to TIMS Clini-Pod Network Servers (CNS). Any number of TIMS Clini-Ports can request information from a TIMS Clini-Pod Network Servers (CNS). Each TIMS Clini-Port in a conference with another or other TIMS Clini-Ports can view all the TIMS Clini-Port object inputs as they occur. TIMS Clini-Ports refer to computer workstations used by cognitive collaborants during collaboration sessions, typically for medical review and diagnosis of patient image data.

TIMS Clini-Pod Network Servers (CNS) keep track of all TIMS Clini-Docks that have image streams available and displays a list of image streams available TIMS Clini-Ports, as depicted in FIG. 3. TIMS Clini-Pod Network Servers (CNS) communicate with image repositories, including but not limited to PACS system repositories, and store information on all TIMS Clini-Ports' computers live. TIMS Clini-Pod Network Servers (CNS) include software components that manage streaming requests to TIMS Clini-Docks; manage authentication and authorization tasks for access and privileges; manages users information, roles, session logs and, configurations for TIMS Clini-Pod Network Servers (CNS) and TIMS Clini-Docks; manage web services interactions with TIMS Clini-Ports; send, query and retrieve collections of one or more streaming imagery data files, including collaborated imagery files, also known as studies, to and from image repositories, as depicted in FIGS. 10 and 11, including but not limited to DICOM compliant image repositories, e.g., PACS; specify unique combinations of image quality, resolution, compression and frame rates as may be required for each collaboration session, as depicted in FIG. 3; access patient information from a DICOM Modality Worklist utility (DMWL); collaborated imagery files, to TIMS Clini-Ports; manage text chat information; manage DICOM send services, wherein the DICOM send service sends the annotated images to PACS or DICOM compliant image repositories, also known as medical image archives, as depicted in FIG. 10; allow for query and retrieve functionality that retrieves lists of DICOM studies from PACS servers and DICOM compliant image repositories and sends those studies to TIMS Clini-Ports.

A DICOM study is defined as a collection of one or more medical images and patient data combined in single file format structures, including those as specified in the DICOM Standard. DICOM Modality Worklist is defined as a software utility that invokes DICOM query and retrieve functionality which enables imaging equipment (e.g. medical modalities) to query medical image stores, including but not limited to PACS, and obtains details of patient and scheduled examinations electronically, including patient demographics and study data, avoiding the need to type patient information multiple times, as depicted in FIG. 10. Clini-Pods typically deploy with Clini-CDR (Clinical Data Repositories, consisting of p-CKR [personalized Clinical Knowledge Repositories] with local storage of CIFs and clinical cognitive vismemes in personalized clinical knowledge repositories, clinical cognitive vismeme vaults; and metadata repositories which house reference links to collaborated imagery files, along with dicomized cognitive collaboration security tokens which provide granular control over access to shared imagery files stored in clinical data repositories, personalized clinical knowledge repositories, clinical cognitive vismeme vaults and metadata repositories.

Security tokens for cognitive collaboration, selectively providing access to imagery information objects, their associated metatdata and annotations, including personal health information (PHI), can be created, read, updated or deleted, with concurrence by or among one or more participant cognitive collaborants, before, during or after cognitive collaboration s sessions. Security tokens for cognitive collaboration can be maintained in separate metadata repositories, including blockchain metadata repositories and blockchain data ledgers, and accessed by cognitive collaborants with appropriate security privileges.

TIMS Clini-Pod Network Servers (CNS) also manage all the participant cognitive collaborant input illustrations, specifically, the entire participant cognitive collaborant input illustrations, sketches, drawings, telestrations and annotations. Participant cognitive collaborant input illustrations as previously defined herein include, but are not limited to telestrations, drawings, sketches, text annotations, including letter character text and numeric character text, image annotations, wave form annotations, voice annotations, video annotations, augmented reality imagery annotations, 3D/4D imagery annotations, outcomes annotations, costs annotations, resource consumption/utilization annotations, haptic annotations, imagery metadata and appended imagery metadata, as depicted in FIG. 7. All participant cognitive collaborant input illustrations are managed by TIMS Clini-Pod Network Servers (CNS) based on a file sharing scheme where new input illustrations keep getting appended to files on TIMS Clini-Pod Network Servers (CNS). TIMS Clini-Pod Network Servers (CNS) distribute copies of streaming imagery data to each of the participant cognitive collaborants. Since participant cognitive collaborants collaborate only with copies of images, they do not alter the original streaming imagery data in any way. This approach of generating input illustrations on TIMS Clini-Pod Network Servers (CNS), and distributing only those input illustrations and not the underlying images to each participant cognitive collaborant, significantly improves operating performance and reduces image latency and wait times. That method of moving images with illustrations back and forth from a computer to a server, results in losing illustration quality or consuming more bandwidth. However, with this novel invention, the process of multi-layer multi user input illustrations on any underlying images, including streaming imagery data, and updating and appending on the streaming imagery data with multiparty annotations and metadata without sacrificing network bandwidth, is novel to this invention.

TIMS Clini-Pod Network Servers (CNS) allow TIMS Clini-Ports to create collaborated imagery files synchronously or asynchronously. TIMS Clini-Pod Network Servers (CNS) use a process of local registration to identify the image frames needed for viewing on each of the participant cognitive collaborant computers, and sends to each of them only the image frames necessary for participation in a collaboration session. TIMS Clini-Pod Network Servers (CNS) enable each participant cognitive collaborant to use a scalable window so all input illustrations for each and every participant cognitive collaborant are dynamically ratio metric based on the underlying image aspect ratio of the respective participant cognitive collaborant computer. Therefore, all the input illustrations always point to the part of the window and image as originally intended, regardless of window size on the clients computer display. A central frame counter originating in the participant cognitive collaborant computer, which has play/pause control, issues frame synchronization commands to synchronize the image streams on all participant cognitive collaborants' computers. This method significantly reduces bandwidth requirements and improves responsiveness of system updates and imagery appends. Each client computer which has play/pause control also sends synchronizing commands whenever its displayed images are paused. This ensures that the same frame is available to all participating clients by broadcasting that pause frame number along with the pause command to all participating clients.

Client participants can receive video streams directly from TIMS Clini-Docks using a local area network. The invention can also detect if a user has low bandwidth, in transmission, or in reception, or in both and can compensate by only sending selected image frames to that user. For example, with low bandwidth TIMS Clini-Pod Network Servers (CNS) can send every third, fifth, or Nth frame of a collaborated imagery to clients so that client does not have any perceptible delay. Remote client participants using the internet must receive all imagery from TIMS Clini-Pod Network Servers (CNS) for secure transmission, rather than directly from local TIMS Clini-Docks, to ensure streaming imagery data is not transmitted over the internet without encryption.

TIMS Clini-Ports, also known as participant cognitive collaborants, can take several roles. Each participant cognitive collaborant can capture, retrieve and concurrently view both live and archived streaming imagery data of their own choosing, including medical imagery streams selected for the collaboration session; capture, retrieve and concurrently view both live and archived streaming imagery data streams selected by other participant cognitive collaborants, including medical imagery selected for the collaboration session; each participant cognitive collaborant can add multiple sources of streaming imagery data, also referred to as multiple channels, of both live and archived streaming imagery data for other participant cognitive collaborants to capture, retrieve and concurrently view; capture, retrieve and concurrently view multiple sources of both live and archived streaming imagery data, including medical imagery streams selected for a collaboration session; concurrently add input illustrations on both live and archived streaming imagery data; taking on any and all of the above roles dynamically, as depicted in FIG. 4.

In addition, TIMS Clini-Port software applications are collaborative, interactive; tools for synchronous or asynchronous media annotation, which can be used with medical files to enable participant cognitive collaborants to communicate, collaborate, consult and instruct with medical images for clinical review and discussions and deciding on relevant medical procedures.

This novel invention—combination streamer-splitter-server-router-network gateway servers—allows any of the TIMS Clini-Ports to host a collaboration session with any other TIMS Clini-Port, in various network configurations, including peer-to-peer, hub-and-spoke, mesh chord networks, as depicted in FIG. 16. A collaboration session host selects any number of participant cognitive collaborants from their contact list, as depicted in FIG. 5, and sends a request to those clients with whom they wish to collaborate. Each participant cognitive collaborant receiving the request can elect to join or decline the session by selecting the appropriate button on the dialog box that appears on their computer monitor, as depicted in FIG. 6. Upon acceptance of the request, the cognitive collaborant client's monitor is automatically switched to view the same imagery as the collaboration session host. The host can select live streaming imagery data from any of the available TIMS Clini-Docks, as depicted in FIG. 3, can also select from any archived streaming imagery data available through the query and retrieve functions, as depicted in FIG. 11, and concurrently collaborate using all selected imagery data streams—live, archived or both—for multimodal clinical communications, collaboration, consultation or instruction with all participant cognitive collaborant clients during the collaboration session.

All input illustrations added by participant cognitive collaborants are concurrently visible to all of the other participant cognitive collaborants. In addition, each participant cognitive collaborant can add input illustrations, which include telestrations, drawings, text annotations, image annotations, wave form annotations, voice annotations, video annotations, augmented reality imagery annotations, 3D/4D imagery annotations, outcomes annotations, costs annotations, resource consumption/utilization annotations, haptic annotations, to streaming imagery data, together with relevant imagery metadata, including appended imagery metadata and semantic metadata and annotations. Furthermore, each participant cognitive collaborant client can also use the TIMS Clini-Pod Network System to chat with each other during a collaboration session using a text chat facility. A separate text window box is displayed that allows for each participant cognitive collaborant to instant message each other in text format and include those images as input illustrations, as depicted in FIG. 7. One feature of this invention is that the host can disable the edit control of any client, such that a particular client will not be able to add or edit the annotations or telestrations, as depicted in FIG. 8. At this point, the client can only view the annotations made by others. The host can also pass the control of the video stream start/stop/pause functions to another client. This control allows the host to enable or disable the functionality to all clients or selected clients and can be done at any time during the collaboration session. At the conclusion of the session, participant cognitive collaborants can encapsulate and save all input illustrations, which include telestrations, drawings and annotations together with streaming imagery data, and relevant imagery metadata, including appended imagery metadata and semantic metadata and annotations, from the collaboration session, in single file format structures, known as collaborated imagery files. Collaborated Imagery Files are encapsulated and saved in single file format structures, as may be required or allowed by standards for clinical documentation or medical records storage, including those as specified in the DICOM Standard (e.g., as DICOM files). Participant cognitive collaborant clients can send collaborated imagery files to any PACS or DICOM compliant image data repository, or send to any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations. A session log is recorded and saved on the TIMS server, as depicted in FIG. 9.

The invention also works with wearable signals, sensors, devices and monitors, collectively "mobile computing", also known as Personal Digital Assistants. Participants (PDA) clients can use these PDAs to view, consult and collaborate on DICOM images. Personal digital assistant is any small mobile hand held device that provides computing and information storage such as hand held computers, phones, media display devices and handheld computers, including watches and vison.

The invention enables both synchronous and asynchronous multimodal clinical communications, collaboration, consultation and instruction between and among participant cognitive collaborants, including heterogeneous networked teams of persons, machines, devices, neural networks, robots and algorithms. And specifically, the invention enables multimodal clinical communications, collaboration, consultation and instruction during various stages of medical disease and injury management, including detection, diagnosis, prognosis, treatment, measurement, monitoring and reporting, as well as workflow optimization with operational analytics for outcomes, performance, results, resource utilization, resource consumption and costs.

In one embodiment the invention provides for a unique streamer-splitter-server-router functional combination in a single network edge device, a neurosynaptic network node, having bi-directional communications capability with other Pod network gateway servers via network, video and wireless connectivity. Network gateway servers—neurosynaptic network nodes—can be combined in various multichannel multiplexed combinations, including pod pairs (2), pod quads (4), pod squads (16), and pod hive clusters (64), as depicted in FIGS. 13, 14 and 15. Neurosynaptic network servers can be deployed in various network architectures, including point-to-point (peer-to-peer), hub-and-spoke, and mesh chords, as depicted in FIG. 16. Neurosynaptic network servers can be deployed can be deployed in core-spine-leaf network topologies, as depicted in FIG. 17, as well as in 2-tier, 3-tier or N-tier application architectures, as depicted in FIG. 18. These embodiments allow for dynamic neurosynaptic connectivity for multichannel multiplexed networked visual communications.

In another embodiment the invention provides a method for recursive cognitive enrichment and collaborative knowledge exchange between and among cognitive collaborants, including heterogeneous networked teams of persons, machines, devices, neural networks, robots and algorithms. Specifically it provides neurosynaptic network connectivity enabling both synchronous and asynchronous multimodal clinical communications, collaboration, consultation, instruction, that includes viewing, curating, annotating and tagging, using one or more sources of multichannel, multiplexed heterogeneous streaming imagery data, including both medical and non-medical streaming imagery data.

This embodiment also provides a method for rapid, adaptive deep learning and specialist skills acquisition by and among cognitive collaborants, including heterogeneous networked teams of persons, machines, devices, neural networks robots and algorithms, with neurosynaptic network connectivity enabling both synchronous and asynchronous multimodal clinical communications, collaboration, consultation, instruction, that includes viewing, curating, annotating and tagging, using one or more sources of multichannel, multiplexed heterogeneous streaming imagery data, including both medical and non-medical streaming imagery data, together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, clinical documents and key performance indicators during various stages of medical disease and injury management, including detection, diagnosis, prognosis, treatment, measurement, monitoring and reporting, as well as workflow optimization with operational analytics for outcomes, performance, results, resource utilization, resource consumption and costs.

A medical imagery stream is defined as a collection of one or more sources of streaming imagery data which comprise at least one image frame that defines a time progression of output from a video source. TIMS Clini-Docks maintain image quality from source modalities as required for conformance to DICOM Standards for clinical use. TIMS Clini-Docks specify streamer components that have secured regulatory clearances for transmission and viewing of medical imagery streams for clinical diagnostic purposes.

In one embodiment, TIMS Clini-Pod Network Servers (CNS) provide live video and audio communications, as well as a method of recording, transmitting and saving images in single file format structures, including those as specified in the DICOM Standard. DICOM is a medical imaging standard common in the medical industry. DICOM can also be defined as a standard in the field of medical informatics for exchanging digital information between medical imaging equipment (such as radiological imaging) and ensuring interoperability with other systems. DICOM, including protocols for device communication over a network, syntax and semantics for commands and associated information that can be exchanged using protocols, a set of storage services and devices claiming conformation to the standard, as well as file format and medical directory structures to facilitate access to images and related information stored on media that shares information. The embodiment can serve as the connection point between any medical imaging modality and a hospital PACS, medical archive or other image repository, including clinical data repositories, personalized clinical knowledge repositories, clinical cognitive vismeme vaults and metadata repositories.

One component of this invention, TIMS Clini-Pod Network Servers (CNS), are able to connect DICOM equipment and older non-DICOM equipment to a hospital network, allowing imaging studies to be stored and saved. The TIMS Clini-Pod Network System, this invention described herein, briefly described as a trace overlay and annotation system that users can collaborate with each other live, each viewing each other's object inputs and those object inputs can be encapsulated and saved in single file format structures, including those as specified in the DICOM Standard, in PACS, in a DICOM compliant image archives, or in other image repositories.

Another embodiment the TIMS Clini-Pod CNS network system can be deployed as collaboration portals for multiparty cognitive collaboration among specialist providers; care coordination for caregiving teams both local and remote; and patient provider engagement, the support of meaningful use goals and objectives for electronic medical records. Clini-Pod CNS also support health information exchange for integrated delivery systems; for biomedical, clinical and genomic mapping and multisensory data stream visualizations, as well as clinical decision support for value care-giving teams.

Still other embodiments provide networked informatics connectivity for medical kiosks, offices and retail clinics, ambulatory care and nursing facilities. Often these facilities have limited connectivity for access to hospital-based electronic medical systems. In those circumstances the TIMS Clini-Pod CNS as "LAND" [Local Adapter for Network Distribution] and "SEE" [Surrogate Electronic Health Record Environment] to facilitate health information exchange with hospitals and other caregiving facilities. Use of TIMS Clini-Pod access and enable groups with access to EHR systems to share electronic medical information with those who do not, and specifically by health information exchange with Consolidated Clinical Document Architecture (C-CDA") compliant documents, including Continuity of Care Documents (CCD, CCD+, etc.), Fast Healthcare Interoperability Resources ("FHIR") and Universal Transfer Forms (UTF.)

BRIEF DESCRIPTION OF DRAWINGS

Other objects, features, and advantages will occur to those skilled in the art from the following description of an embodiment and the accompanying drawings, in which:

FIG. 9, depicts a graphic user interface screen shot list of multiple cognitive collaboration sessions.

FIG. 29, depicts building semantic data trails with metadata extraction from structured, semi-structured and unstructured data, including biomedical data from medical imaging modalities.

FIG. 42, depicts Pattern Matching Algorithms for Multiple Classes of Oncology Images.

FIG. 58, depicts Visio-Spatial Algorithms Development for Precision Guided Surgery.

DETAILED DESCRIPTION

Figure 1:
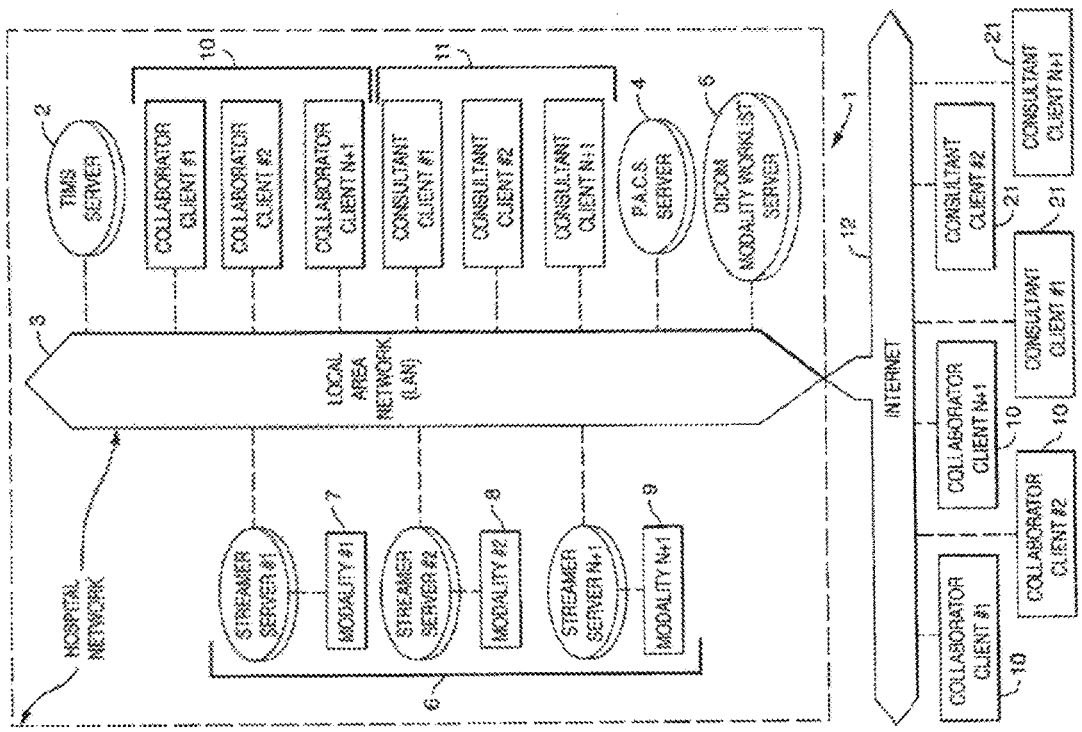
FIG. 1, depicts a block diagram of the invention.
Figure 2:
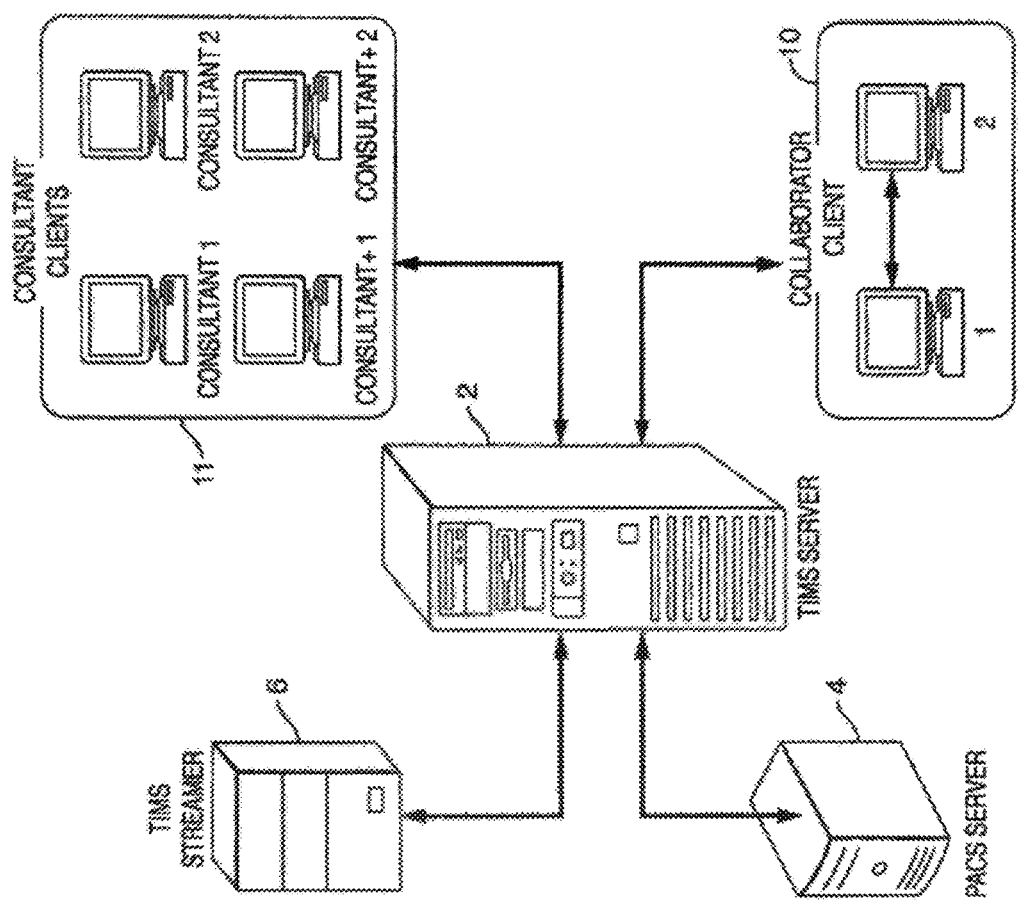
FIG. 2, depicts a block diagram of a portion of the system.

A network system 1 for allowing users to concurrently communicate live; concurrently collaborate live, concurrently consult live, and concurrently instruct live while concurrently viewing multiple sources of streaming imagery data 13 on a display screen using sketched and annotated participant cognitive collaborant input illustrations over streaming imagery data 13 among a group of remotely located participant cognitive collaborators 10, including heterogeneous networked teams of persons, machines, devices, neural networks, robots and algorithms.

The network system having at least one or more TIMS Clini-Pod Network Servers (CNS) 2 including associated data bases in communication with local area networks 3, in some circumstances connected to and having access to a medical PACS server 4 including associated database all capable of using the protocols required by the DICOM Standard and all having access to DICOM modality work list utilities for appending imagery metadata 5 including associated databases providing medical patient metadata, as well as imagery metatdata, semantic metadata and annotations, and archived annotated imagery. To collect streaming imagery data 13 the system together with at least one TIMS Clini-Dock 6 in contact with the local area network 3 wherein the TIMS Clini-Dock 6 is providing live streaming imagery data to the local area network 3 as it receives concurrent sources of live streaming imagery data 6 from multiple medical modalities 7, 8, 9 such as, but not limited to, ultrasound, fluoroscopy and video. A participant cognitive collaborant can view streaming imagery data 13 in single file format structures, including those as specified in the DICOM Standard together with participant cognitive collaborant input illustrations 18 which include, telestrations 21, drawings 22 and annotations 234 (known herein as input illustrations from participant cognitive collaborants) over the streaming imagery data and saving that streaming imagery data, relevant imagery metadata, including appended imagery metadata and semantic metadata and annotations, together with input illustrations from participant cognitive collaborants 18 in single file format structures, including those as specified in the DICOM Standard, locally in media libraries or image data repositories on their respective computer storage devices, in image data repositories on TIMS Clini-Pod Network Servers (CNS) 2, in image data repositories on cloud storage devices and locations, in image data repositories on picture archiving and communications systems PACS 4 or in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

This invention allows for one or more TIMS Clini-Ports 10 to concurrently use the network system at the same time. The network system 1 also allows participant cognitive collaborants to concurrently collaborate live, as defined by this system. The plurality of TIMS Clini-Ports can concurrently view multiple sources of live and archived streaming imagery data-13, and concurrently create input illustrations 18 over that streaming imagery data 13 which include telestrations 21, drawings 22 and annotations 23, as they are appended to that imagery, and encapsulate and save those participant cognitive collaborant input illustrations, including telestrations, drawings, and annotations, together with streaming imagery data, and relevant imagery metadata, including appended imagery metadata, from the collaboration session in single file format structures, known as collaborated imagery files. The network system 1' single file encapsulate and save' functionality encapsulates and saves collaborated imagery files in single file format structures, as may be required or allowed by standards for clinical documentation or medical records storage, including those as specified in the DICOM Standard, Clini-Pod Network locally in media libraries or image data repositories on their respective computer storage devices, in image data repositories on TIMS Clini-Pod Network Servers (CNS) 2, in image data repositories on cloud storage devices and locations, in image data repositories on picture archiving and communications systems PACS 4 or in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

TIMS Clini-Ports can retrieve archived collaborated imagery files for use during current or future collaboration sessions. TIMS Clini-Ports can include collaborated imagery files in patient studies. In one embodiment, a collaboration session can include one or more participant cognitive collaborants that can utilize personal digital assistants (PDA) over the internet 12.

A method for allowing one or more participant cognitive collaborants to concurrently collaborate live on medical images 13, all participants clients running substantially the same TIMS Clini-Port software application programs on each of the participant cognitive collaborant's computers; storing the programs on each of the participant cognitive collaborant's computers. Each participant cognitive collaborant computer displaying the graphic user interface output 25 of those programs on their computer display. Each participant cognitive collaborant computer linking to each other and to TIMS Clini-Pod Network Servers (CNS) 2 using local area networks 3. All TIMS Clini-Ports 10 have access to local area networks 3 and internet 12. TIMS Clini-Pod Network Servers (CNS) 2 providing authentication and authorization to each participant cognitive collaborant wherein linking the participant cognitive collaborant to DICOM Modality Worklist utilities 5, to image data repositories connected to picture archiving and communications systems via PACS servers 4, to other image data repositories compliant with standards for digital imaging and communications in medicine DICOM, to image data repositories connected via internet 12 to cloud storage devices and locations or on any other repository that allows streaming imagery data, annotations and metadata, including semantic metadata and annotations, to be combined in native single file format structures for viewing medical images 13, including clinical data repositories, personalized clinical knowledge repositories, clinical cognitive vismeme vaults and metadata repositories.

Streaming imagery data into local area networks 3 wherein TIMS Clini-Docks 6 are connected directly to medical modalities 7, 8, 9 acquiring live streaming imagery data or archived streaming imagery data, streaming that imagery data to TIMS Clini-Ports 10 via local area networks 3. TIMS Clini-Ports 10 acquire lists 15 of available medical modalities 7, 8, 9 from a local area network 3. Included in this network is are TIMS Clini-Pod Network Servers (CNS) 2 having associated databases, identifying each participant cognitive collaborant and the streaming imagery data available to each participant cognitive collaborant; identifying each participant cognitive collaborant the streaming imagery data that is available on each participant cognitive collaborant's computer. Also, local area networks 3 can be connected to the internet 12.

Figure 3:
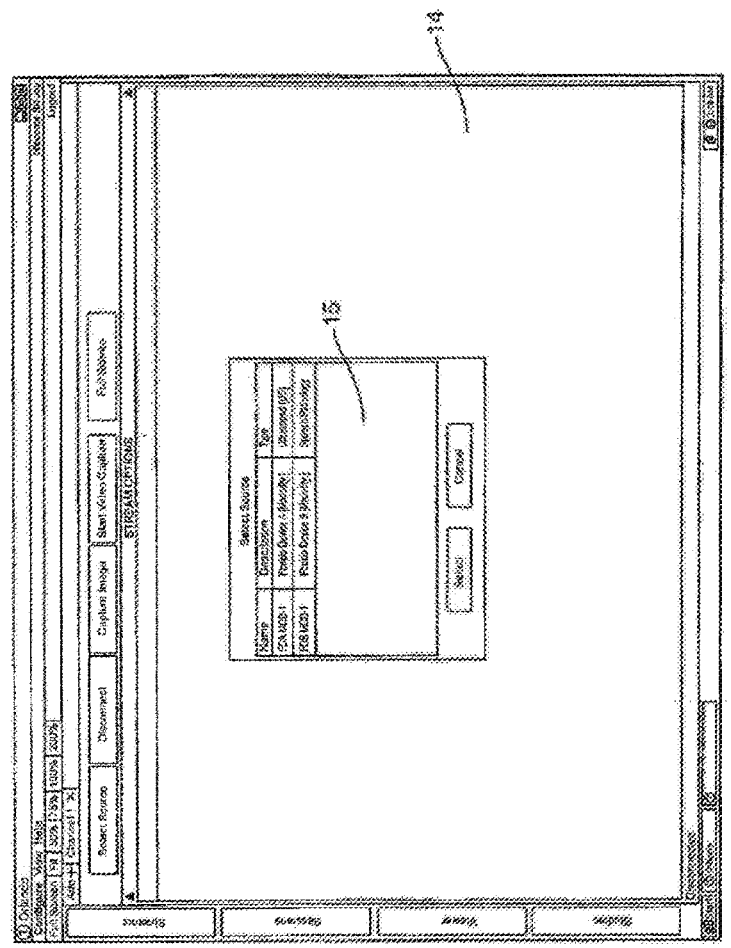
FIG. 3, depicts a graphic user interface screen shot of a cognitive collaborant workstation: client imagery source selection display.

When a participant cognitive collaborant wants to view medical imagery and collaborate on that streaming imagery data with others, that participant cognitive collaborant selects a channel on the multi-channel source selection tab for viewing streaming imagery data 15, 25 so he/she can initiate a collaboration session, as depicted in FIG. 3. When participant cognitive collaborants are in a collaboration session, TIMS Clini-Pod Network Servers (CNS) 2 are providing updates to each participant cognitive collaborant's computer at a rapid frame rate so each participant cognitive collaborant's computer concurrently displays the same imagery. In other words, TIMS Clini-Pod Network Servers (CNS) 2 updates any changes to each and all of the streaming imagery data on each of the participant cognitive collaborant's computers with synchronized signals sent over local area networks 3 dynamically such that all streaming imagery data on all participant cognitive collaborant computer displays are the same, including sending each participant cognitive collaborant's input illustrations 18, which include, telestrations 21, drawings 22, and annotations 23, and illustrations over the streaming imagery data 13 made by any of the participant cognitive collaborants 10.

TIMS Clini-Pod Network Servers (CNS) 2 with dynamic signal synchronization ensures that the same imagery refresh rate is concurrently available on all participant cognitive collaborant computers. TIMS Clini-Pod Network Servers (CNS) 2 use a process of local registration to identify the image frames needed for viewing on each of the participant cognitive collaborant computers, and send to each of them only the image frames necessary for participation in a collaboration session. TIMS Clini-Pod Network Servers (CNS) 2 enables each participant cognitive collaborant 10 to use a scalable window so all input illustrations 18 for each and every participant cognitive collaborant 10 are dynamically ratio metric based on the underlying image aspect ratio of the respective computer of each participant cognitive collaborant 10. Each participant cognitive collaborant 10 views what every other authorized participant cognitive collaborant 10 views in that session.

TIMS Clini-Pod Network Servers (CNS) 2 distribute copies of streaming imagery data selected for use during a collaboration session to each of the participant cognitive collaborants. Since participant cognitive collaborants 10 collaborate only with copies of images, they do not alter the original streaming imagery data in any way. TIMS Clini-Pod Network Servers (CNS) 2 with dynamic signal synchronization allows at least one participant cognitive collaborant 10 to telestrate 21, draw 22, annotate 23, input illustrations 18 over the streaming imagery data 13 in a concurrently collaboration session wherein a participant cognitive collaborant 10 is telestrating 21, drawing 22, annotating 23 input illustrations 18 over the streaming imagery data 13. This approach of generating input illustrations 18 on TIMS Clini-Pod Network Servers (CNS) 2, and distributing only those input illustrations 18, and not the underlying images to each participant cognitive collaborant 10, significantly improves operating performance and reduces image latency and wait times.

TIMS Clini-Pod Network Servers (CNS) 2 manage input illustrations 18 from all participant cognitive collaborants 10 in a concurrently collaborative environment with image streams which can include multiple streams of streaming imagery data. TIMS Clini-Pod Network Servers (CNS) 2 manage participant cognitive collaborant 10 input illustrations 18, which include telestrations 21, drawings 22, and annotations 23 as they are appended to that imagery 13, and encapsulate and save those participant cognitive collaborant input illustrations 18, which include telestrations 21, drawings 22 and annotations 23 together with streaming imagery data 13, and relevant imagery metadata, including appended imagery metadata, from the collaboration session in single file format structures, known as collaborated imagery files.

Figure 4:
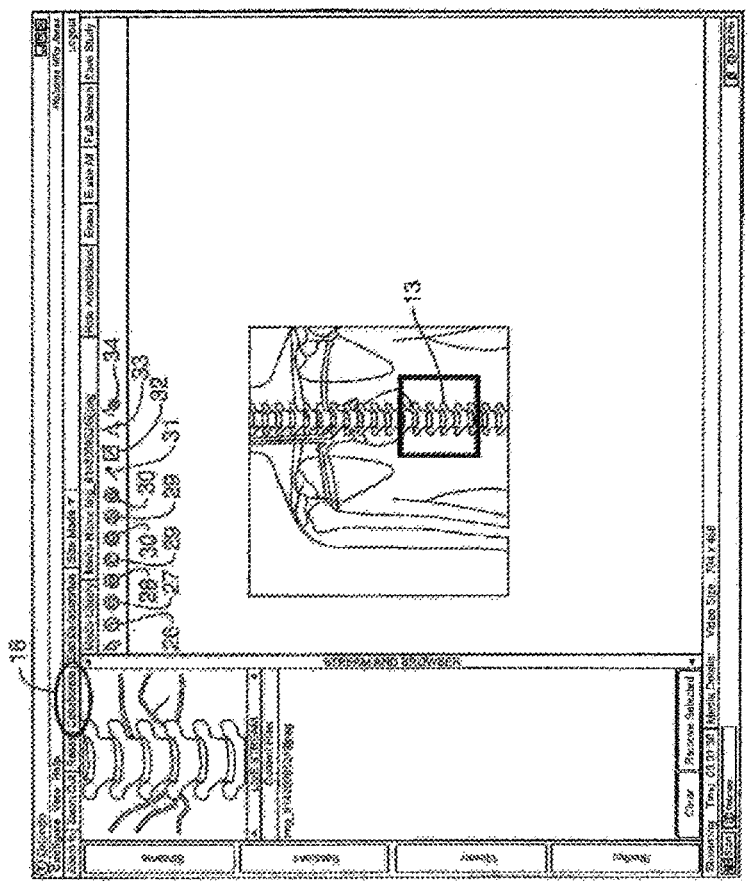
FIG. 4, depicts a graphic user interface screen shot of cognitive collaborant workstation: client source imagery with illustration tool bar and collaboration function.
Figure 5:
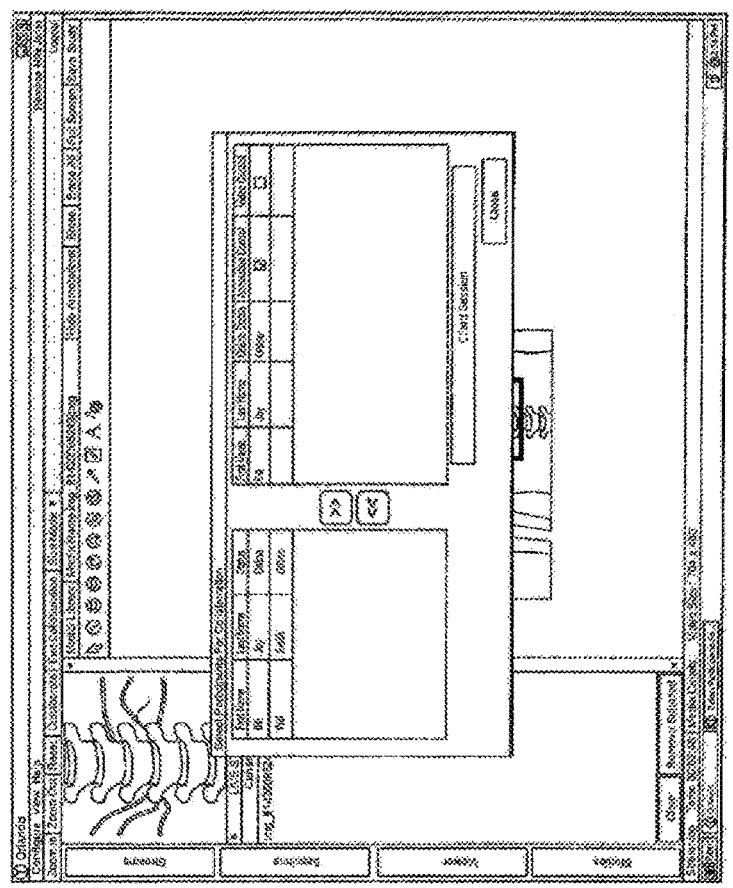
FIG. 5, depicts a graphic user interface screen shot of a cognitive collaborant workstation: client selecting participant cognitive collaborants for collaboration session.

TIMS Clini-Pod Network Servers (CNS) 2 'single file encapsulate and save' functionality encapsulates and saves collaborated imagery files in single file format structures, as may be required or allowed by standards for clinical documentation or medical records storage, including those as specified in the DICOM Standard. Users can encapsulate and save collaborated imagery files locally in media libraries or image data repositories on their respective computer storage devices, as depicted in FIG. 4, which contain all of the input illustrations 18 from all participant cognitive collaborants 10. Users can also encapsulate and save collaborated imagery files in image data repositories on TIMS Clini-Pod Network Servers (CNS) 2, in image data repositories on picture archiving and communications systems PACS 4, in other image data repositories compliant with standards for digital imaging and communications in medicine DICOM, or on any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

Figure 9:
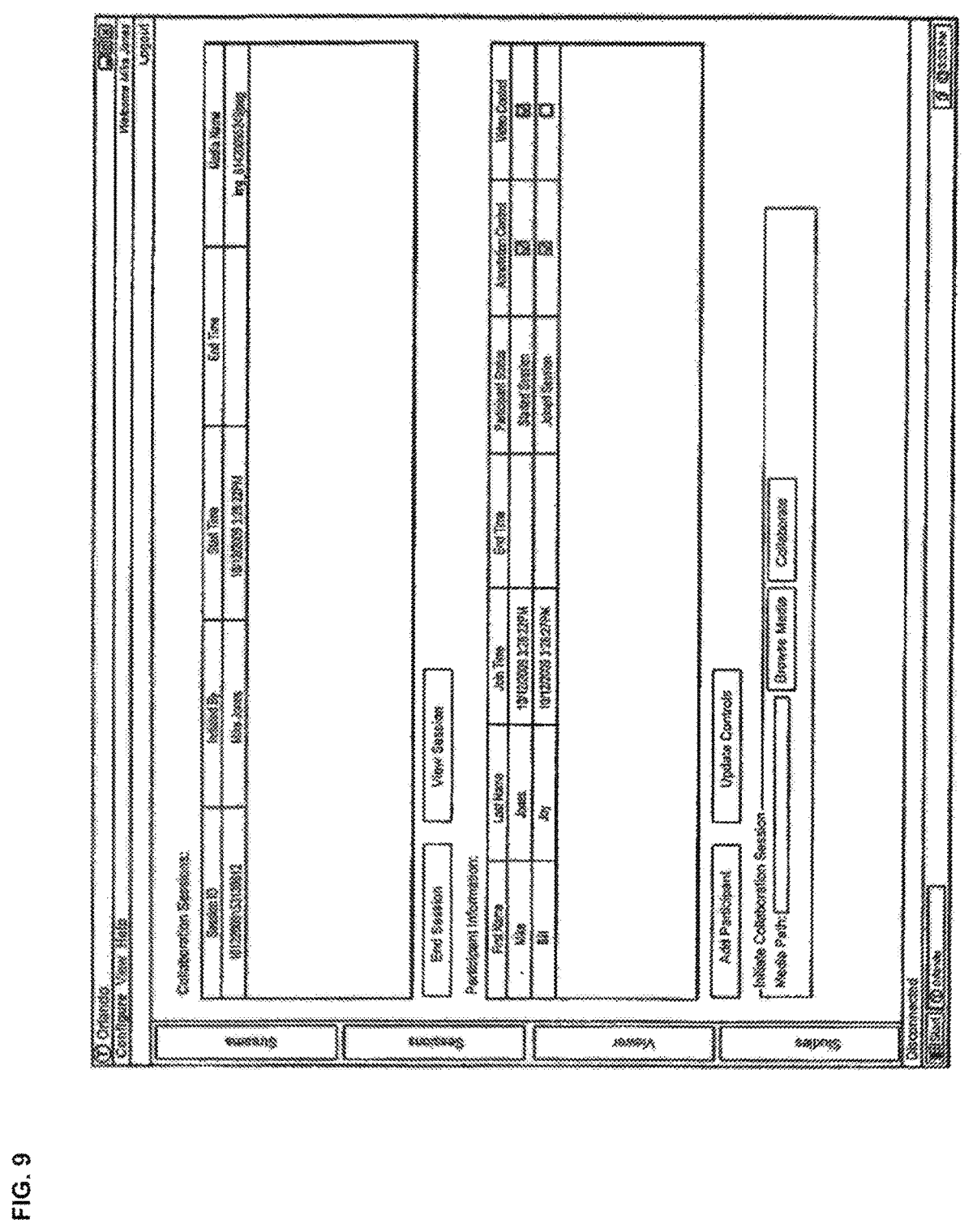

TIMS Clini-Pod Network Servers (CNS) 2 create session logs that include collaboration session identification, participant cognitive collaborant information, information about streaming imagery data, including associated patient metadata, along with session dates and times, as shown in FIG. 9.

In one embodiment, several participant cognitive collaborants 10, also known as Radiologist, Pathologist and Oncology Surgeon, utilize the network system 1 to collaborate in the provision of oncology care.

At Time 1, Radiologist retrieves patient's archived medical imagery from a PACS 4 image repository. Radiologist detects a suspicious nodule on several images and inputs telestrations 21 and drawings 22 indicating the location of the nodule, along with text annotations 23 characterizing its clinical significance and voice annotations 23 summarizing his findings. Radiologist utilizes the 'single file encapsulate and save' functionality of the network system 1 to incorporate those input illustrations 18, together with medical imagery data 13 and identifying patient metadata, in single file format structures, known as a collaborated imagery file (CIF #1). Radiologist archives the CIF #1, which has been encapsulated and saved in a single file format compliant with the DICOM Standard, and sends to PACS 4 for review and discussion with other members of the oncology care team.

At Time 2, Radiologist invites Pathologist to a collaboration session to discuss his findings of a suspicious nodule as described in CIF #1. While both participant cognitive collaborants 10 are concurrently viewing CIF #1, Radiologist retrieves several additional collaborated imagery files from his local media library, and from PACS 4, of relevant prior patient medical imagery for display and viewing during the collaboration session, as shown in FIG. 4. Participant cognitive collaborants 10 record, encapsulate and save their input illustrations 18 for each of several imagery files selected for discussion during the collaboration session, as CIF #2, #3, #4. Pathologist combines CIF #1 with CIF #2, #3, #4 as collaborated imagery study (CIS #1) and stores CIS #1 on PACS 4 for subsequent review and discussion with Oncology Surgeon, who was unavailable at Time 2 to join collaboration session.

At Time 3, Oncology Surgeon reviews CIS #1 and selects CIF #4 to create a surgical roadmap to guide tumor excision using input illustrations 18, which include telestrations 21, drawings 22, and voice annotations 23. Oncology Surgeon saves surgical roadmap as CIF #5.

At Time 4, Oncology Surgeon retrieves surgical roadmap (CIF #5), for intra-operative guidance during tumor removal.

At Time 5, during surgery, Oncology Surgeon invites Radiologist and Pathologist for intra-operative consultation during tumor excision.

At Time 6, participant cognitive collaborants—Oncology Surgeon, Radiologist, and Pathologist—utilize network system 1 to retrieve and concurrently view nodule (CIF #1), tumor pathology images (CIF #2, #3, #4), and surgical roadmap (CIF #5) from PACS 4, along with live streaming imagery data from endoscope 13 used during tumor excision.

Periodically during the surgical procedure, at Times 7, 8, 9, Oncology Surgeon consults with Pathologist to confirm sufficiency of margins around excised tumor. Pathologist confirms sufficiency of margins with telestrations 21, drawings 22, and text annotations 23, over live endoscopy images, saving all those input illustrations 18, together with associated streaming imagery data 13 in single file format structure as CIF #6.

At Time 10, Oncology Surgeon retrieves CIF #6 from PACS 4, which contains Pathologist's input illustrations 18 regarding excised tumor margins, and dictates a post-operative surgical report adding voice annotations 23, to telestrations 21, and drawings 22 to endoscopic images from excision surgery and saving in single file format structure as CIF #7.

At Time 11, Oncology Surgeon combines pre-operative surgical roadmap CIF #5 with post-operative surgical report CIF #7, along with pre-operative image study CIS #1 (which includes CIF #1, #2, #3, #4) into comprehensive clinical report (CIS #2) for distribution to the oncology care team.

Oncology Surgeon can encapsulate and save CIS #2 in single file format structures as specified in the DICOM Standard and send to PACS 4. Oncology Surgeon utilizes the 'single file encapsulate and save' functionality of the network system to encapsulate and save CIS #2 in single file format structures as specified in the DICOM Standard and send to PACS 4. Oncology Surgeon can also encapsulate and save CIS #2 in single file format structures as may be required or allowed for clinical documents, for storage in patient's electronic medical record, or for patient billing.

At Time 12, Oncology Surgeon retrieves CIS #2 from PACS 4, utilizes the network system 1 to remove all relevant identifying patient metadata, and encapsulates and saves as an anonymized collaborated imagery study (CIS #3) for use as teaching files with surgical fellows.

Figure 6:
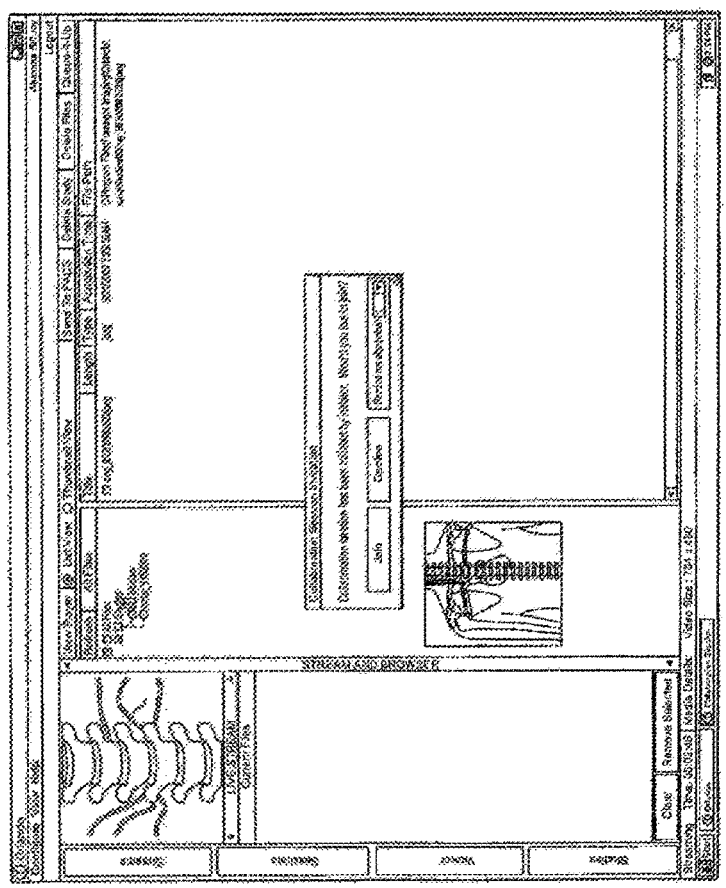
FIG. 6, depicts a graphic user interface screen shot of cognitive collaboration session initiation.
Figure 7:
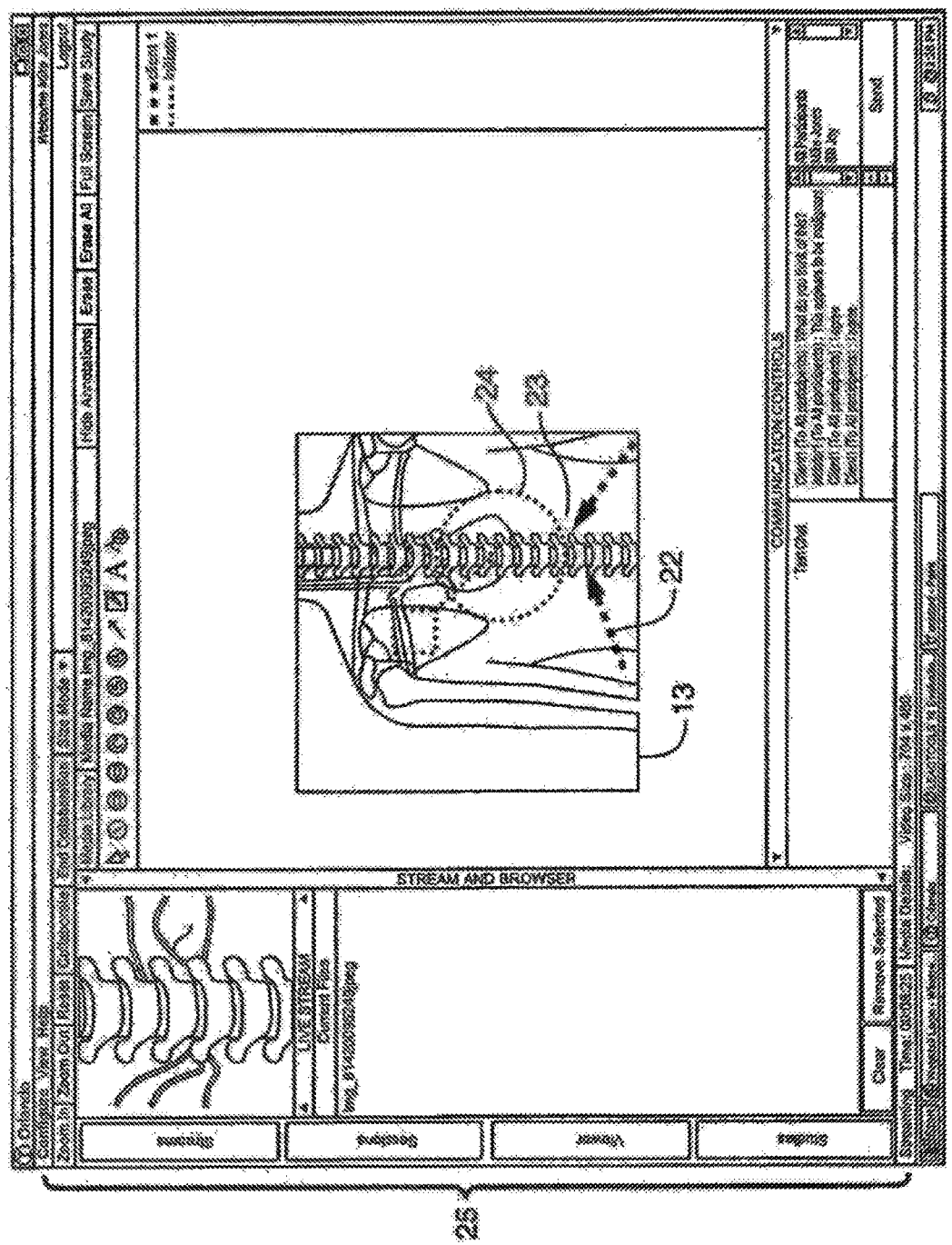
FIG. 7, depicts a graphic user interface screen shot of a cognitive collaboration session, including streaming medical imagery with annotations.
Figure 8:
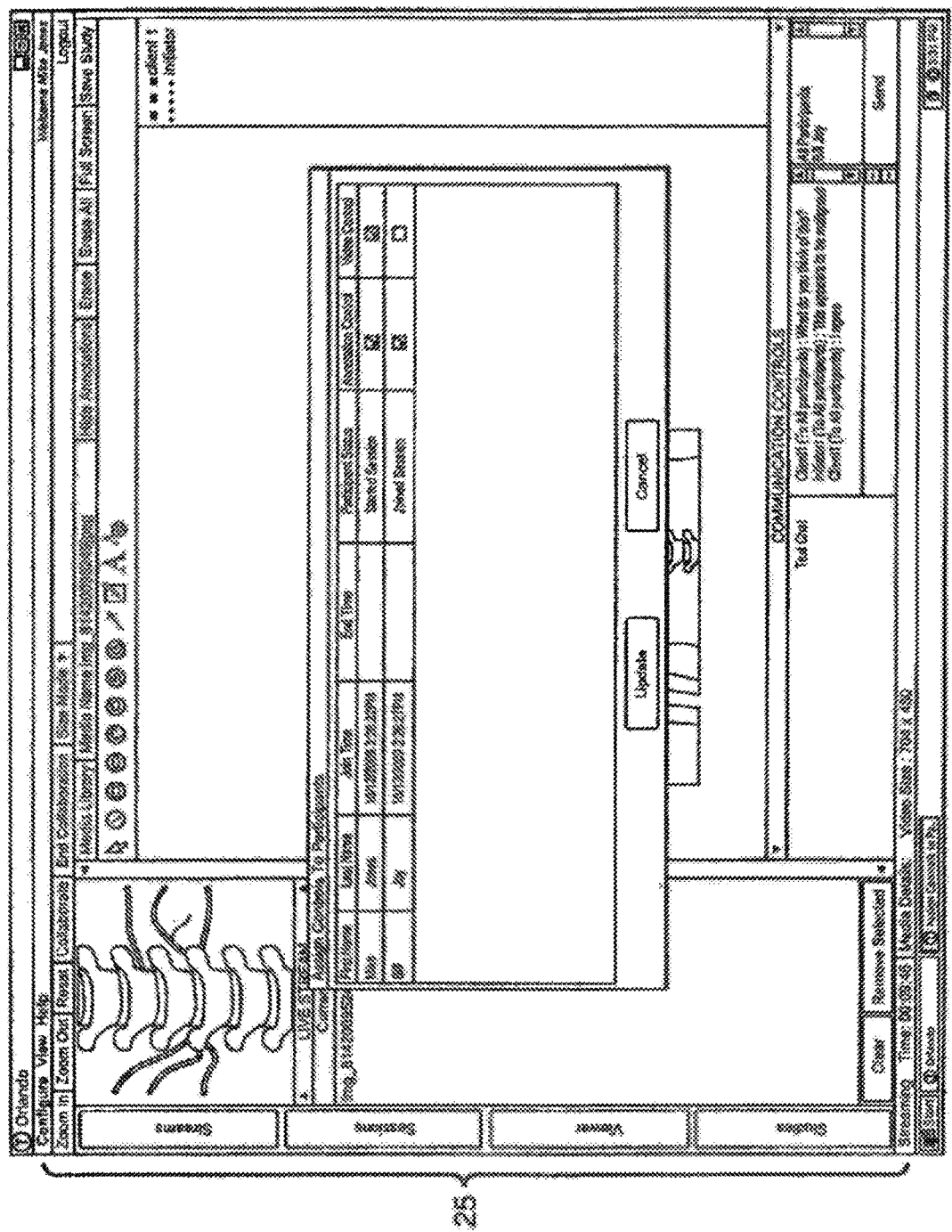
FIG. 8, depicts a graphic user interface screen shot of a cognitive collaborant workstation: client assignment of control to participant cognitive collaborant.
Figure 10:
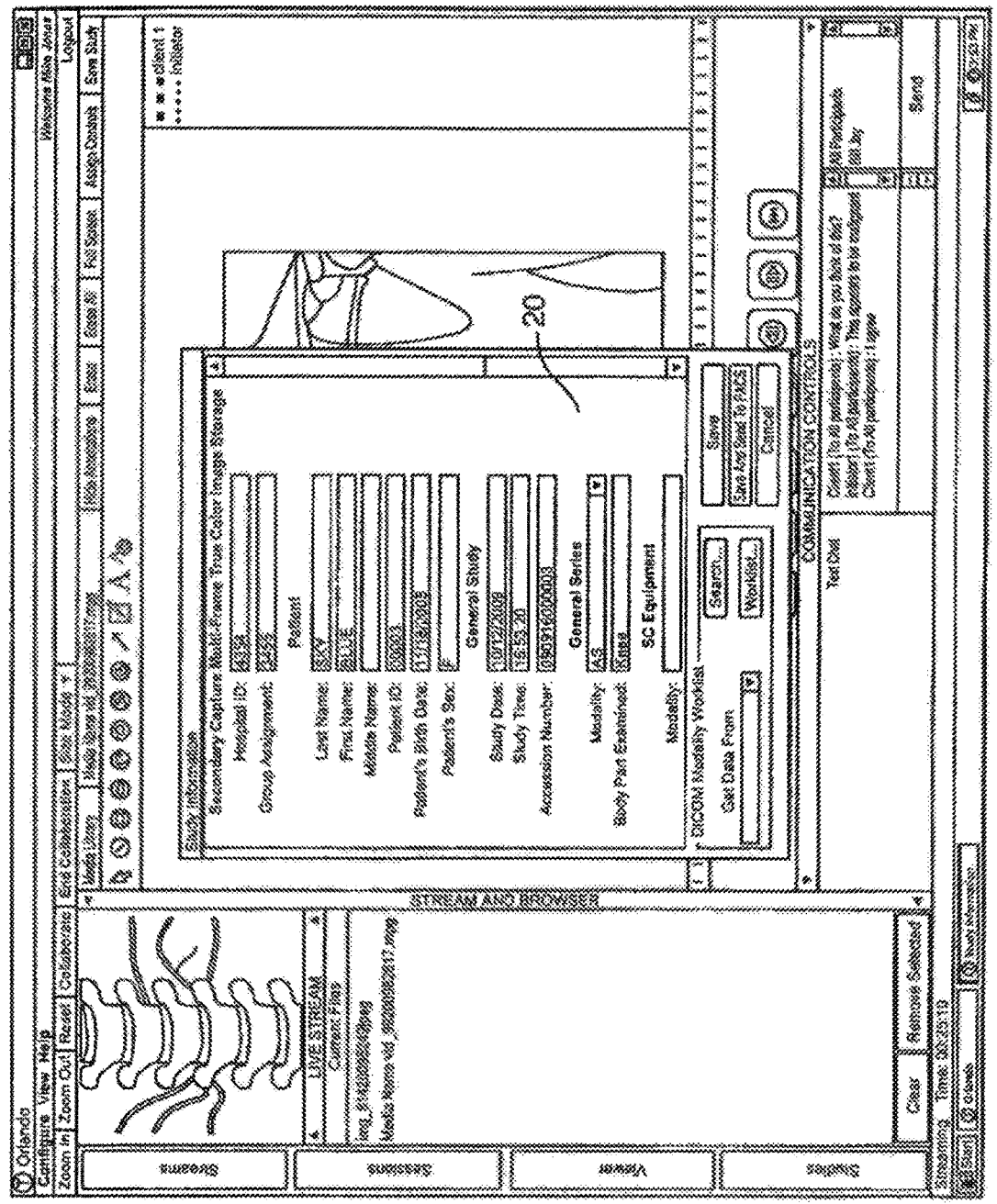
FIG. 10, depicts a graphic user interface screen shot of patient image study information.
Figure 11:
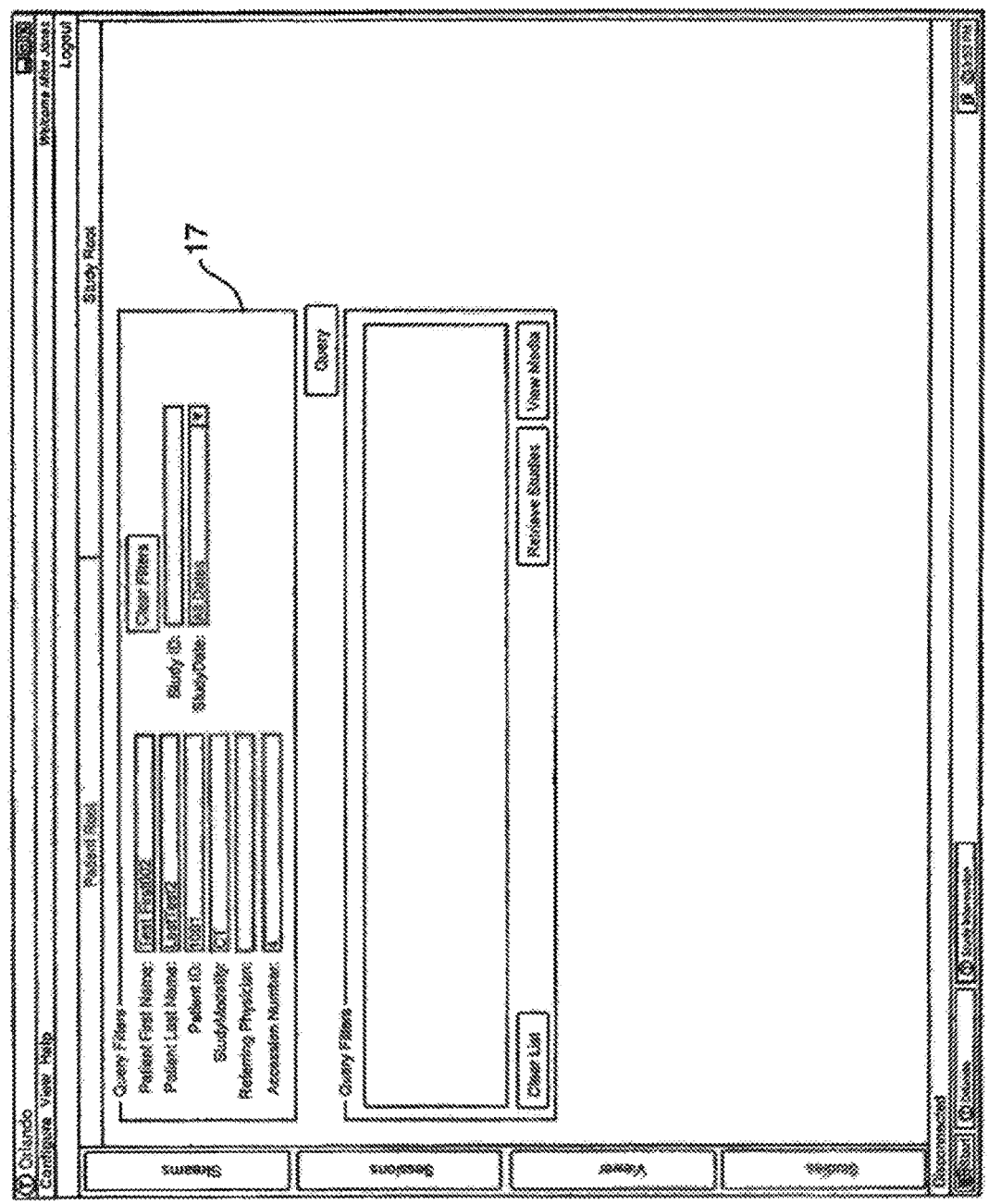
FIG. 11, depicts a graphic user interface screen shot of patient electronic medical record information.
Figure 12:
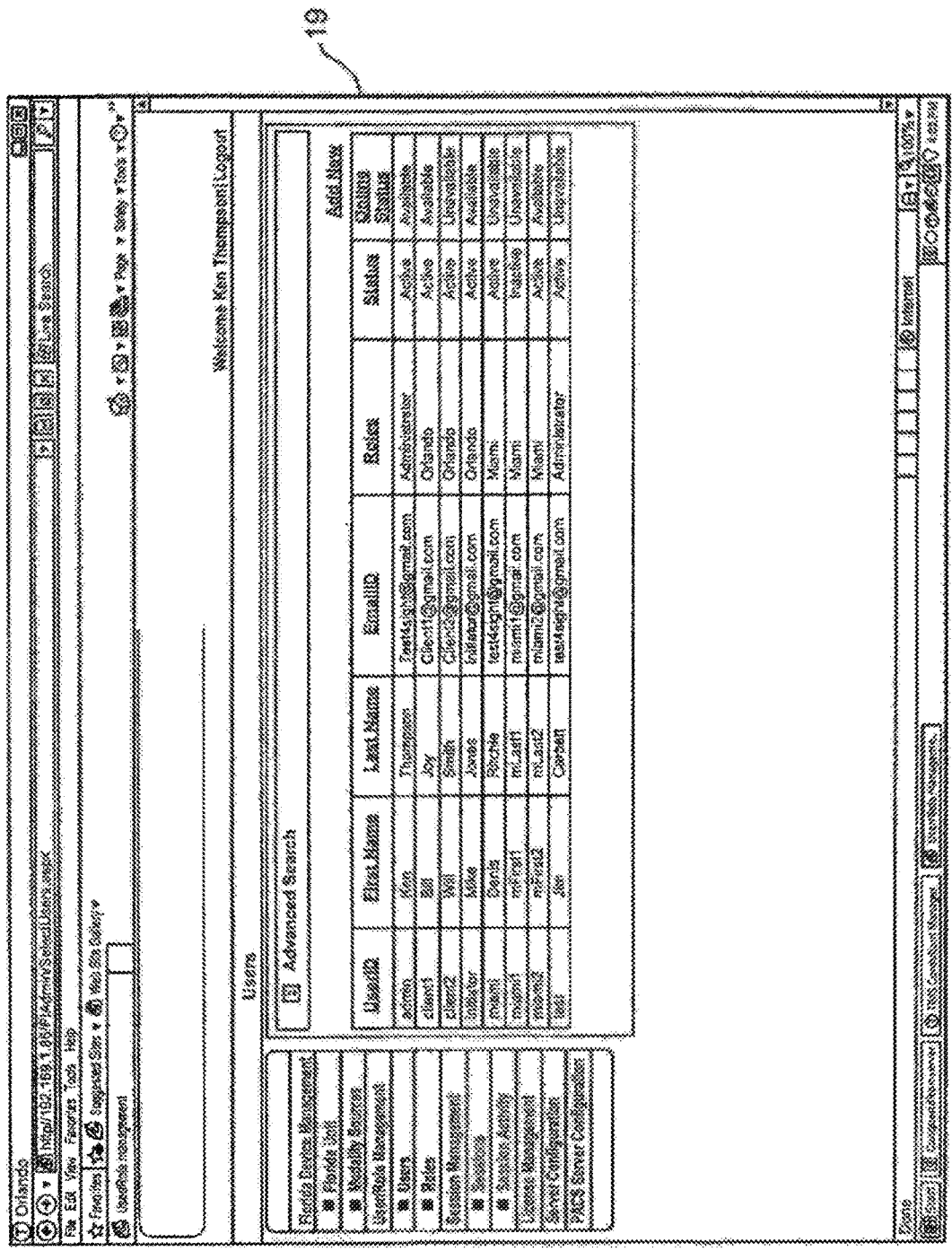
FIG. 12, depicts a graphic user interface screen shot of administrative controls.
Figure 13:
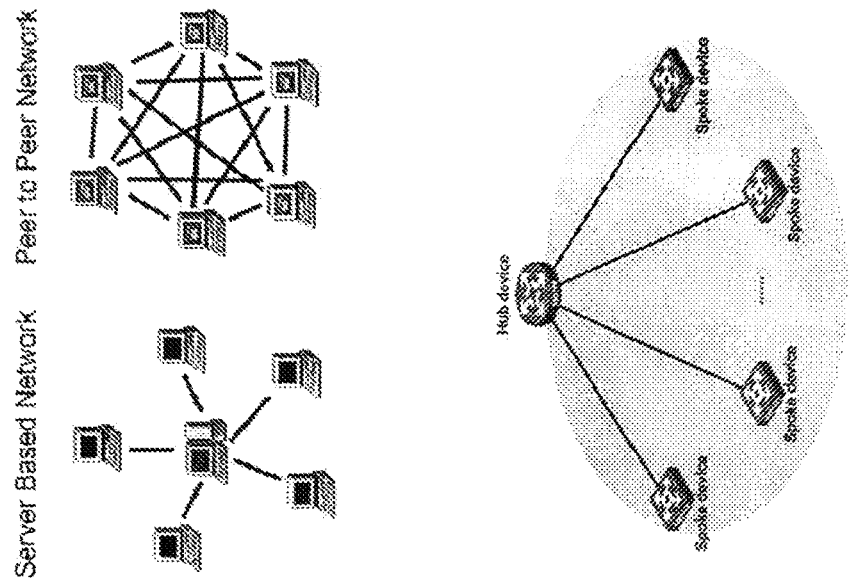
FIG. 13, depicts deployment of a hub-and-spoke device cluster for either server-based or peer-to-peer networks.
Figure 14:
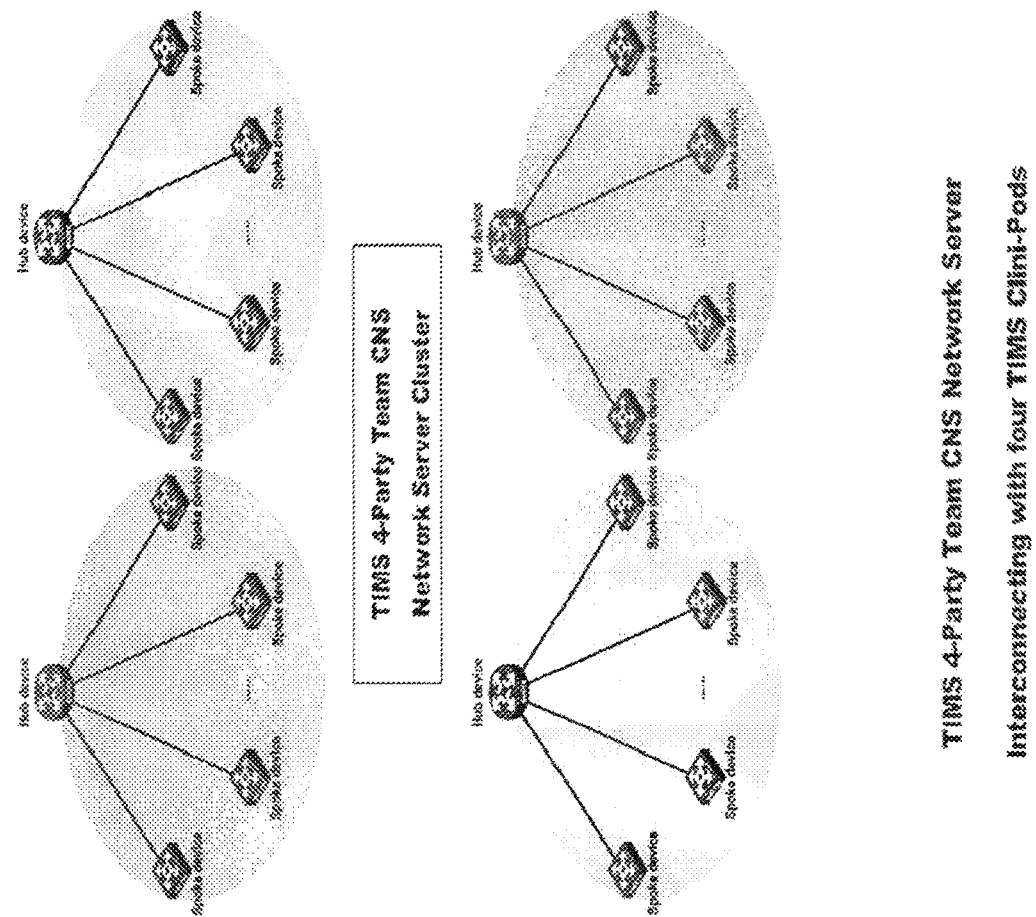
FIG. 14, depicts a 4-Party Team Network Server cluster interconnecting with four Clini-Pod hub-and-spoke device clusters.
Figure 15:
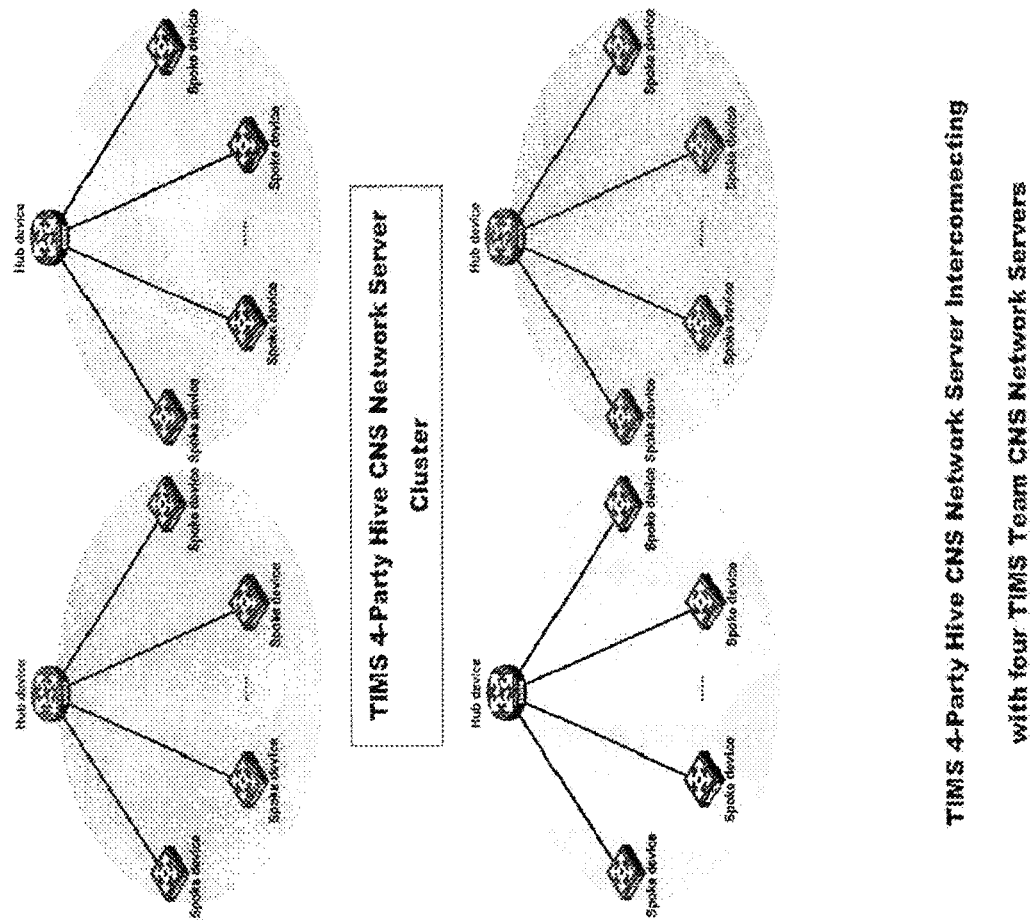
FIG. 15, depicts a 4-Party Hive Network Server cluster interconnecting with four Team Network Server clusters.
Figure 16:
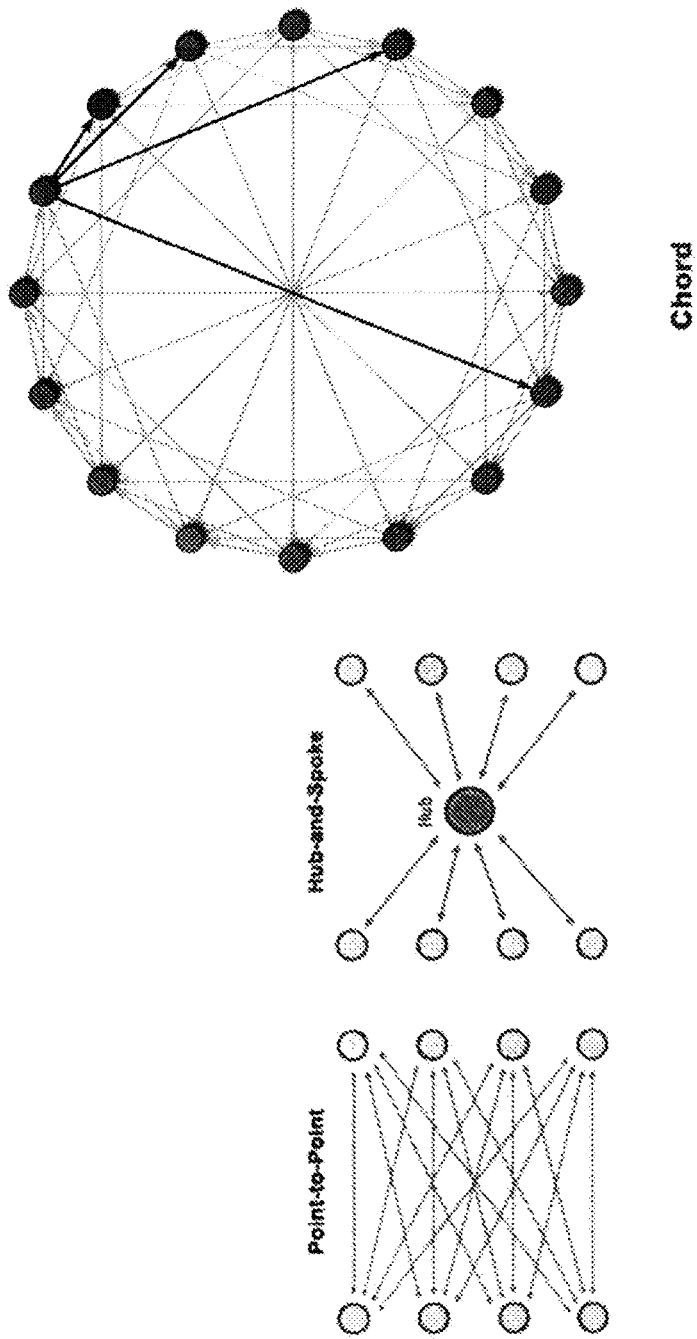
FIG. 16, depicts Alternative Network Architectures for Clini-Pod deployment: point-to-point vs hub-and-spoke vs chord.
Figure 17:
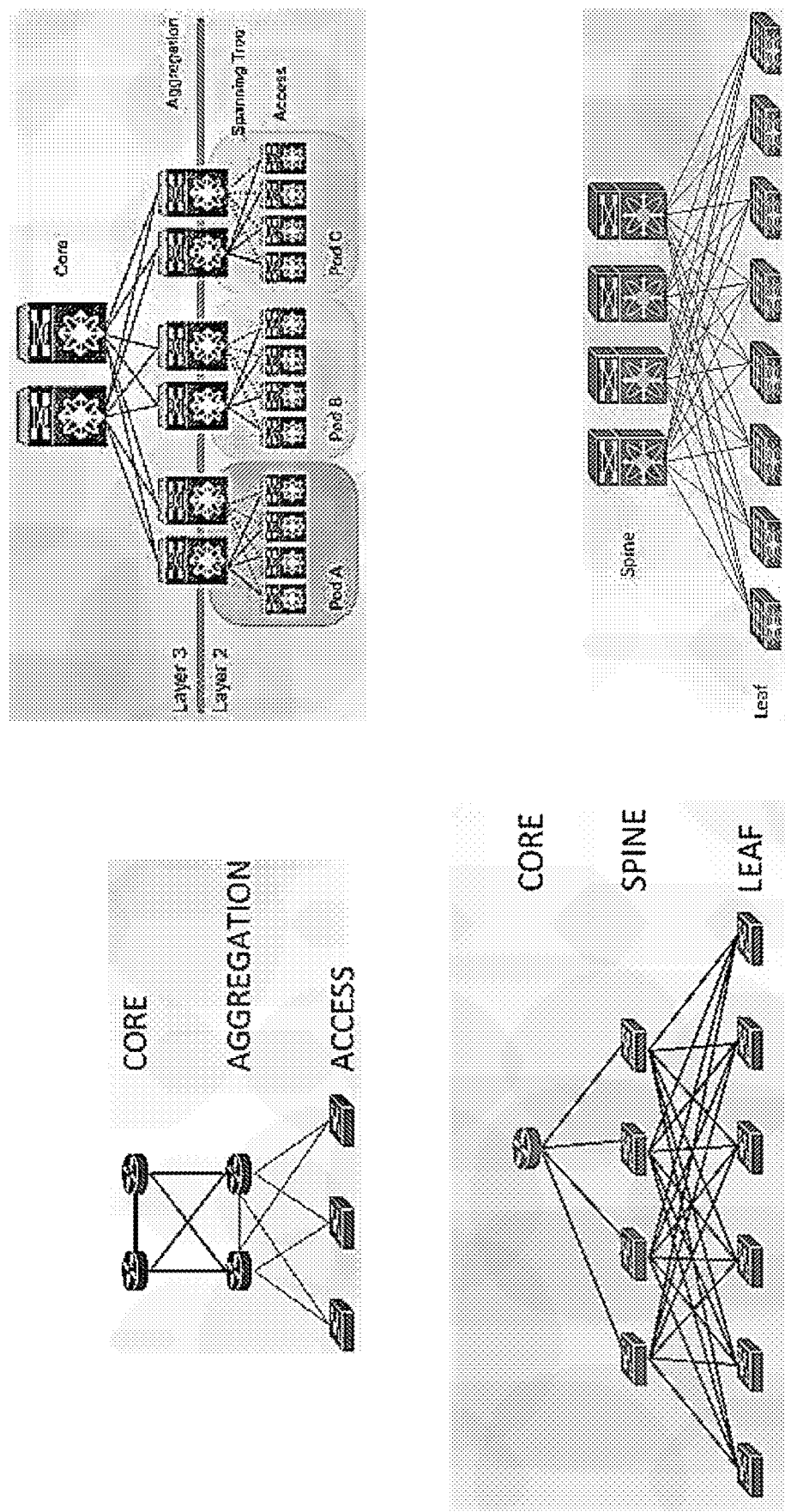
FIG. 17, depicts traditional 3-Tier Application Architectures versus Core-Spine-Leaf Network Topology.
Figure 18:
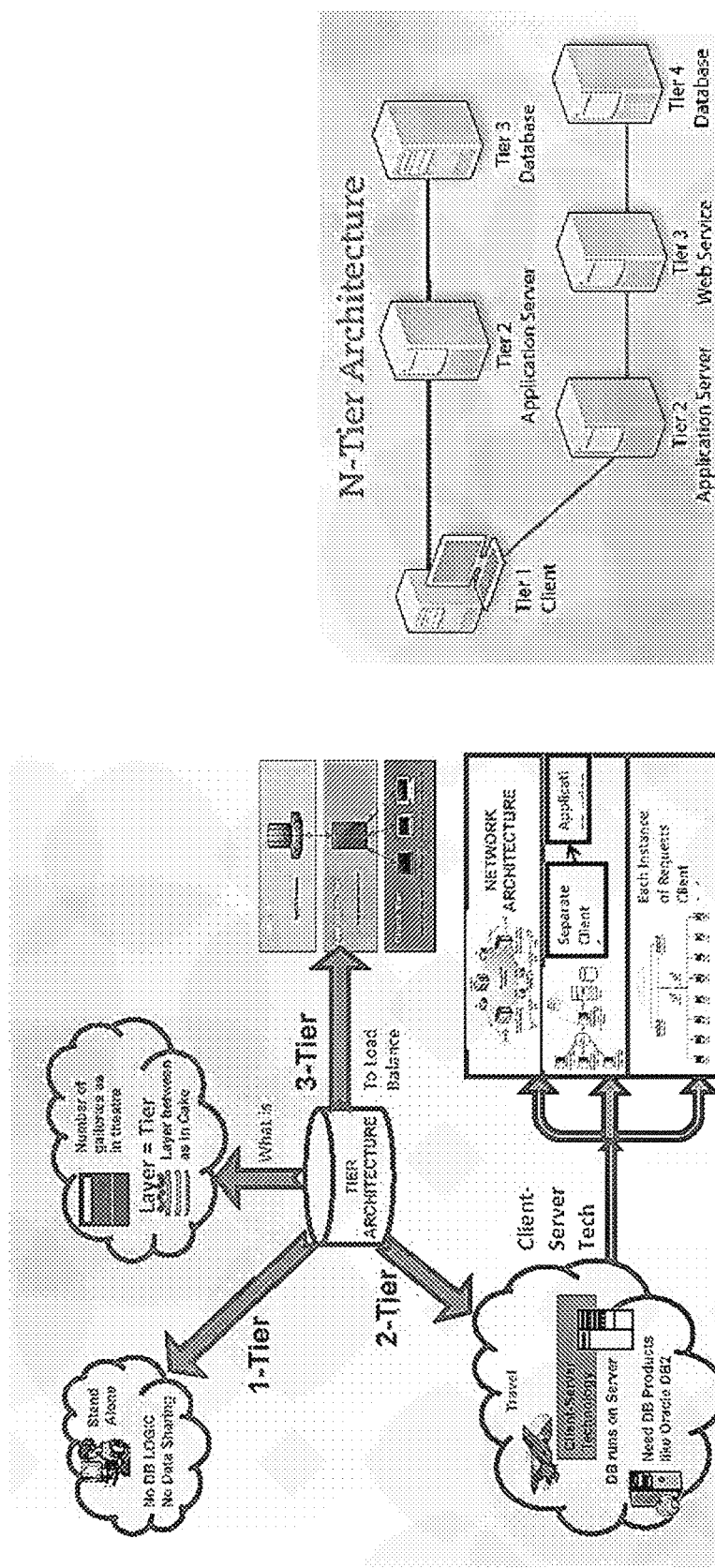
FIG. 18, depicts traditional 1-Tier, 2-Tier, 3-Tier and N-Tier Application Architectures.
Figure 19:
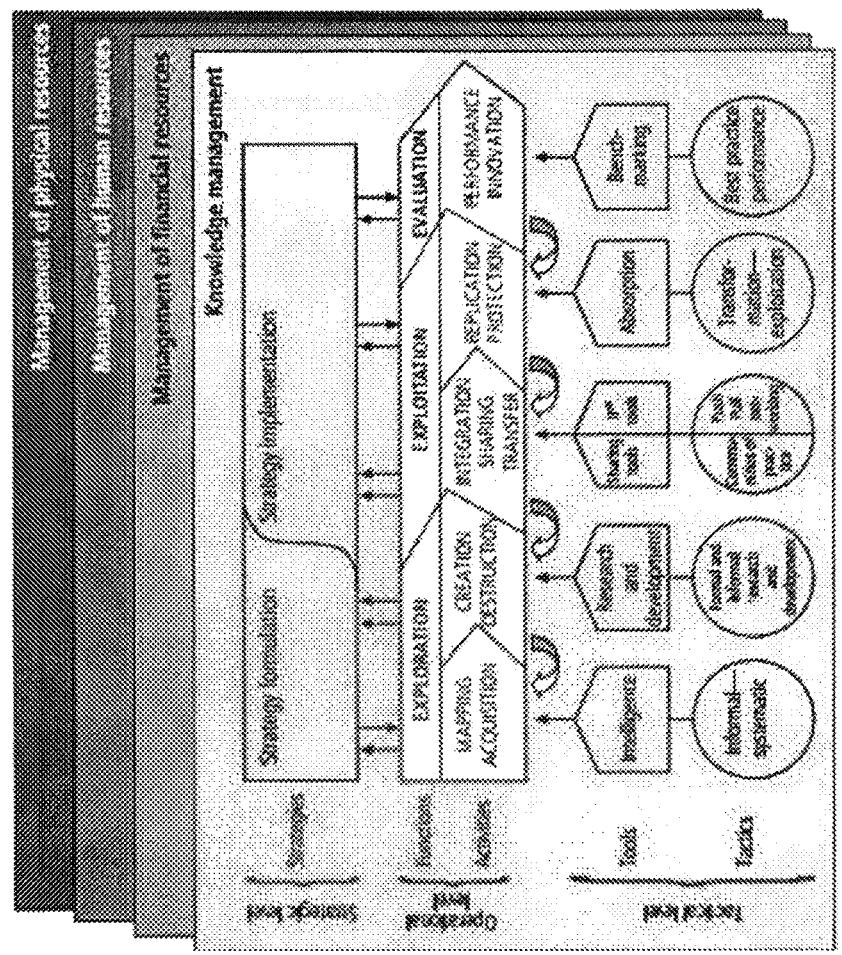
FIG. 19, depicts Value Chain Knowledge Exchange.
Figure 20:
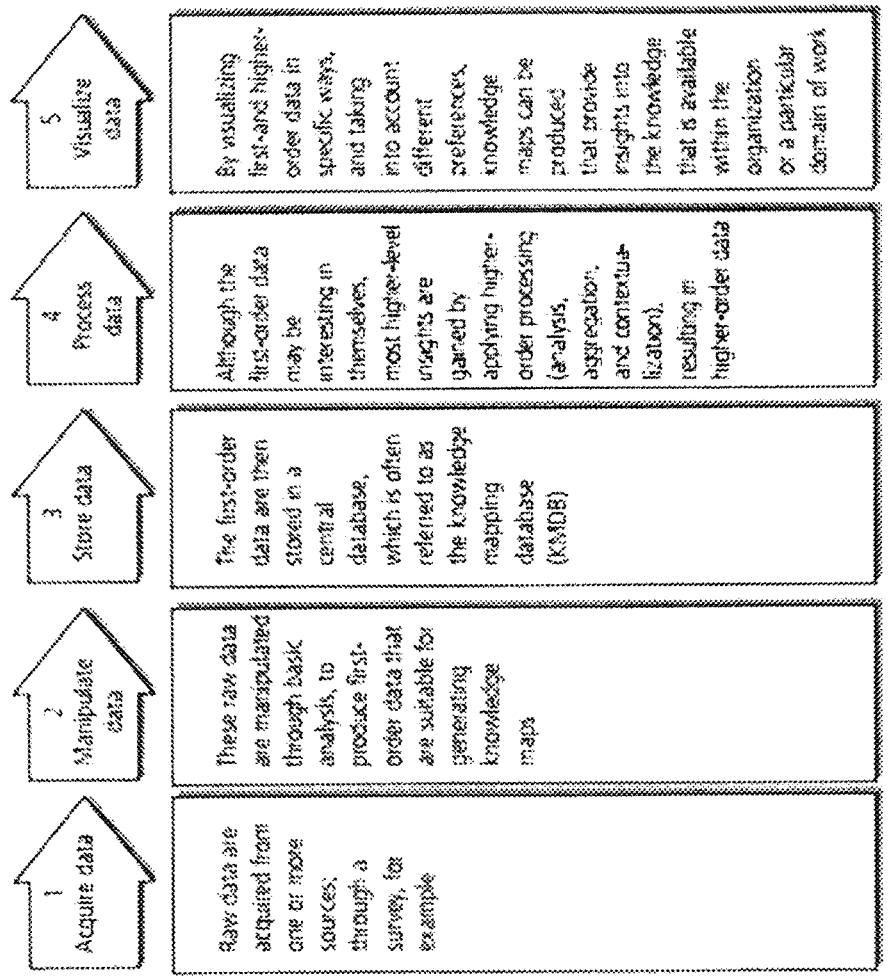
FIG. 20, depicts processes for generating insights from Knowledge Mapping and Interactive Data Visualization (data analytics, aggregation and contextualization).
Figure 21:
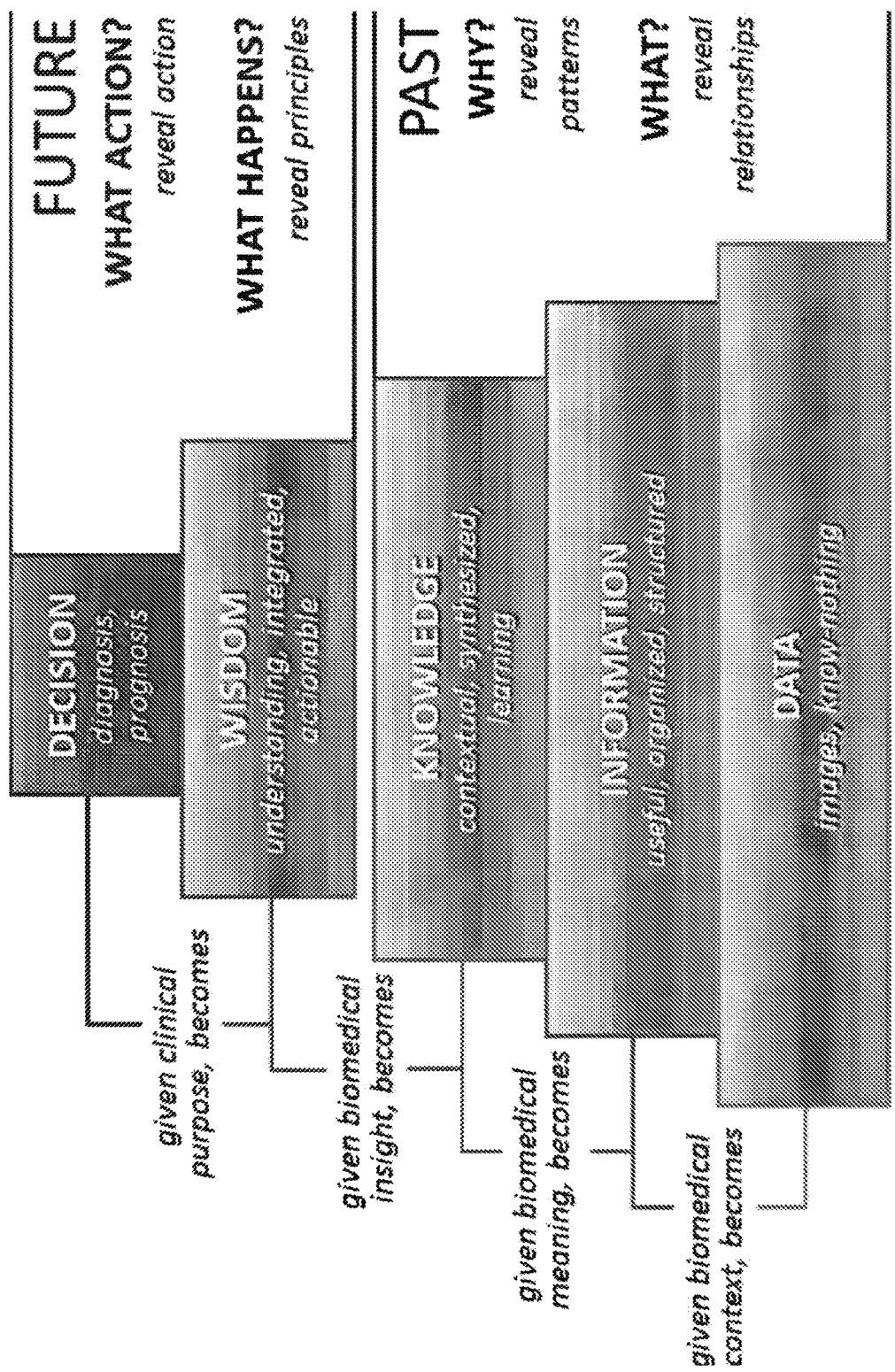
FIG. 21, depicts transforming Data into Information, then into Knowledge, Wisdom, Decision and Action.
Figure 22:
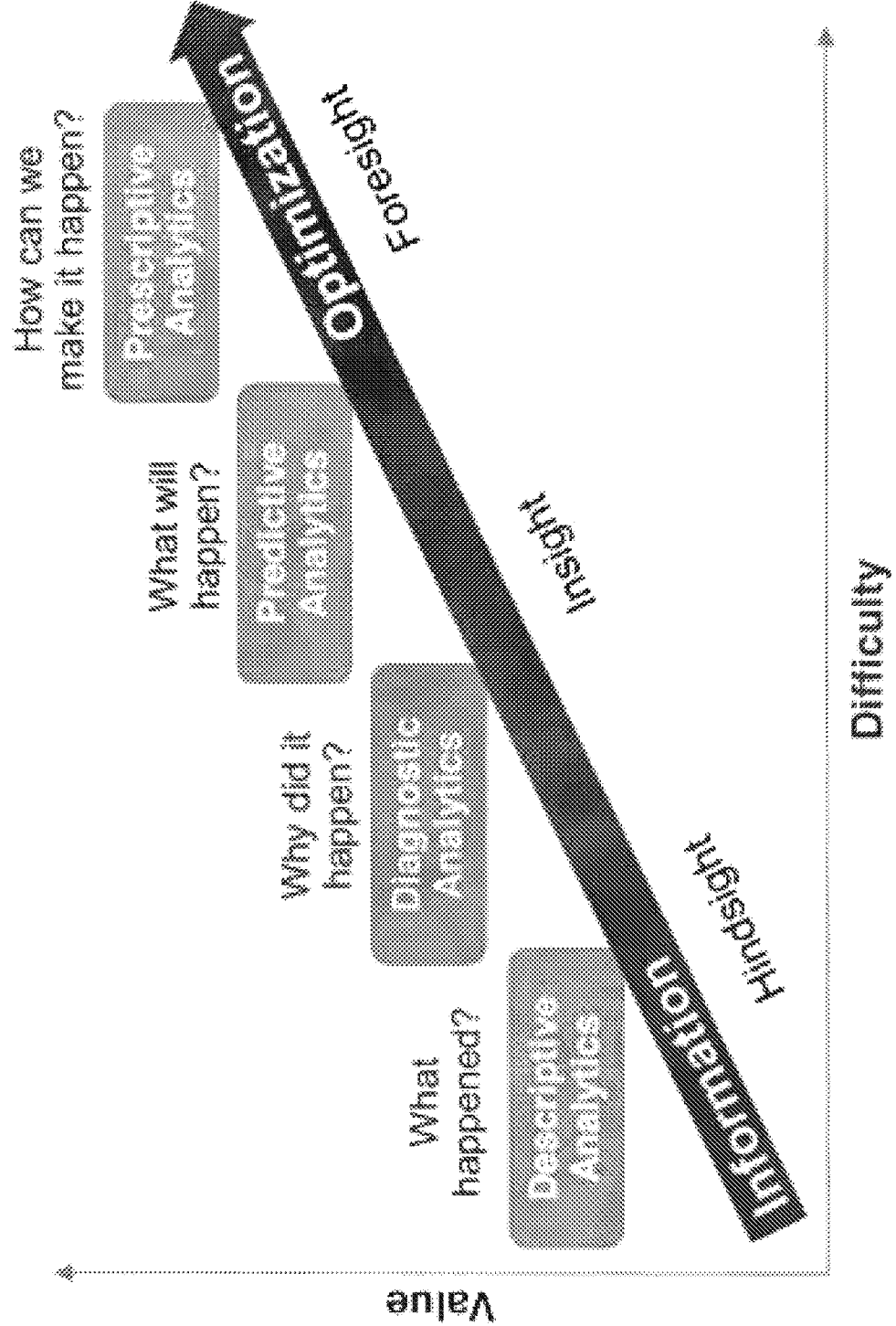
FIG. 22, depicts Information Optimization through Descriptive, Diagnostic, Predictive and Prescriptive Analytics.
Figure 23:
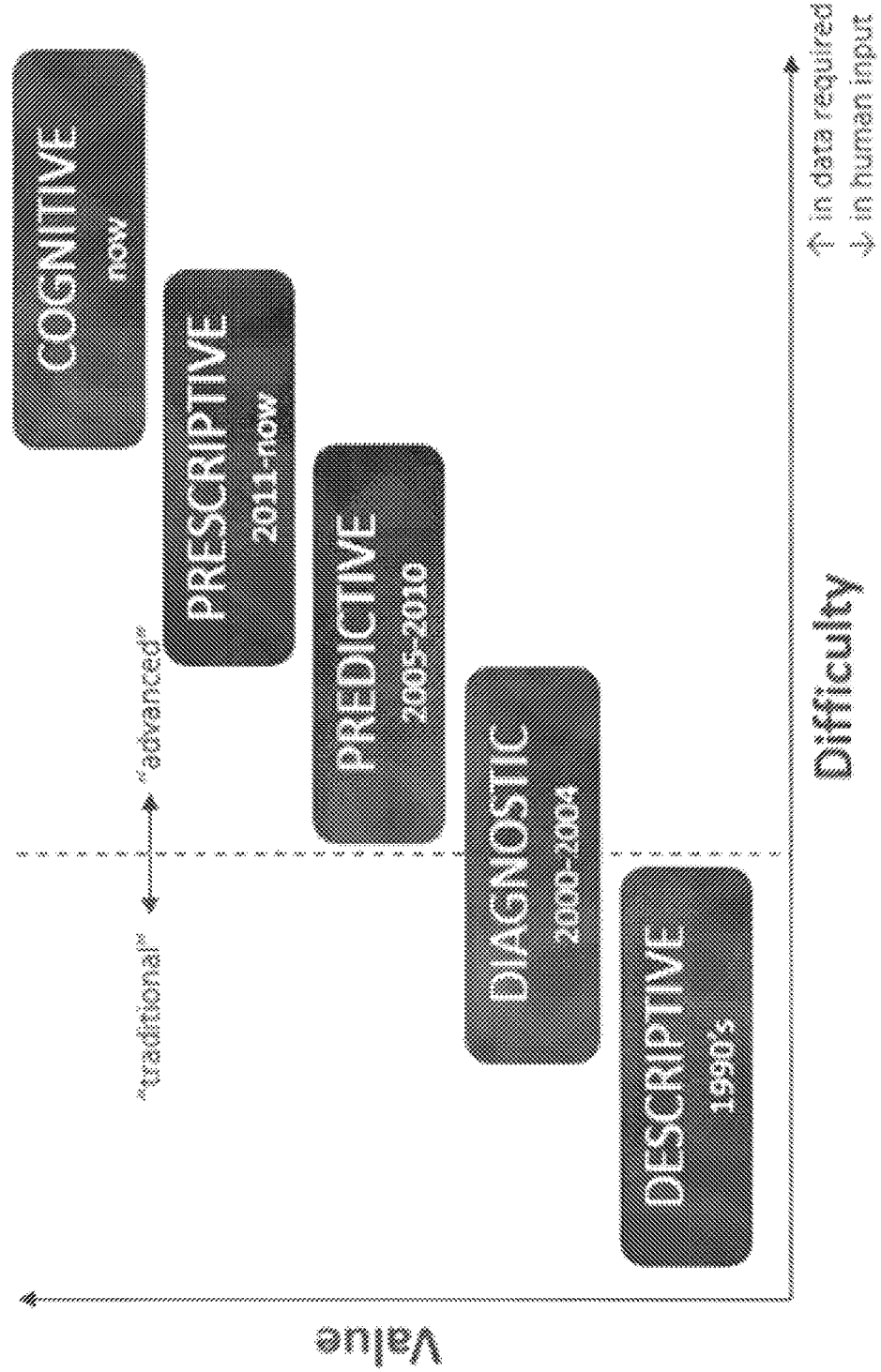
FIG. 23, depicts Cognitive Value Creation with Information Optimization and Advanced Data Analytics.
Figure 24:
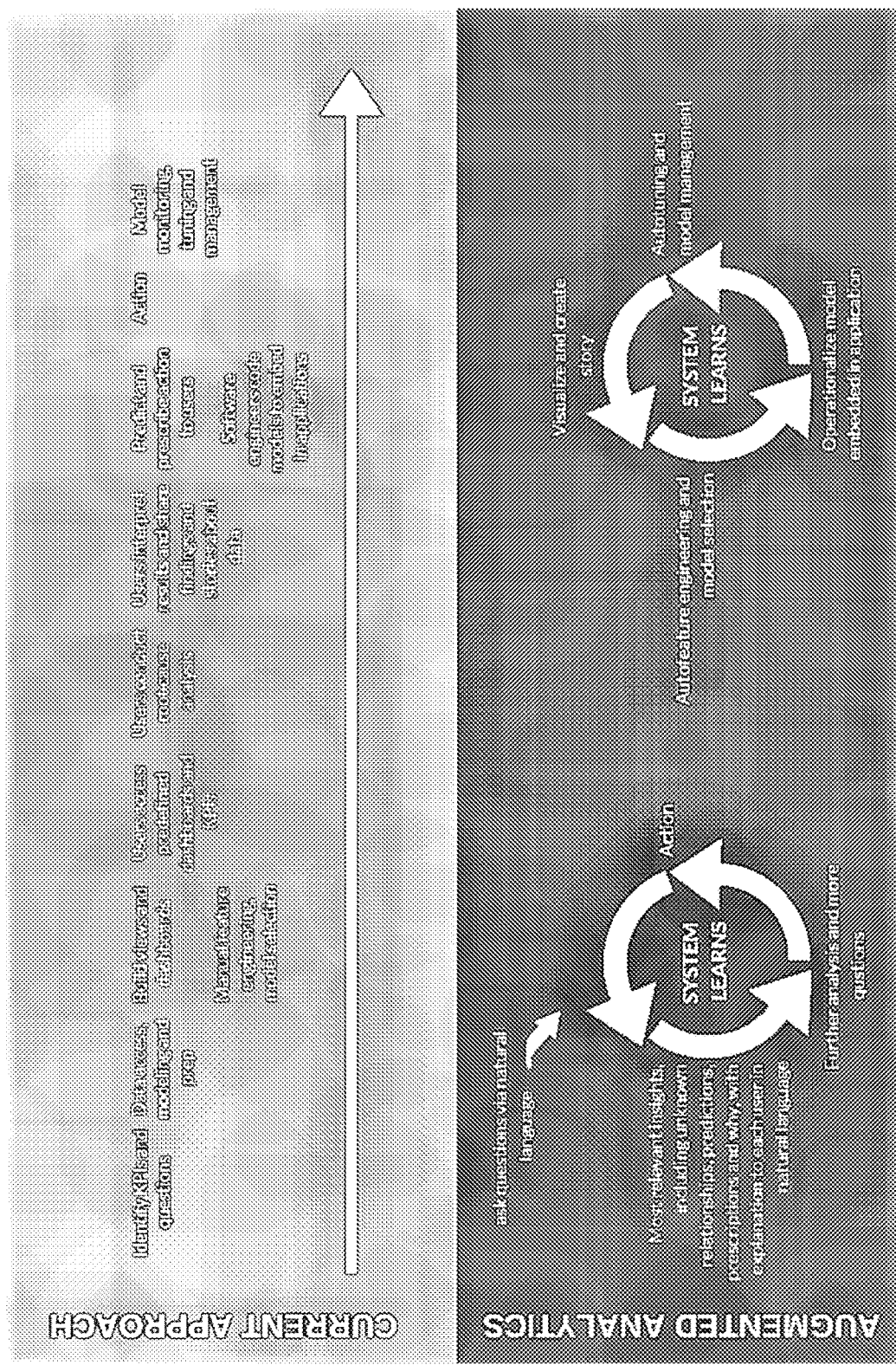
FIG. 24, depicts Adaptive Systems Learning with Augmented Analytics.
Figure 25:
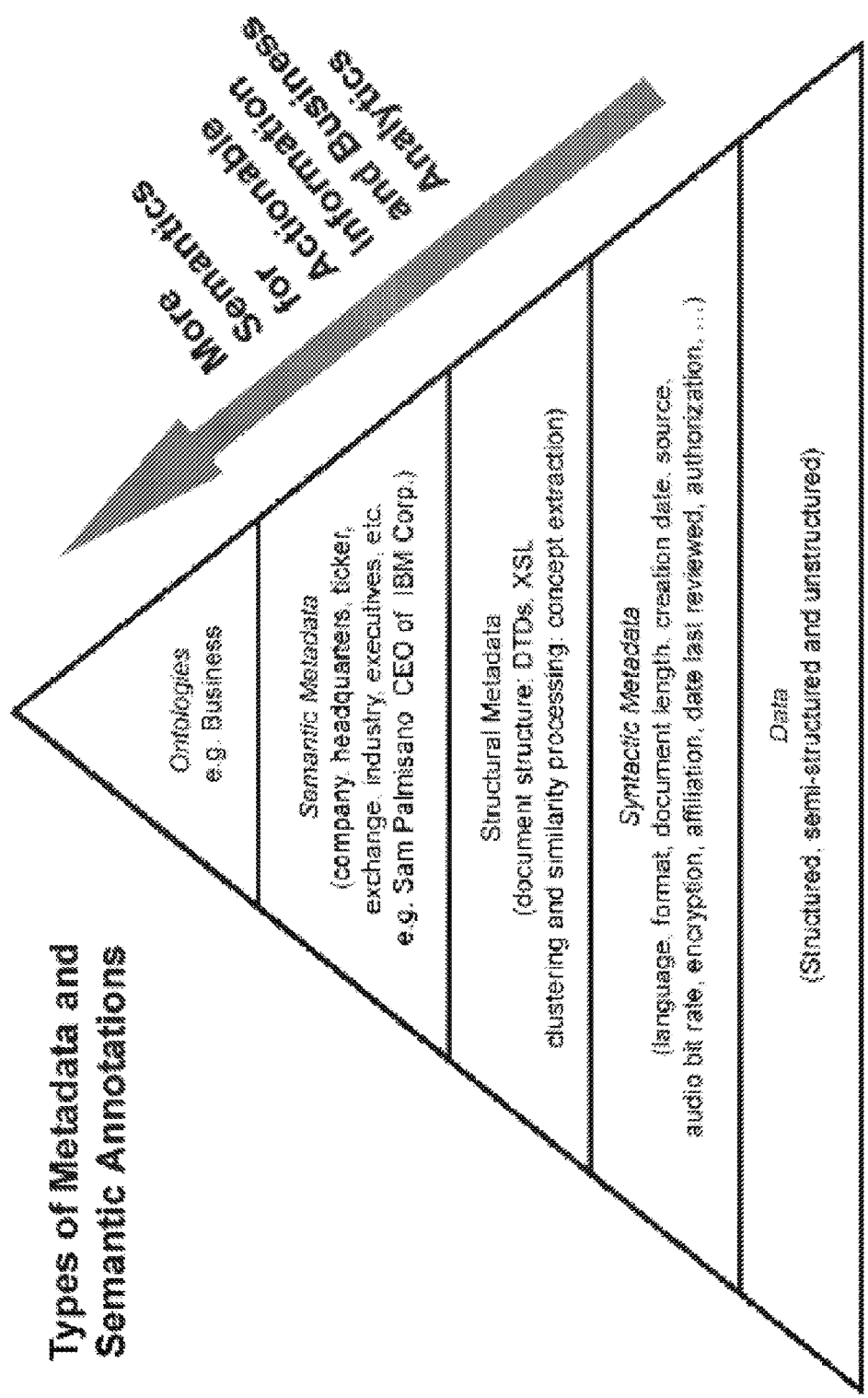
FIG. 25, depicts increasing Business Intelligence and Actionable Information with semantic metadata and annotation.
Figure 26:
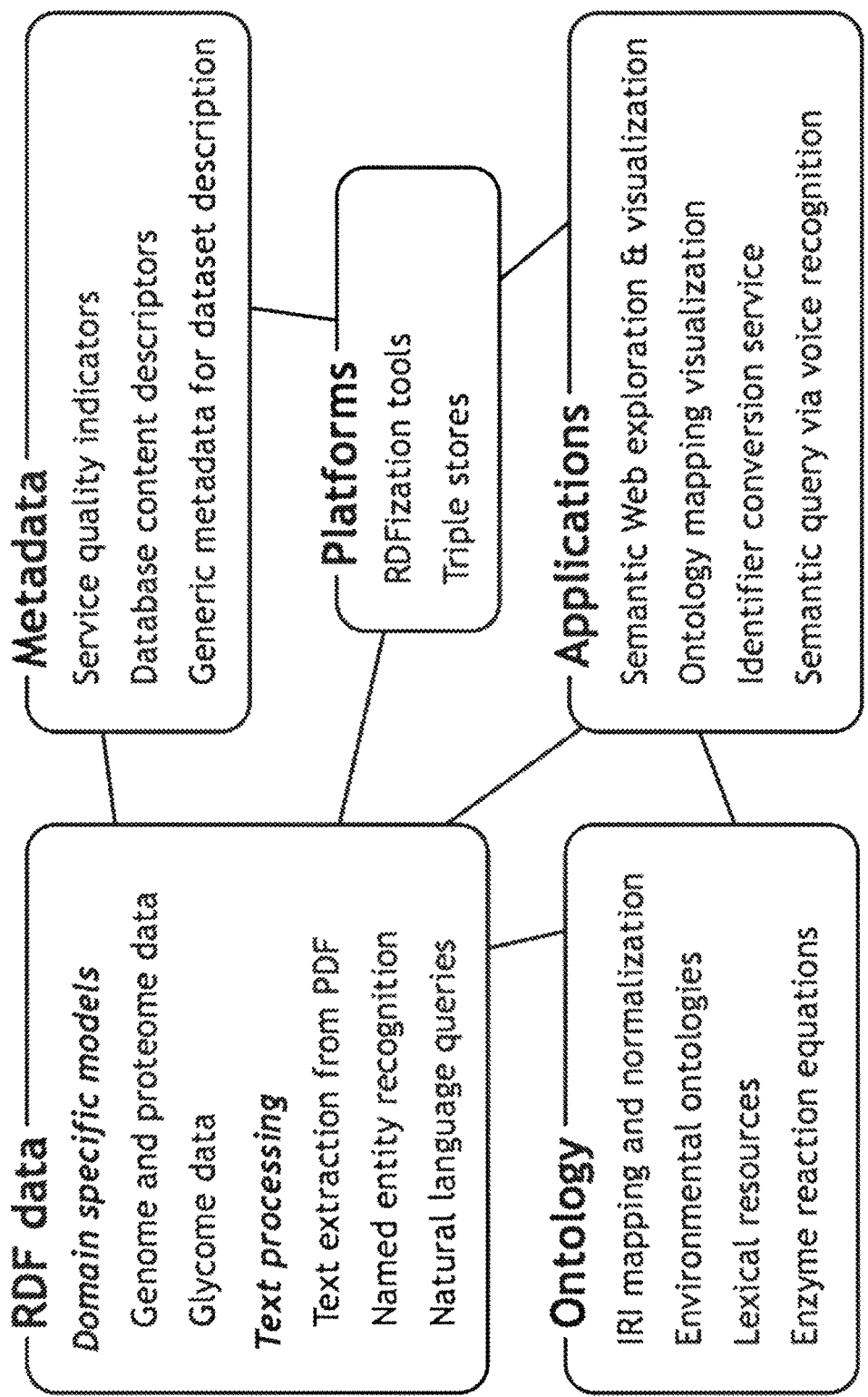
FIG. 26, depicts domain-specific semantic search, ontology mapping and visualization with RDF metadata.
Figure 27:
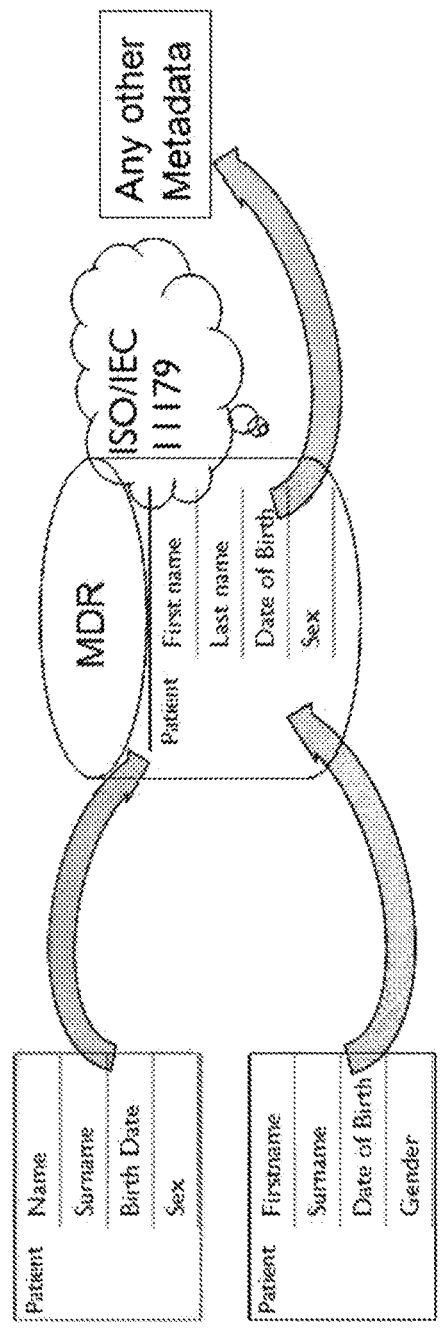
FIG. 27, depicts semantic interoperability with metadata registries and information model annotation.
Figure 28:
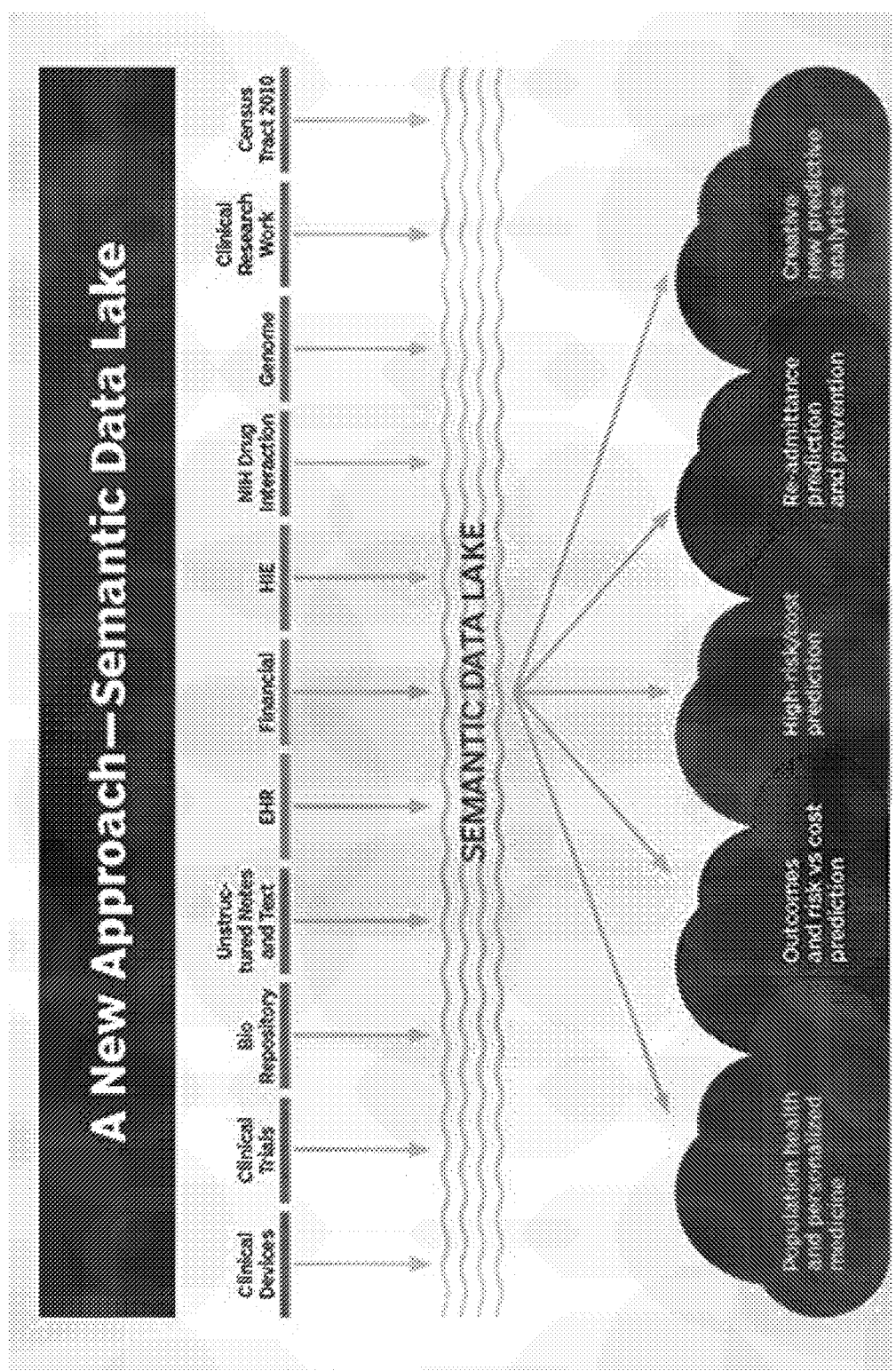
FIG. 28, depicts a semantic data lake for clinical, financial and outcomes data integration.
Figure 30:
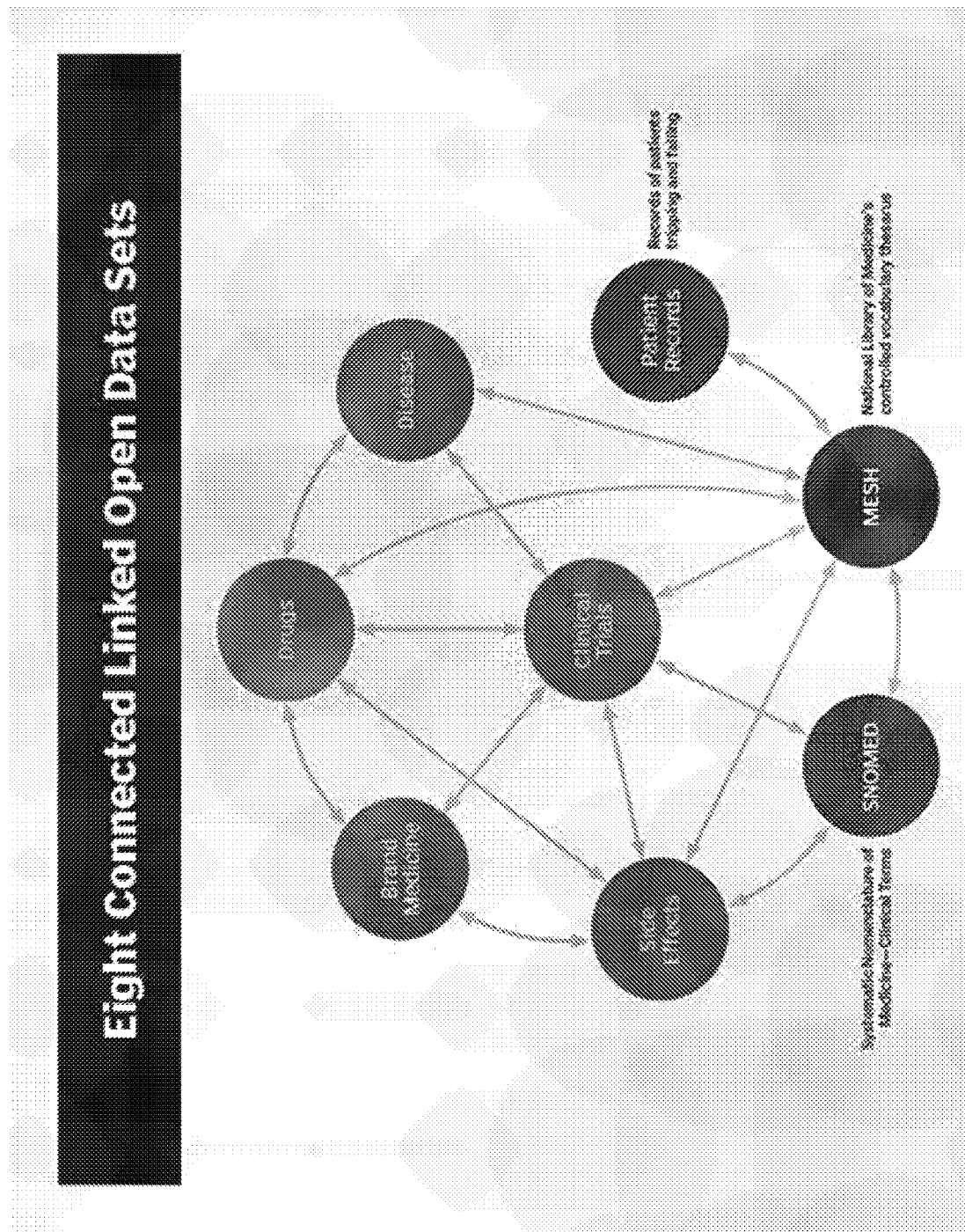
FIG. 30, depicts semantic metadata linking open and proprietary pharmaceutical data sets for clinical trials management.
Figure 31:
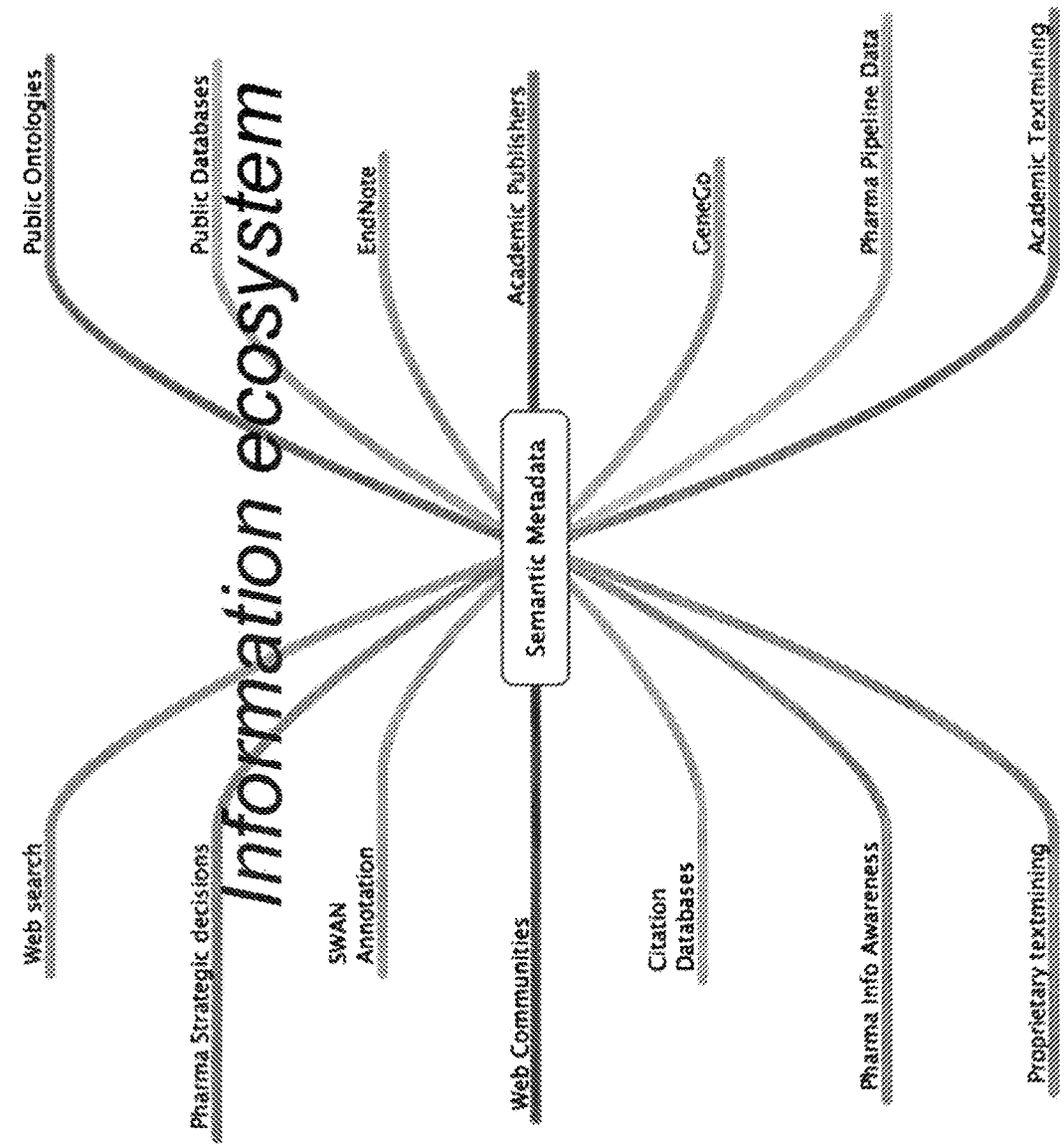
FIG. 31, depicts semantic metadata connecting an information ecosystem with open and proprietary clinical data sets for pharmaceutical development and pipeline management.
Figure 32:
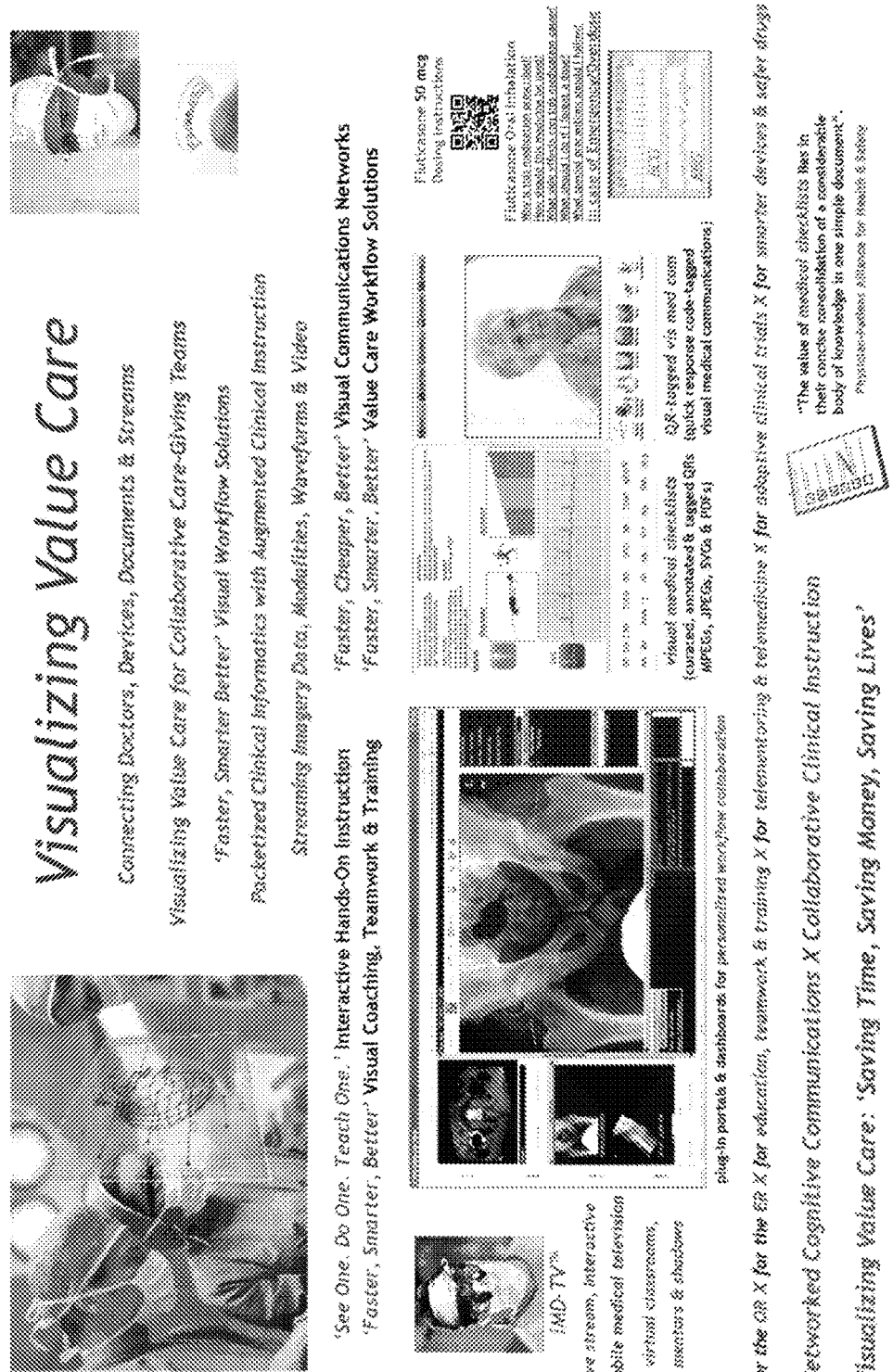
FIG. 32, depicts Visualizing Value Care: Connecting Doctors, Devices, Documents and Streams—Visualizing Value Care for Collaborative Care-Giving Teams.
Figure 33:
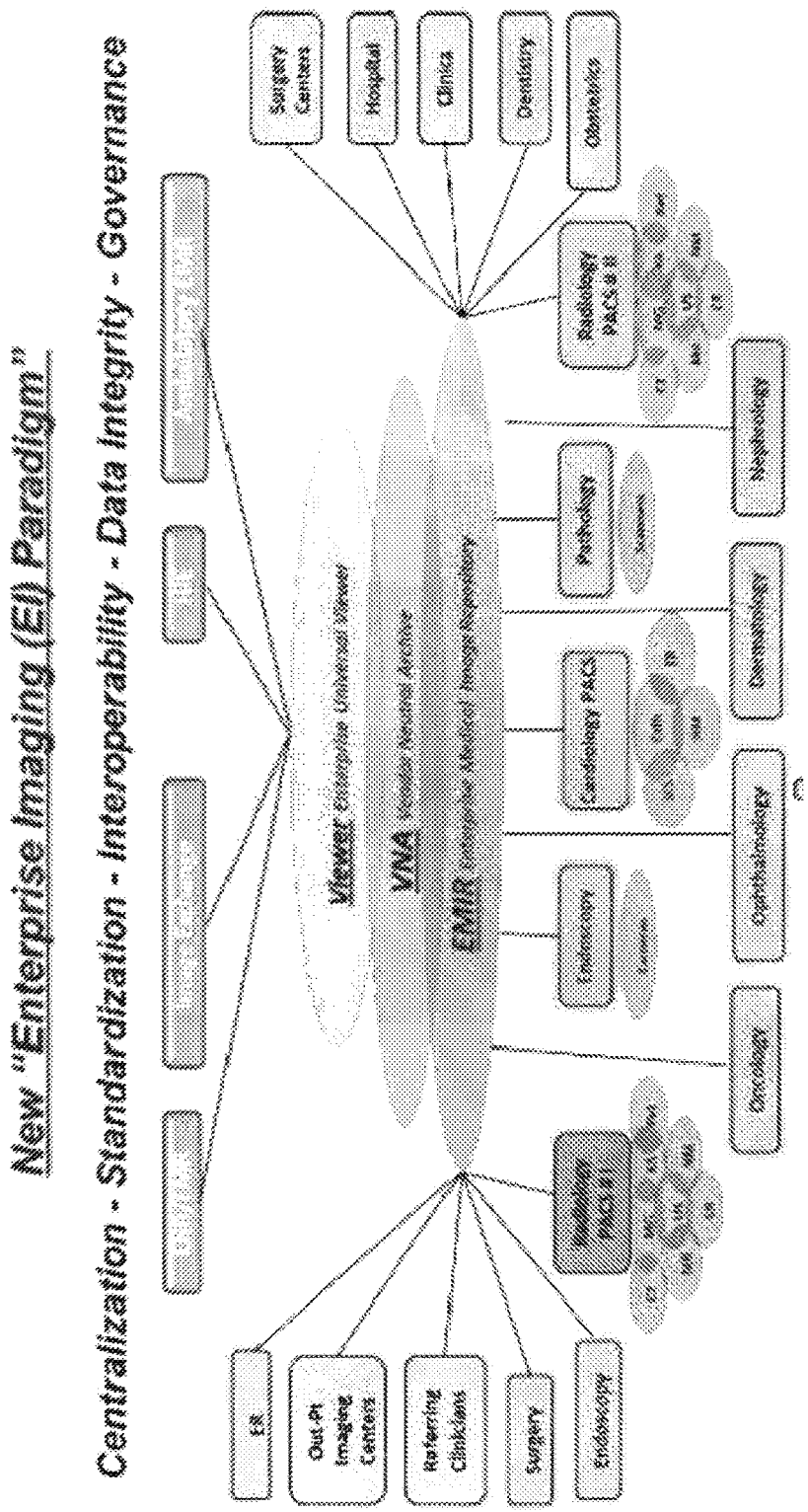
FIG. 33, depicts a New Paradigm for Collaborative Value Care with Cognitively-enriched Enterprise Imaging.
Figure 34:
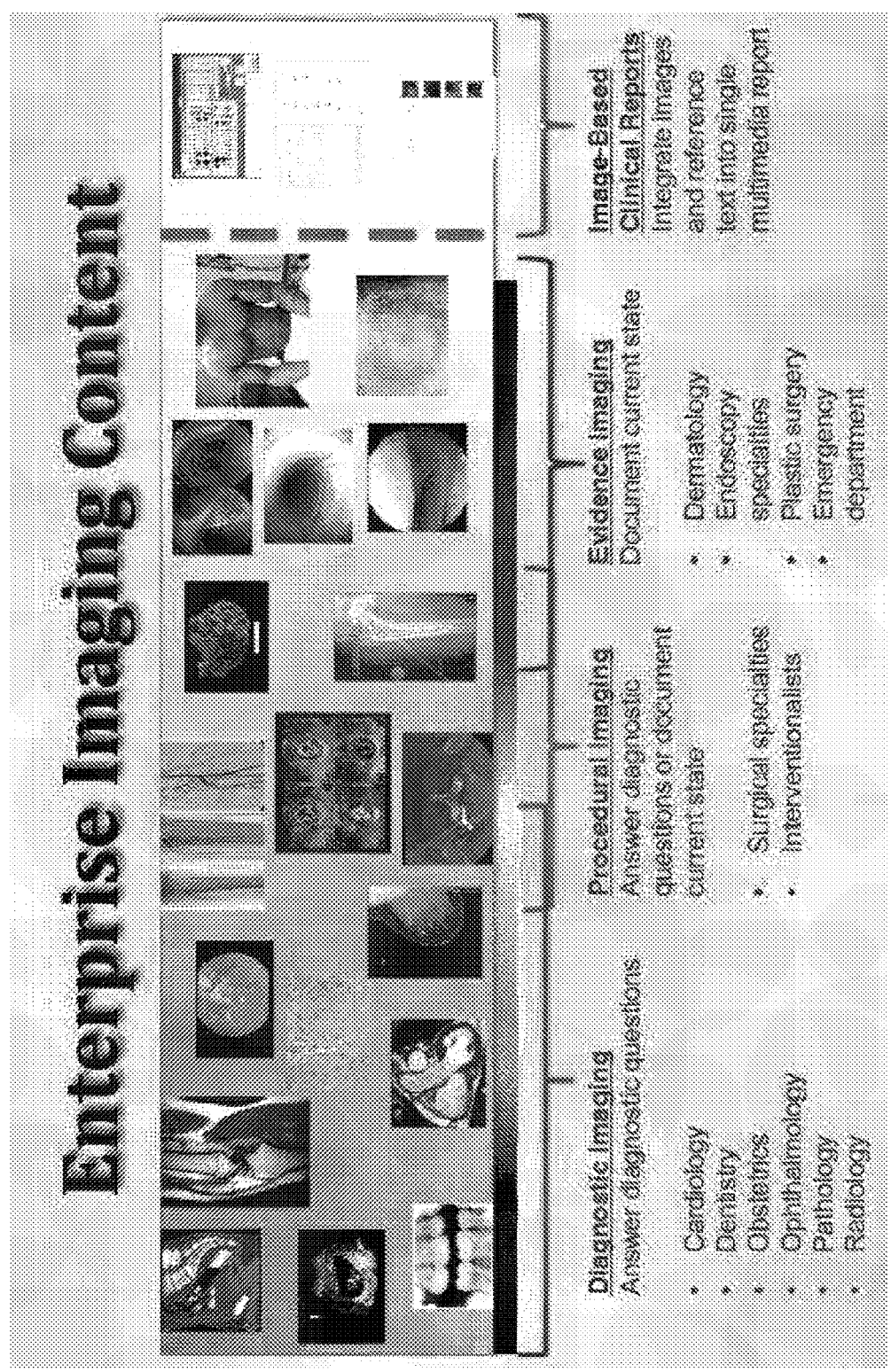
FIG. 34, depicts Cognitively-enriched Enterprise Imaging: Diagnostic, Procedural and Evidence Imaging, along with Imaged-Based Clinical Reports.
Figure 35:
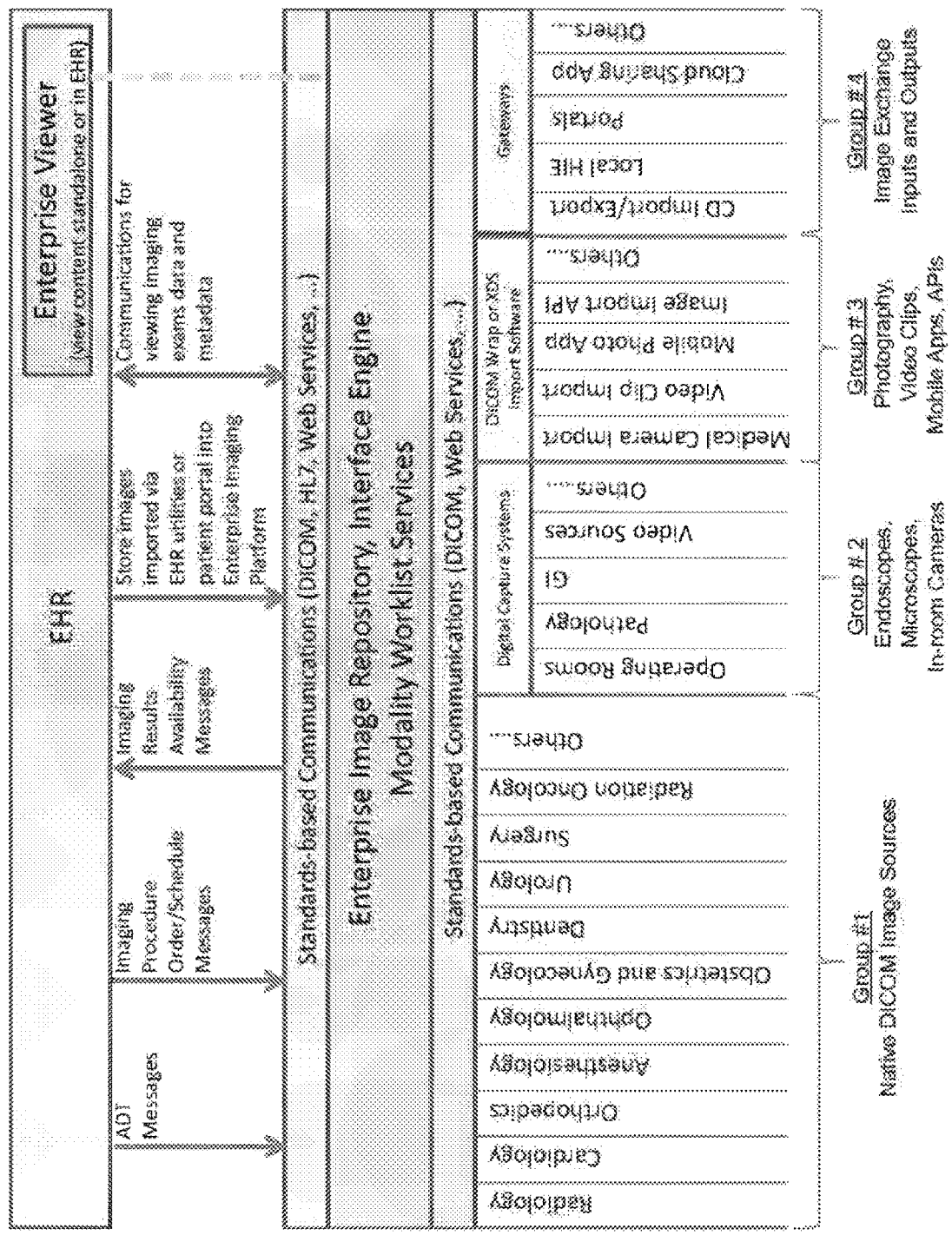
FIG. 35, depicts Cognitively-enriched Enterprise Imaging Repository Information Architecture.
Figure 36:
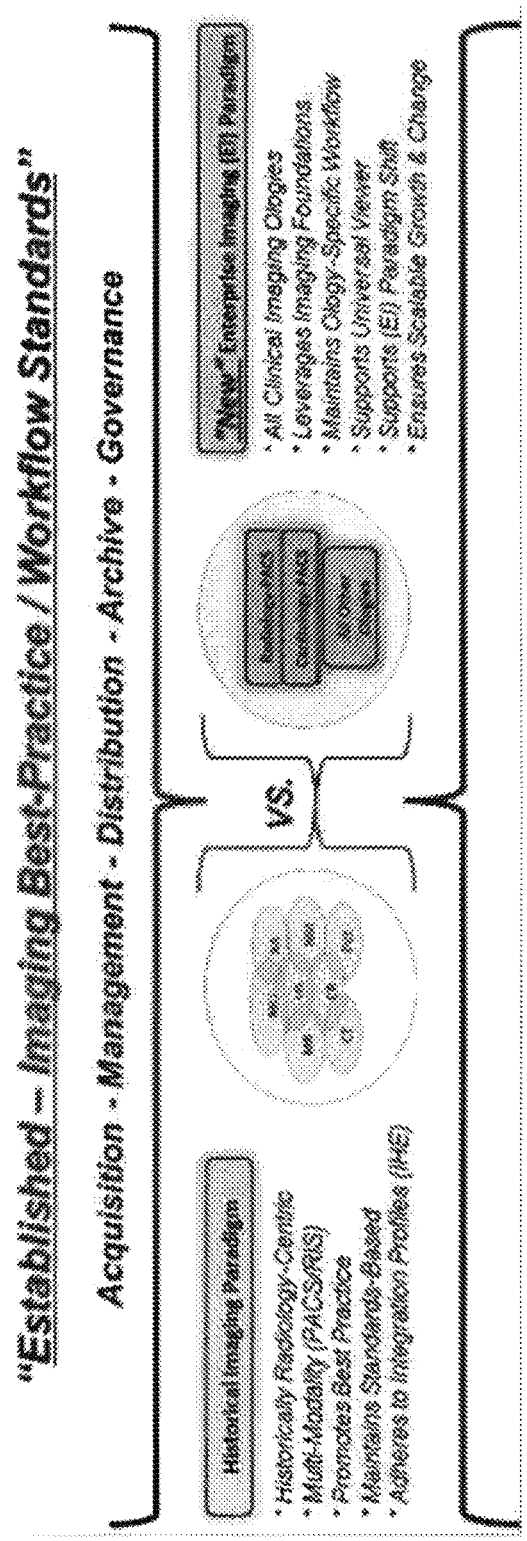
FIG. 36, depicts Cognitively-enriched Enterprise Imaging—Best Practices Workflow.
Figure 37:
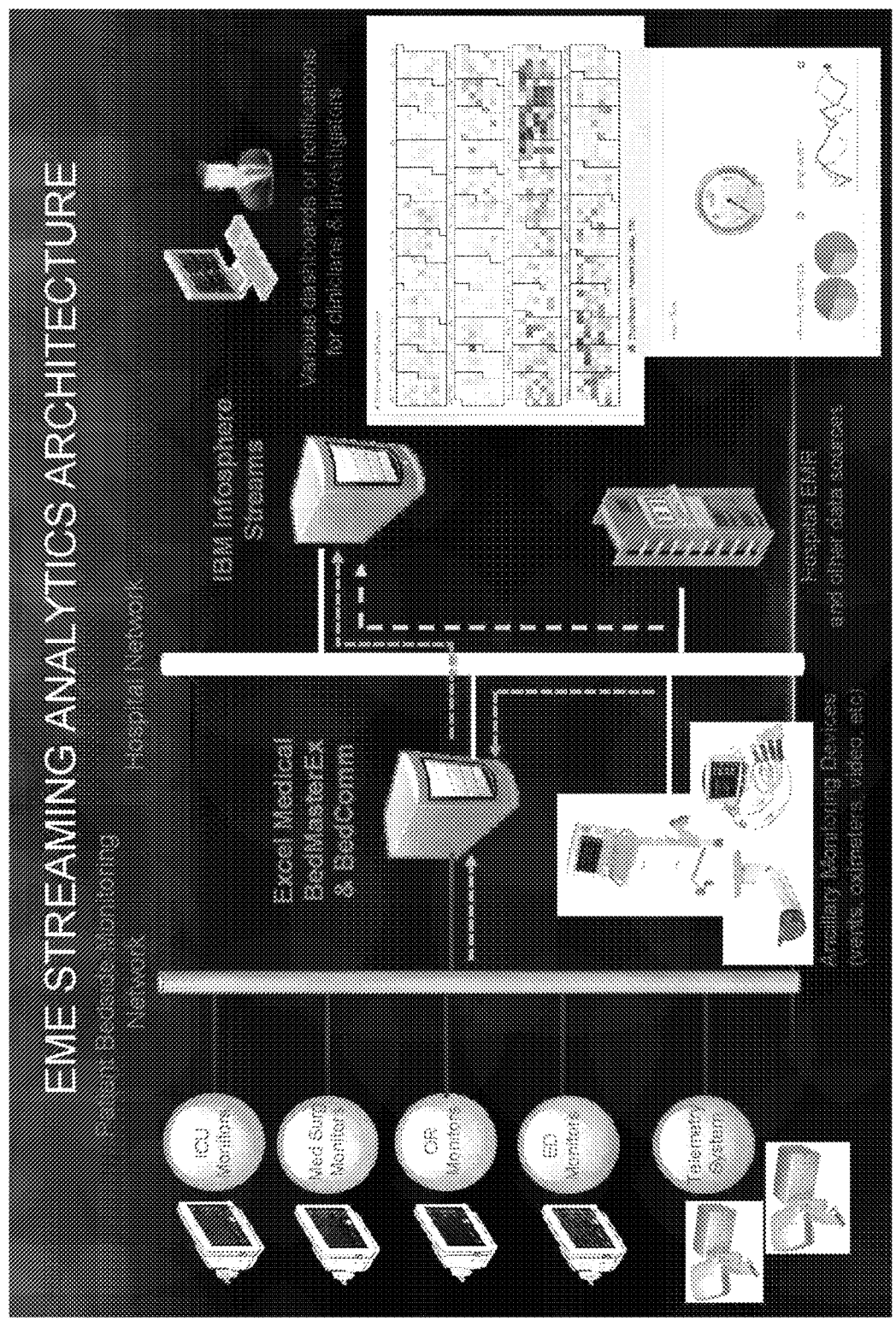
FIG. 37, depicts Streaming Analytics Architecture for Hospital-based Enterprise Imaging.
Figure 38:
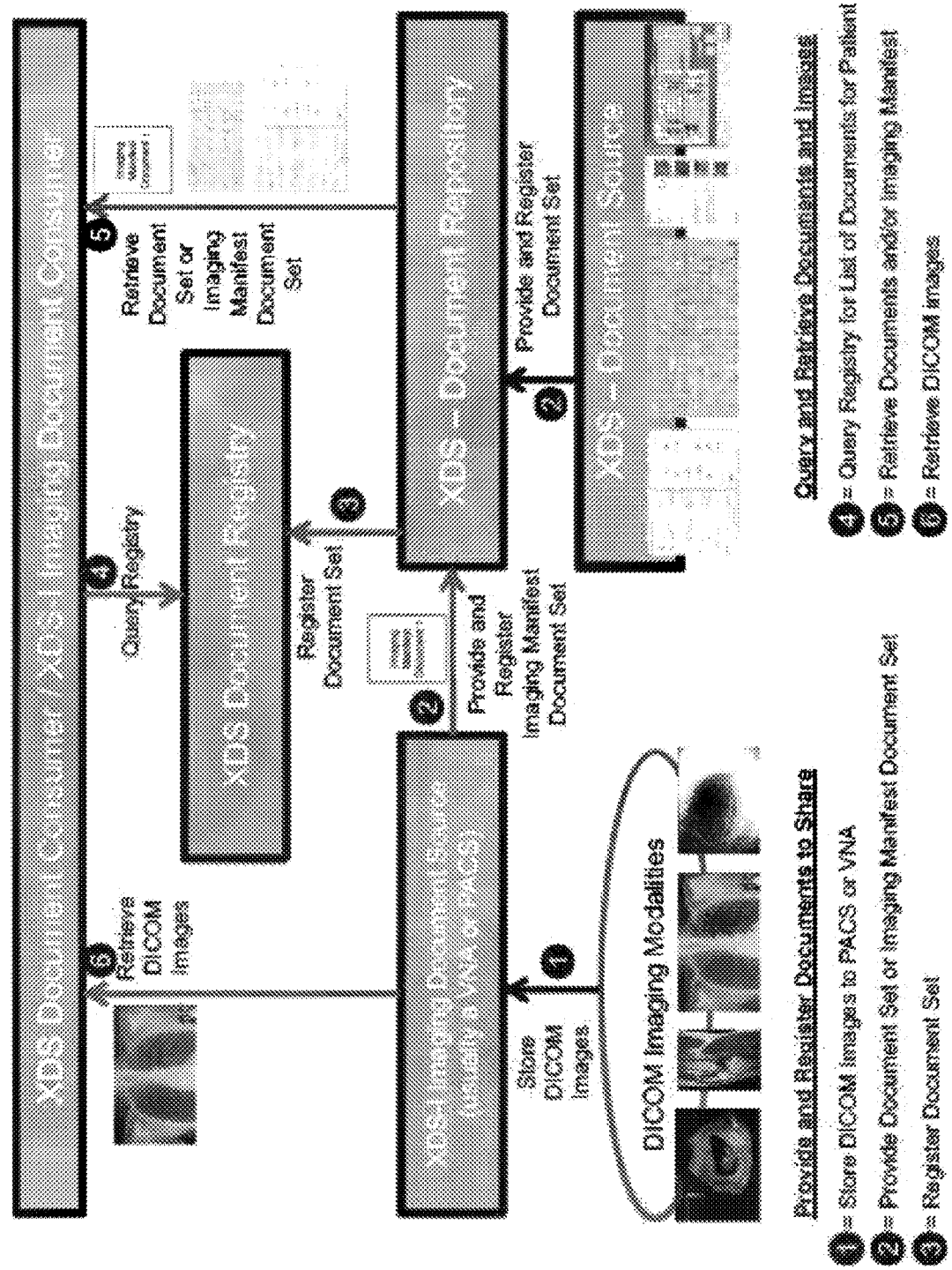
FIG. 38, depicts Imagery Document Exchange with Metadata Registries and an Enterprise Imaging Data Repository.
Figure 39:
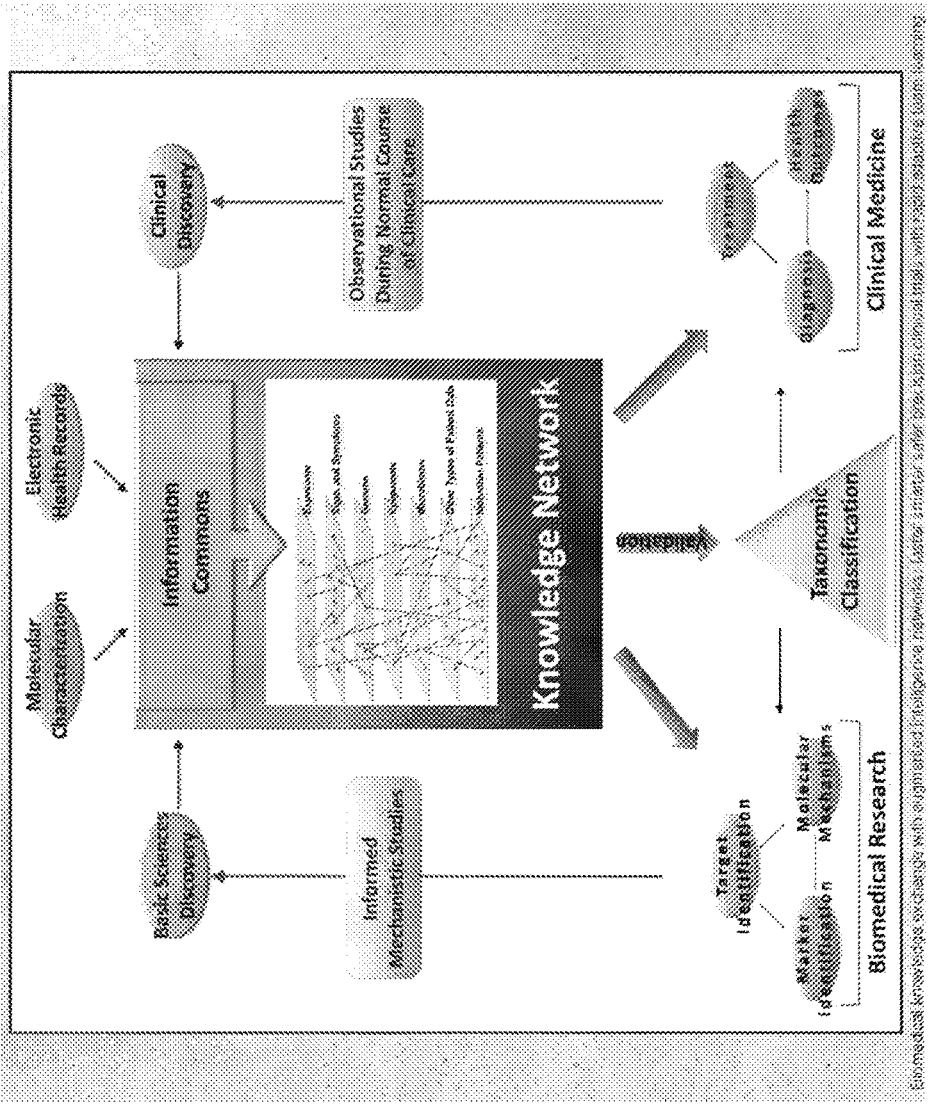
FIG. 39, depicts Biomedical Knowledge Exchange with Augmented Intelligence Networks.
Figure 40:
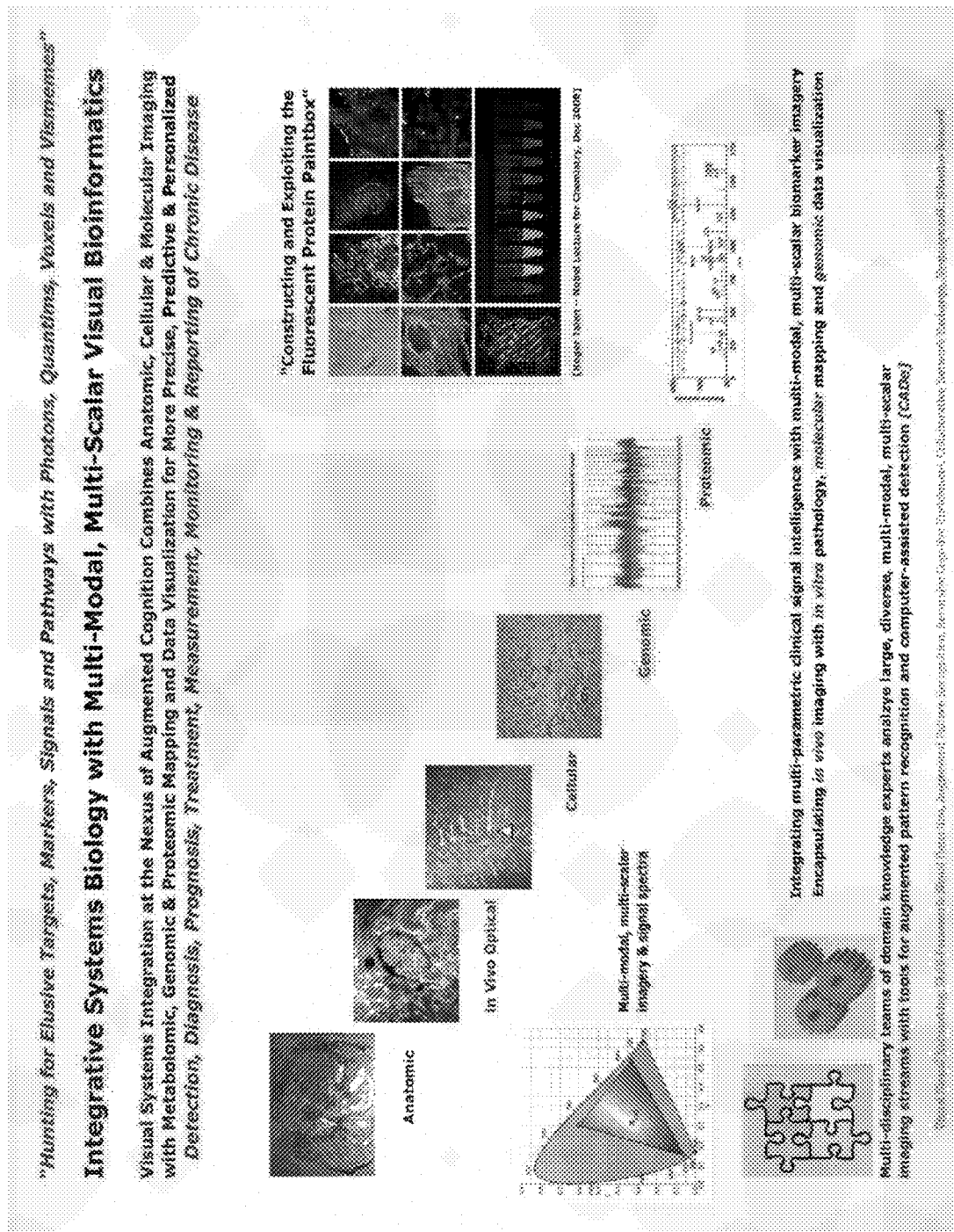
FIG. 40, depicts Integrative Systems Biology with Multimodal, Multi-Scalar Visual Bioinformatics.
Figure 41:
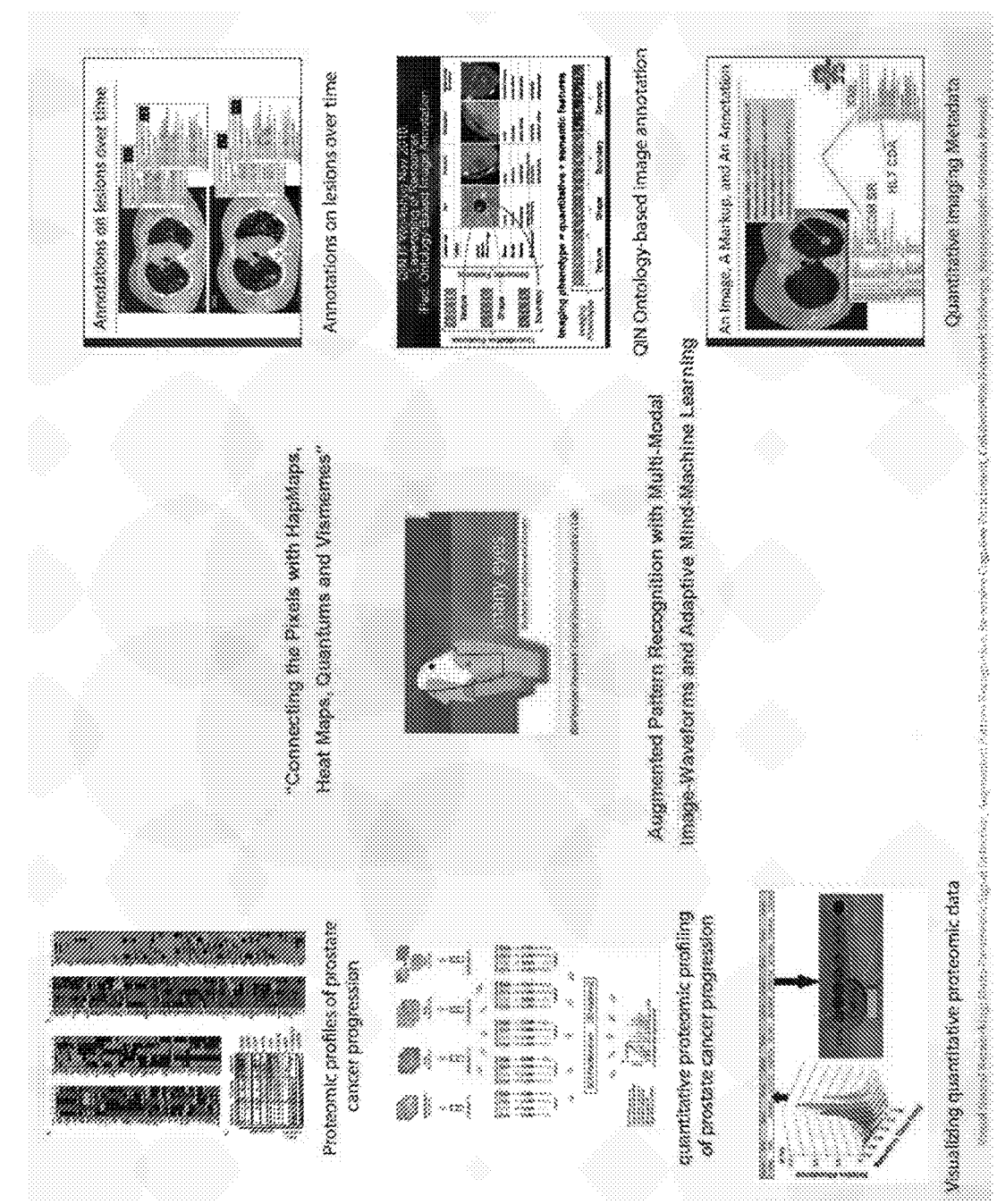
FIG. 41, depicts Augmented Pattern Recognition with Multimodal Radiogenomic Imagery and Adaptive Mind-Machine Learning.
Figure 43:
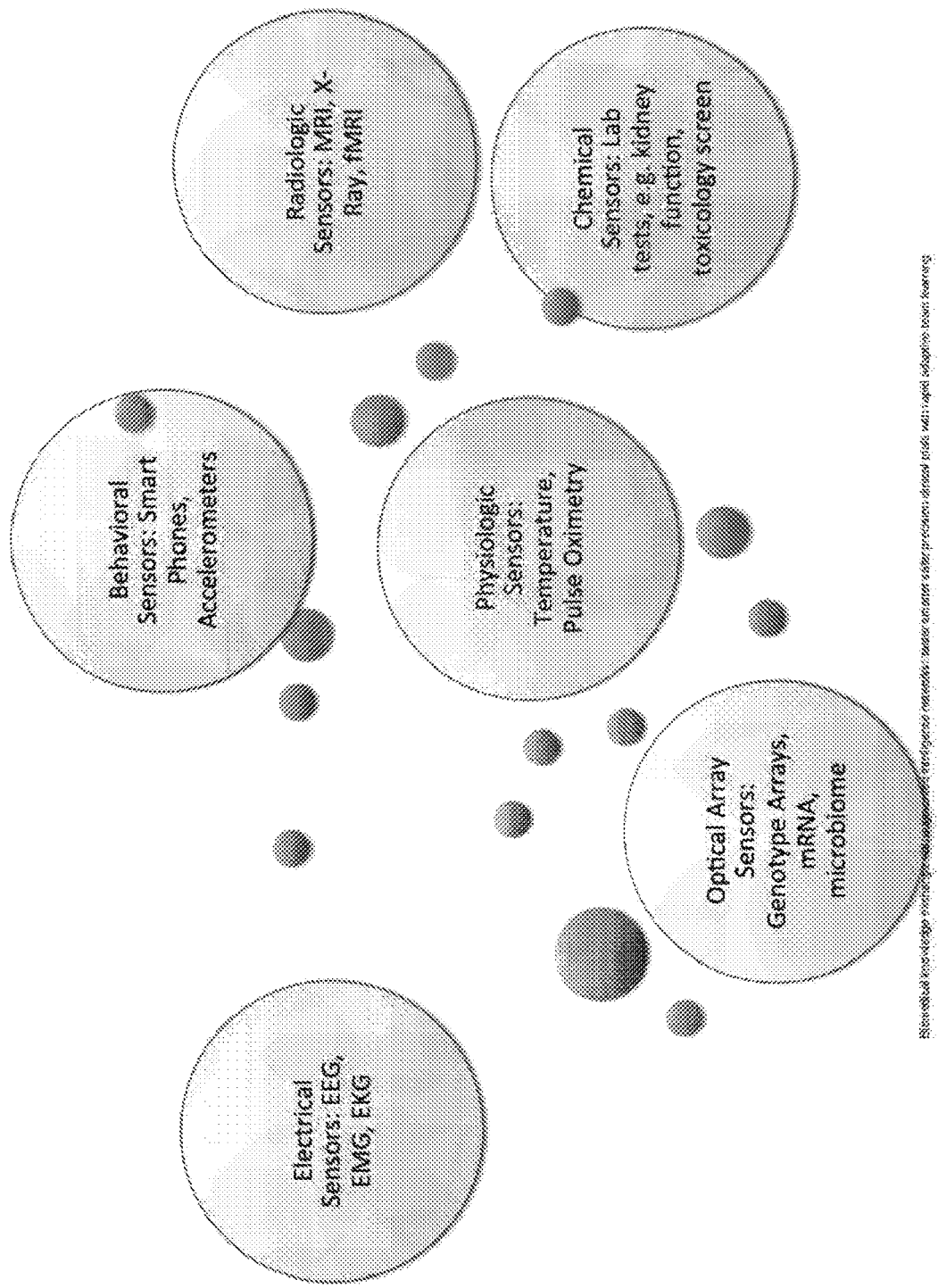
FIG. 43, depicts Early Disease Detection with Multimodal, Multi-Scalar Biomedical Sensors.
Figure 44:
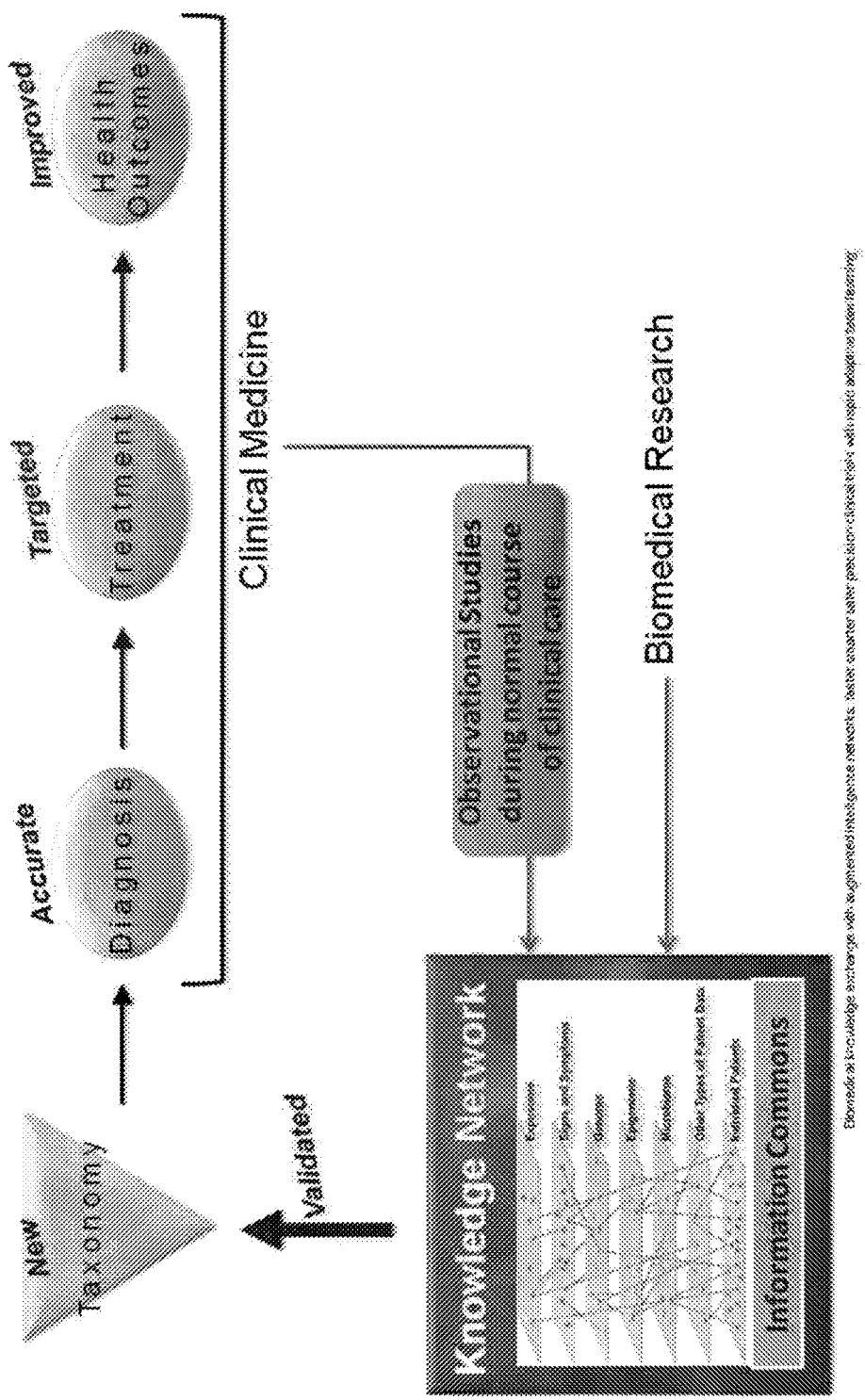
FIG. 44, depicts Clinical Knowledge Networks Integrating Biomedical Research with Clinical Medicine, "from Bench to Bedside".
Figure 45:
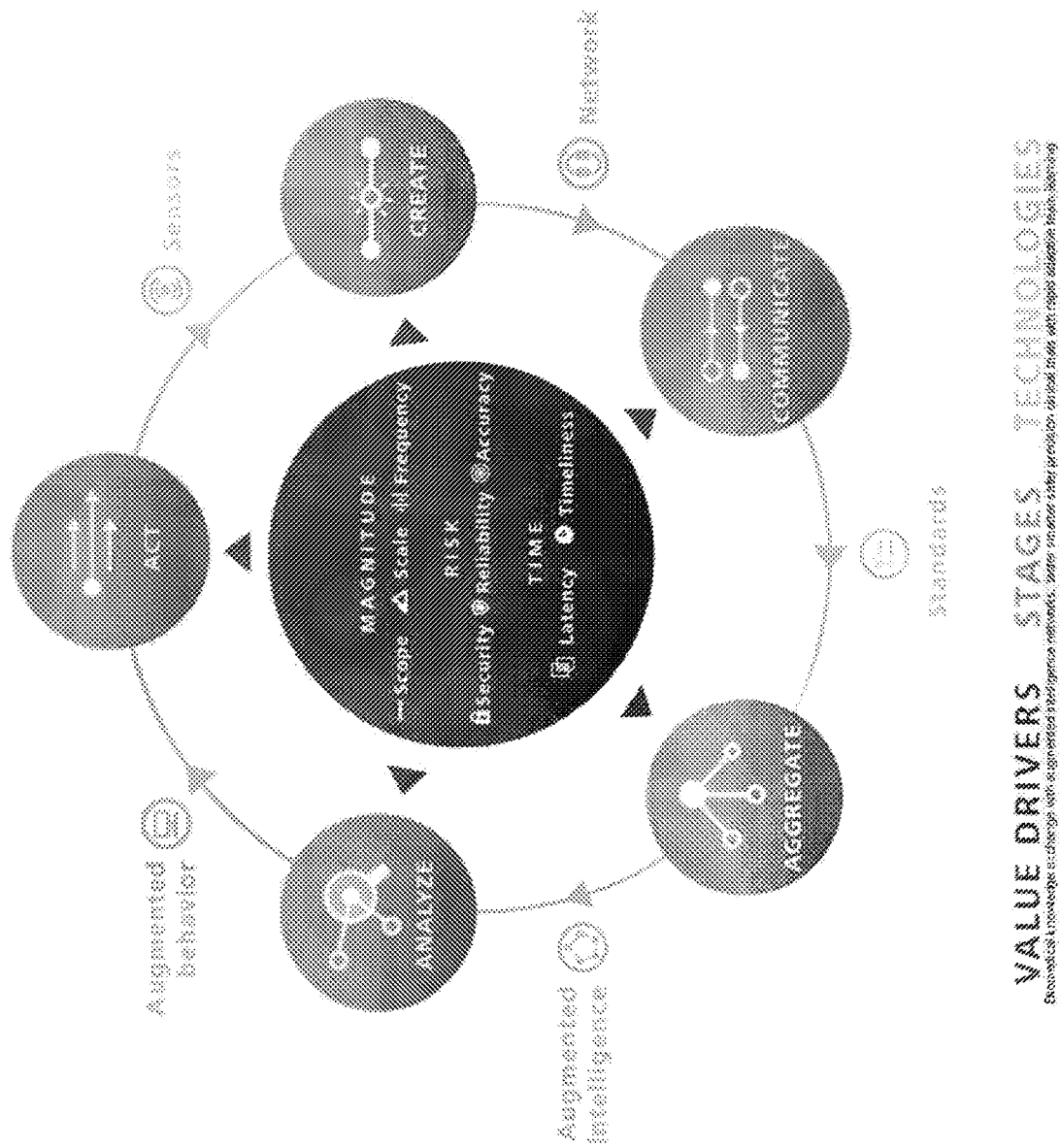
FIG. 45, depicts Value Drivers for Biomedical Knowledge Exchange with Augmented Intelligence Networks.
Figure 46:
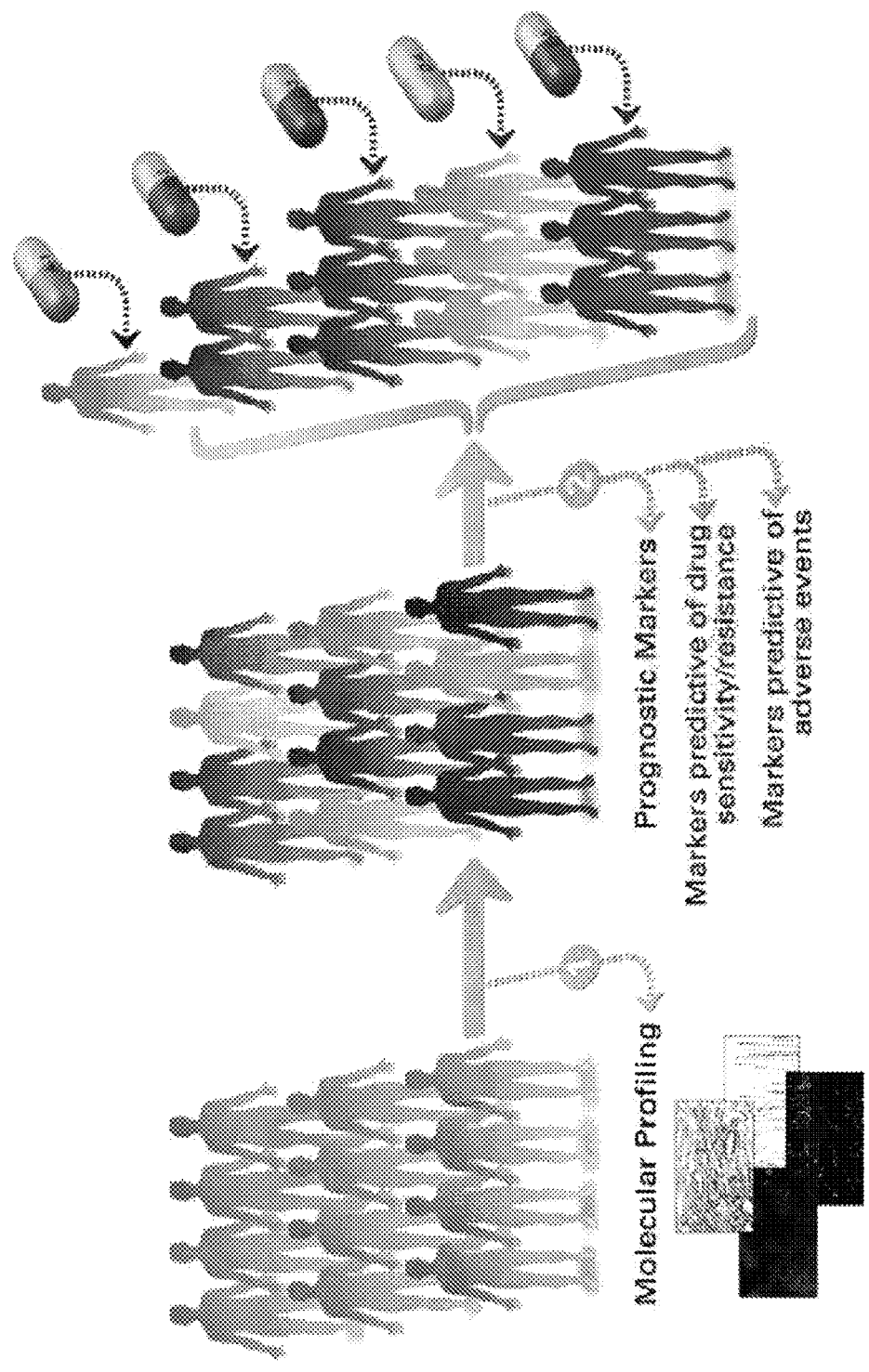
FIG. 46, depicts Molecular Profiling with Predictive Prognostic Markers for Precision Cancer Medicine.
Figure 47:
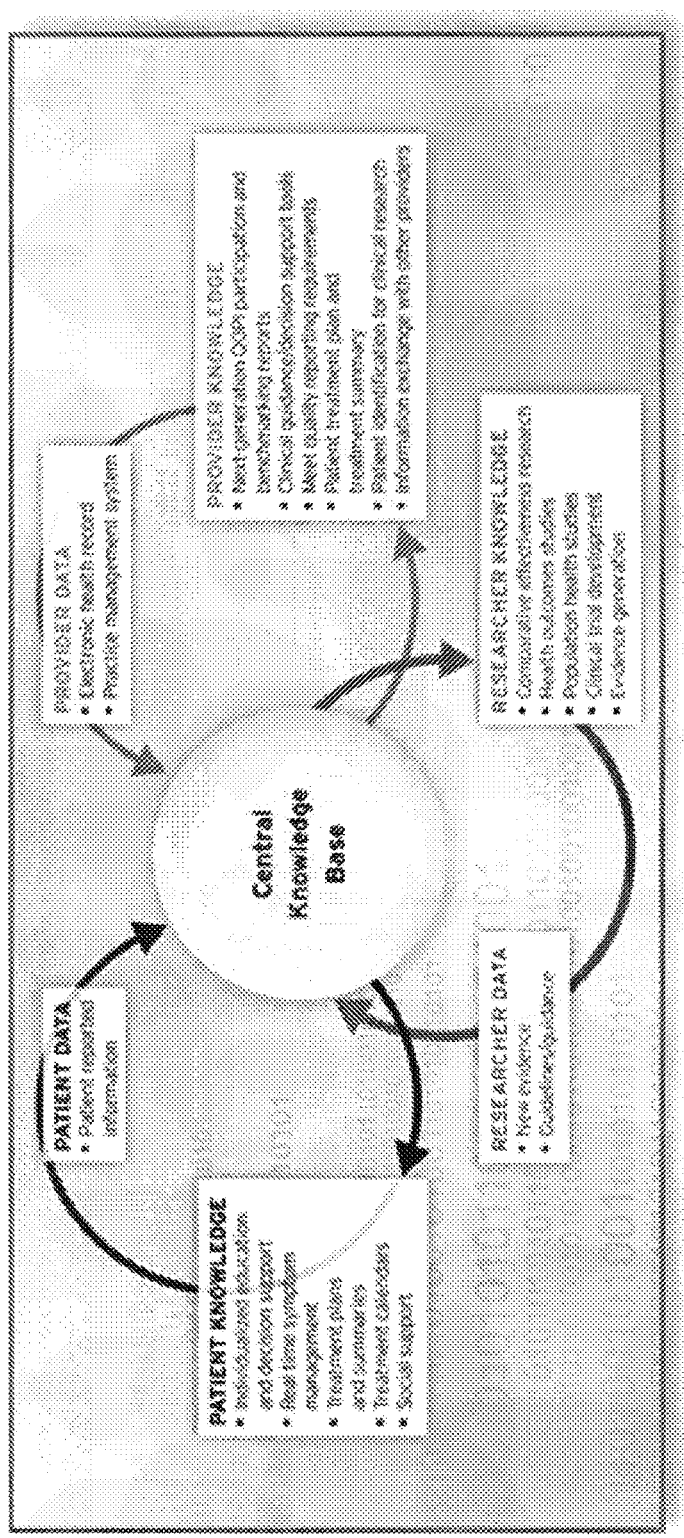
FIG. 47, depicts Cancer LINQ—A Learning Intelligence Network Connecting Patients, Providers and Researchers with Biomedical Data and Knowledge.
Figure 48:
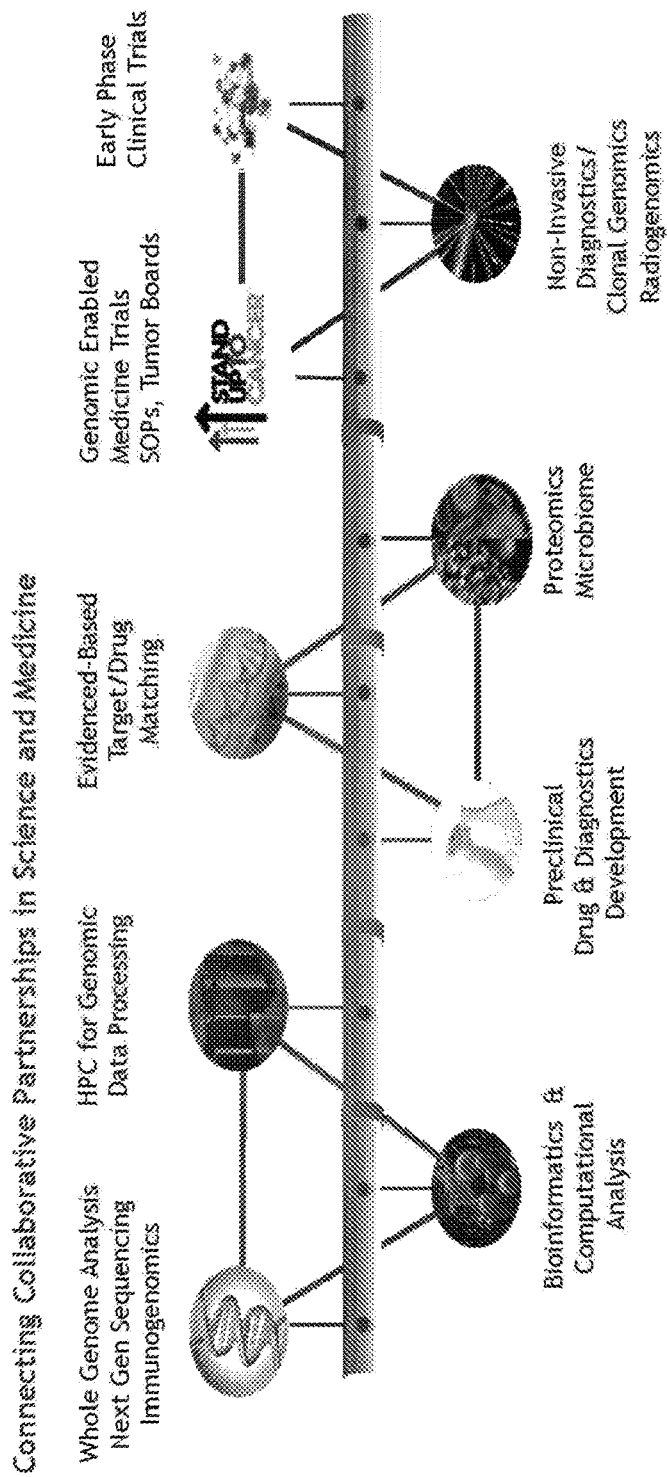
FIG. 48, depicts Connecting Collaborative Partnerships for Multiomic Data Analysis and Personalized Precision Medicine.
Figure 49:
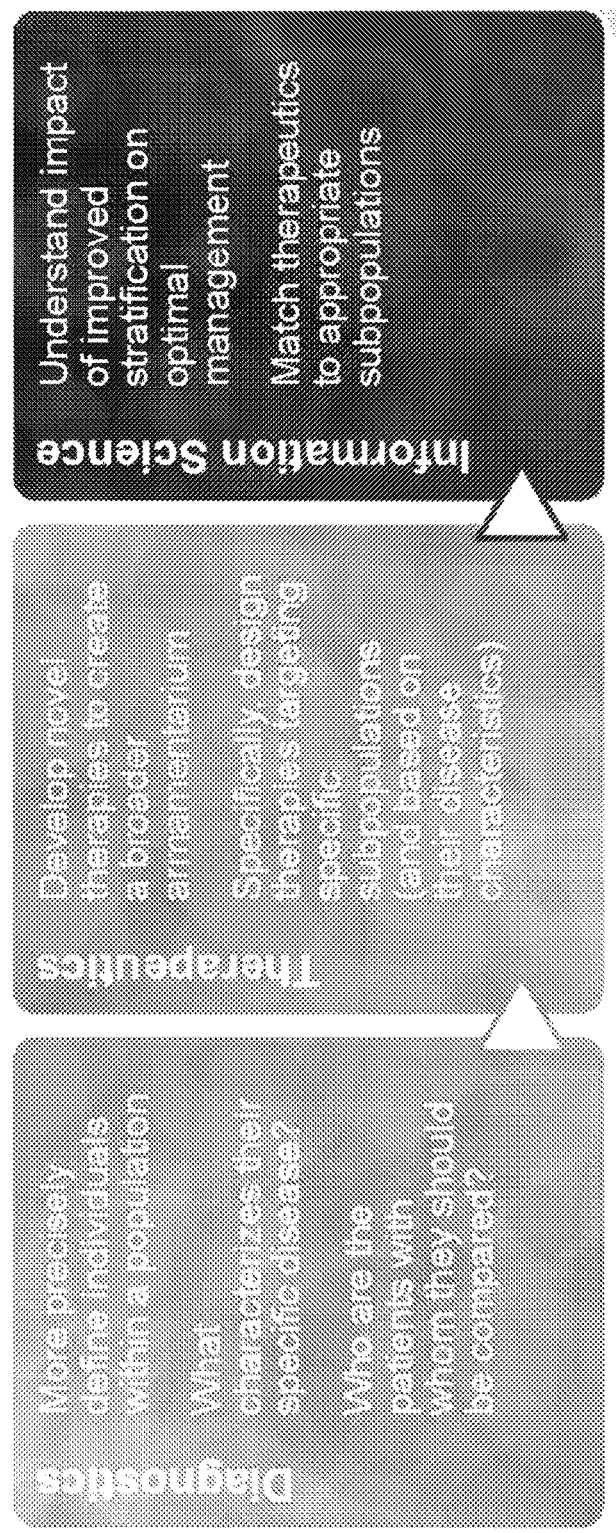
FIG. 49, depicts Precision Diagnostics and Precision Targeted Therapeutics Information Sciences for Personalized Precision Medicine.
Figure 50:
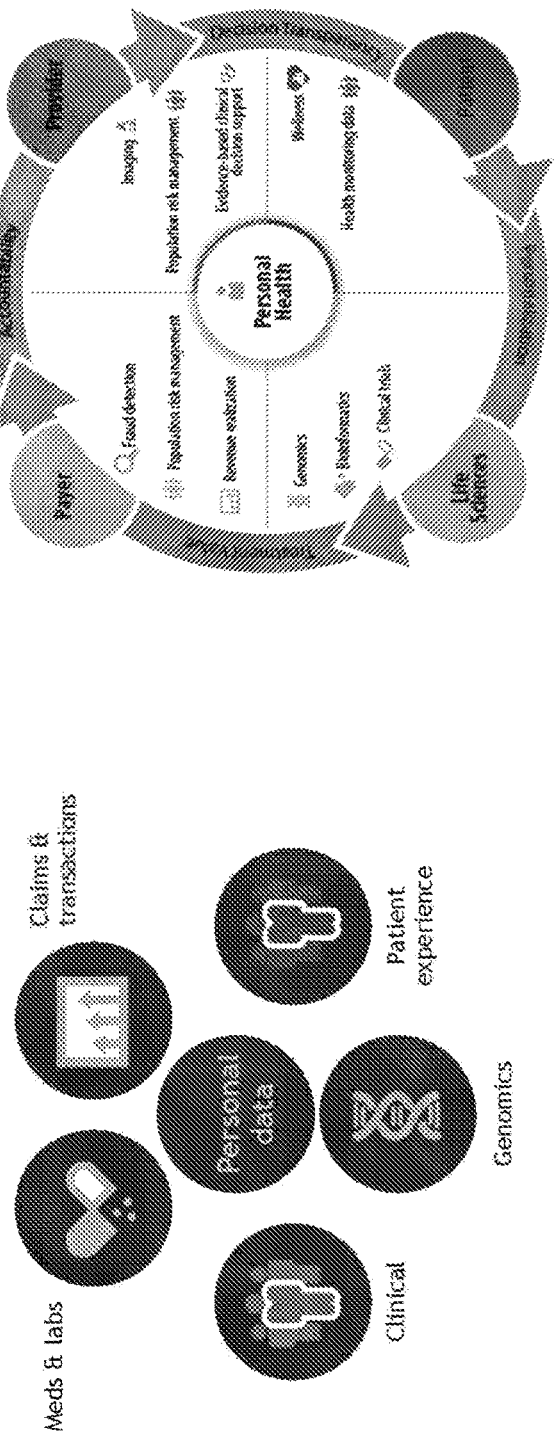
FIG. 50, depicts Clinically Actionable Information from Big Data as the foundation for Personalized Precision Medicine.
Figure 51:
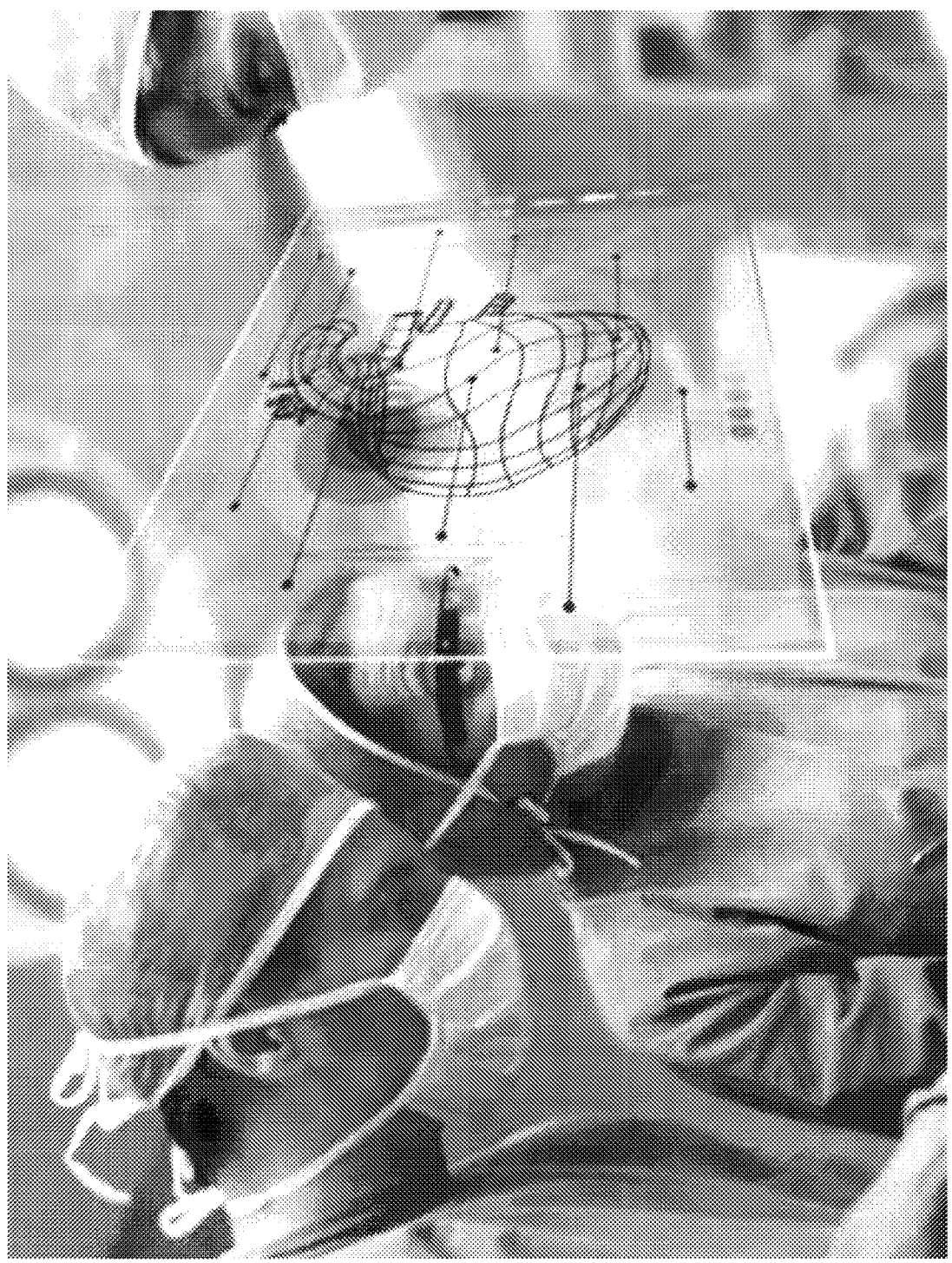
FIG. 51, depicts "See One. Do One. Teach One." Surgical Telementoring, Teamwork and Training.
Figure 52:
FIG. 52, depicts Imagery Guided Computer Assisted Surgery.
Figure 53:
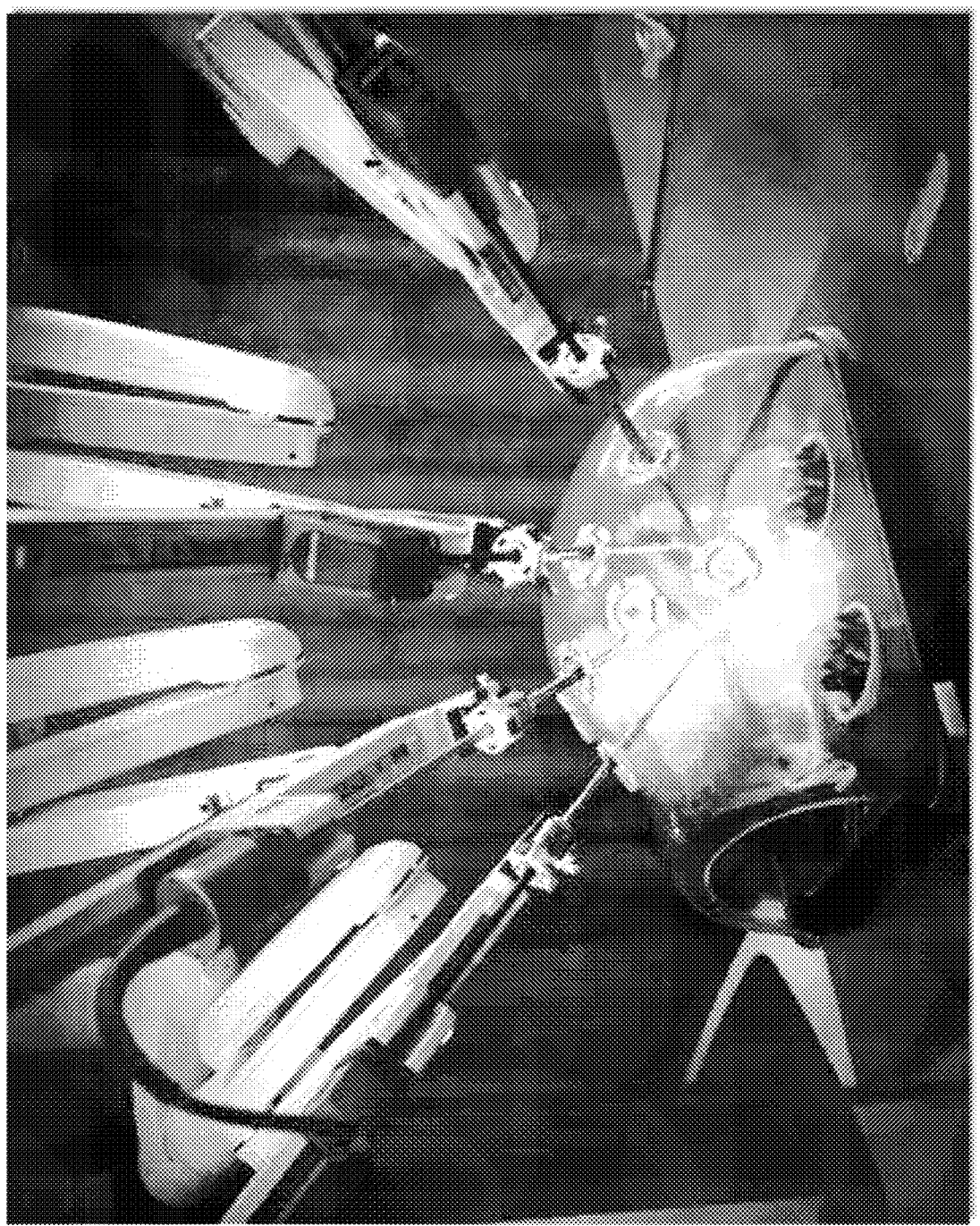
FIG. 53, depicts Informatics-Enriched Robotic Assisted Surgery.
Figure 54:
FIG. 54, depicts Streaming Augmented Reality Surgical Instruction.
Figure 55:
FIG. 55, depicts Surgical Navigation and Guidance with 3D Data Visualization and Streaming Augmented Reality.
Figure 56:
FIG. 56, depicts Visualizing the Surgical Site for Robotic Assisted Intervention.
Figure 57:
FIG. 57, depicts an Imagery Guided Minimally Invasive Surgical Robotic System.
Figure 59:
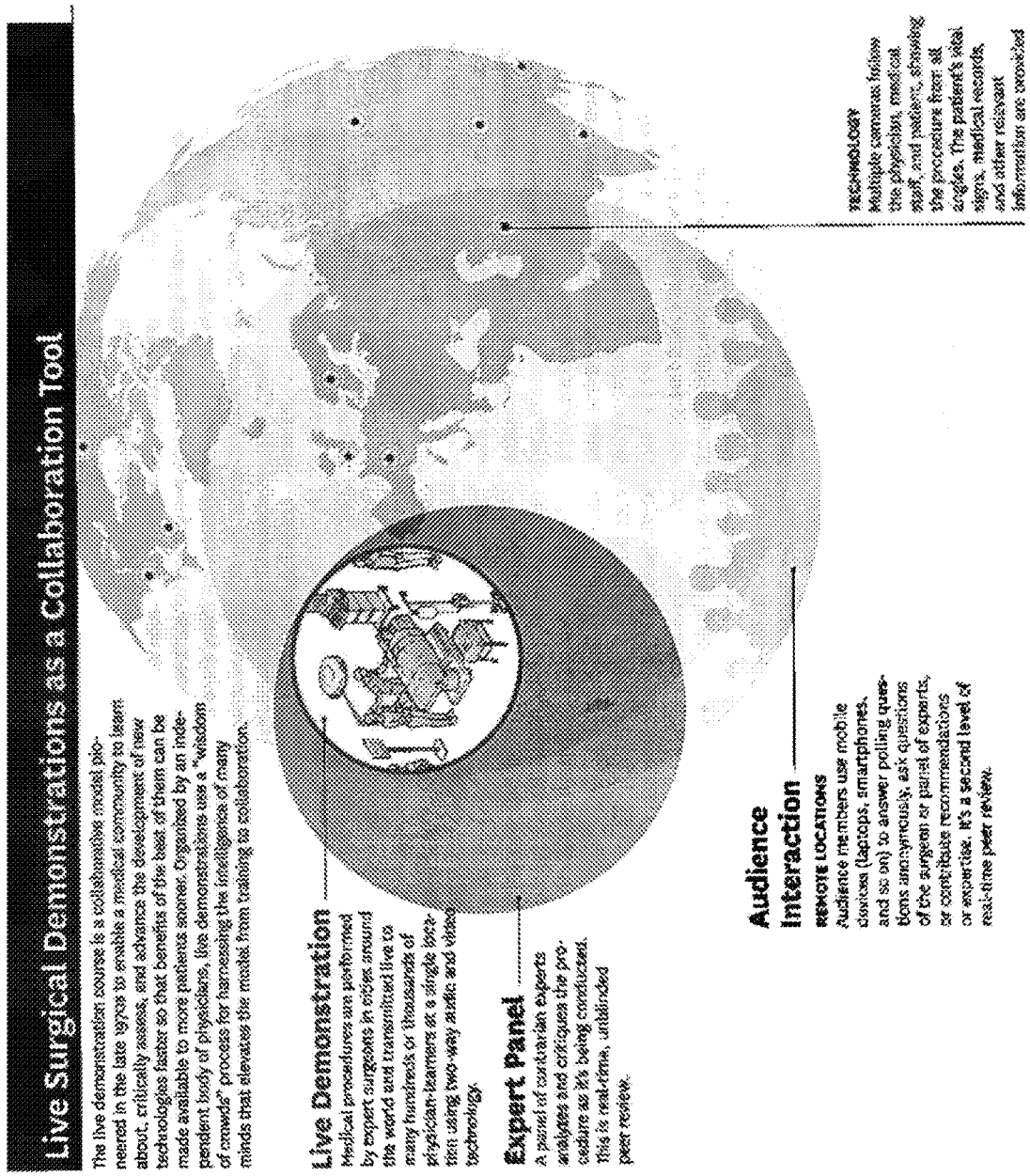
FIG. 59, depicts Live Surgical Demonstration with Expert Panels as Collaborative Teaching Tools.
Figure 60:
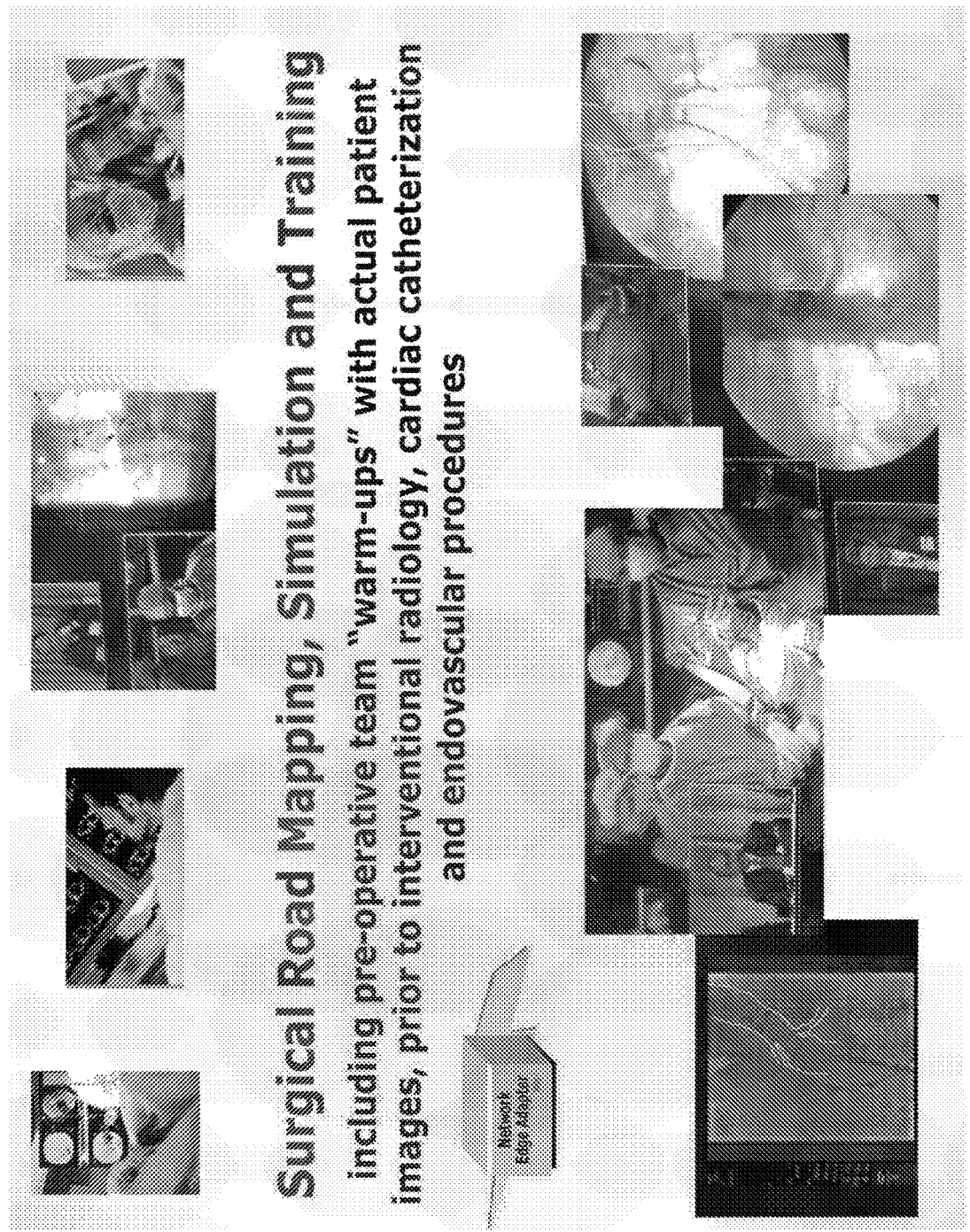
FIG. 60, depicts Live Remote Intraoperative Telesurgical Consultation during Aneurysm Repair.
Figure 61:
FIG. 61, depicts Live Remote Surgical Telementoring, Teamwork & Training with Interactive Streaming Video and Multisensory Augmented Reality.
Figure 62:
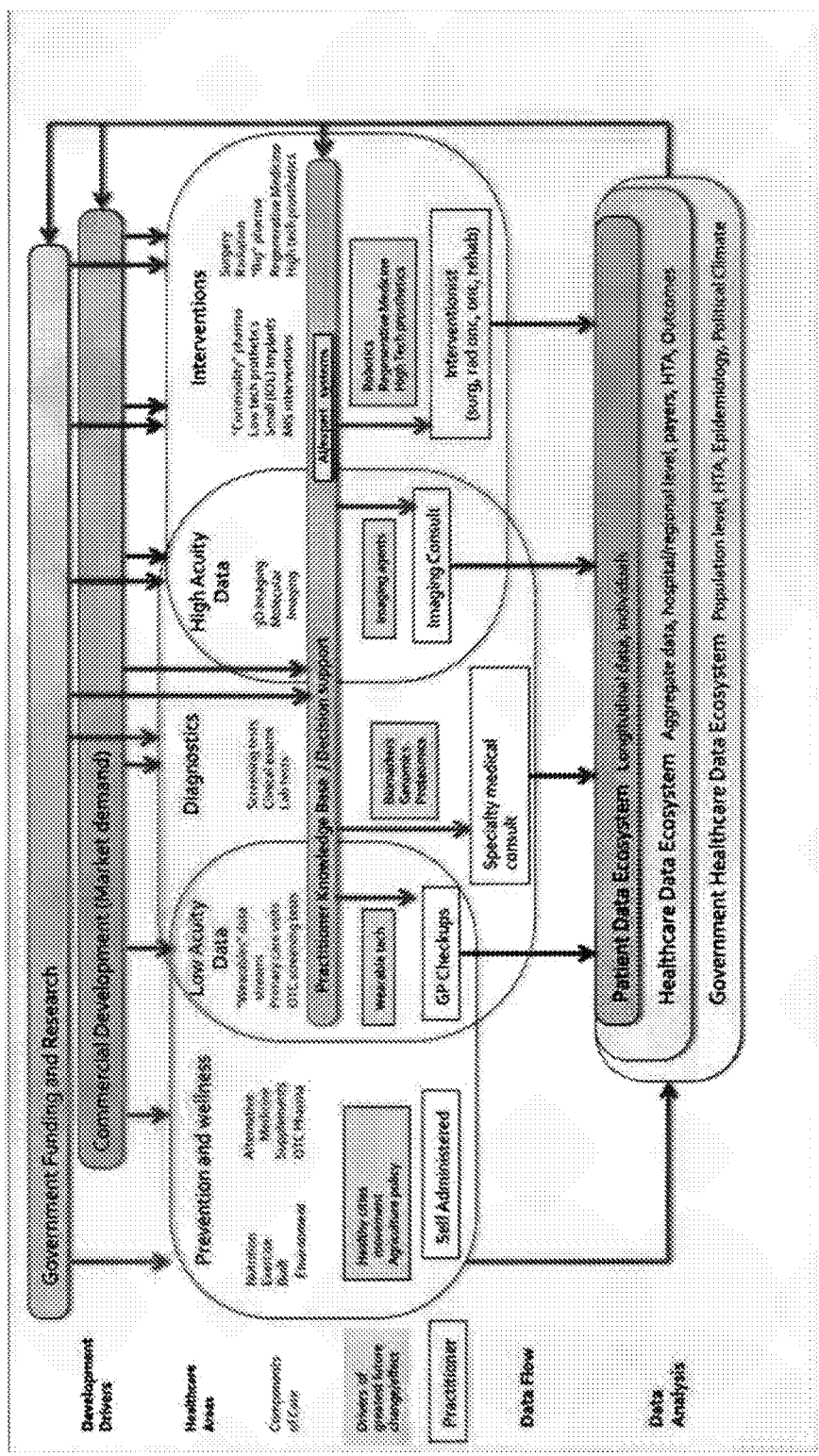
FIG. 62, depicts interconnected Ecosystems of the Future for Informatics-Enriched Imagery Guided Interventions.

In another embodiment, a participant cognitive collaborant 10, known as Hospitalist, remotely monitors live streaming imagery data 13 from a surgical procedure in an operating room on channel one, and archived streaming imagery data 13 of a patient recovering in Intensive Care Unit, on channel two. While monitoring streaming imagery data 13 on channels one and two, as depicted in FIG. 3 and FIG. 7, Hospitalist accepts an invitation to join a collaboration session on channel three to monitor and consult live on a diagnostic procedure in the emergency room, as shown in FIG. 6. The live consultation involves review of patient images from an analog ultrasound machine and a digital CT scanner in the emergency room. During the collaboration session in the emergency room on channel three, Hospitalist utilizes the multi-channel viewing capability of Applicant's network system 1 to continue live monitoring of streaming imagery data 13 on channel one and channel two, and to retrieve and view additional archived imagery data 13 of patient recovery in Intensive Care Unit.

In another embodiment, a patient is recalled to undergo a second PET/MRI scan. The previous test yielded inconclusive, due to patient motion during image capture, thus requiring a costly retest. During the second test, Radiologist was able to review the MRI images captured 13 during the first portion of the test, while the patient was still being imaged in PET unit and confirm that the second MM scan was useable. Radiologist was able to advise Attending Molecular Pathologist during PET scan 13 of additional regions of interest with input illustrations 18 for further investigation.

In another embodiment, Oncologist wishes to convene a virtual tumor board for the following day involving multi-specialist collaboration with a patient's Radiologist, Pathologist, Oncology Surgeon and himself. Oncologist sends invitations to colleagues along with several collaborated imagery files he wishes to review during the collaboration session. Radiologist and Pathologist confirm availability, but Oncology Surgeon is unable to attend. However, Oncology Surgeon is able to annotate 23 with telestrations 21 and drawings 22 on several key images 13 included in the collaborated imagery study sent with the session invitation. Oncology Surgeon also includes his clinical notes and an audio file along with his report, together all encapsulated as a CIF and returned to the session host.

During the collaboration session the following day, the host Oncologist retrieves patient images from PACS 4 and from his local media library 25 containing the CIF 13, 18 sent to him from Oncology Surgeon, viewing both images concurrently when colleagues from radiology and pathology join the collaboration session. During the collaboration session, Pathologist is monitoring on the third channel of the multi-channel streamer 7, 8, 9, 25, a tumor removal of another patient in the operating room, advising that Oncology Surgeon intra-operatively regarding sufficiency of margins of tumor removal from that patient. Oncology Surgeon is able to share live imagery 13 of the tumor removal with the radiology and oncology colleagues who have joined the virtual tumor board collaboration session.

At the conclusion of the collaboration session, host Oncologist encapsulates and saves input illustrations 18 from participant cognitive collaborants 10, including encapsulated audio clinical notes and biopsy reports as clinical documents, saving them as collaborated imagery files and sending them to all participant cognitive collaborants 10 as well as invitees unable to attend. Additionally, the CIFs 13, 18 are sent to PACS 4 for inclusion in the patient's electronic medical records as well to patient's referring clinician.

Other embodiments of the invention include applications for cognitive value creation with knowledge mapping, advanced and augmented data analytics, as depicted in FIGS. 19 through 24; for augmenting clinical intelligence with semantic metadata and imagery annotation, as depicted in Figures through 31; for cognitively-enriched enterprise imaging with streaming imagery informatics, as depicted in FIGS. 33 through 38; for collaborative precision medicine with multiomic data analytics, as depicted in FIGS. 39 through 50; for informatics-enriched imagery guided intervention, including robotic-assisted surgery, as depicted in FIGS. 51 through 62; for machine learning with medical imaging, including deep learning, transfer learning, reinforcement learning, convolutional neural networks, recurrent neural networks, LSTM and NLP, as depicted in FIGS. 63 through 75; for precision guided biomedical nanorobotics, as depicted in FIGS. 76 through 79; and for personalized precision targeted theranostic nanomedicine, as depicted in FIGS. 80 through 85.

Figure 63:
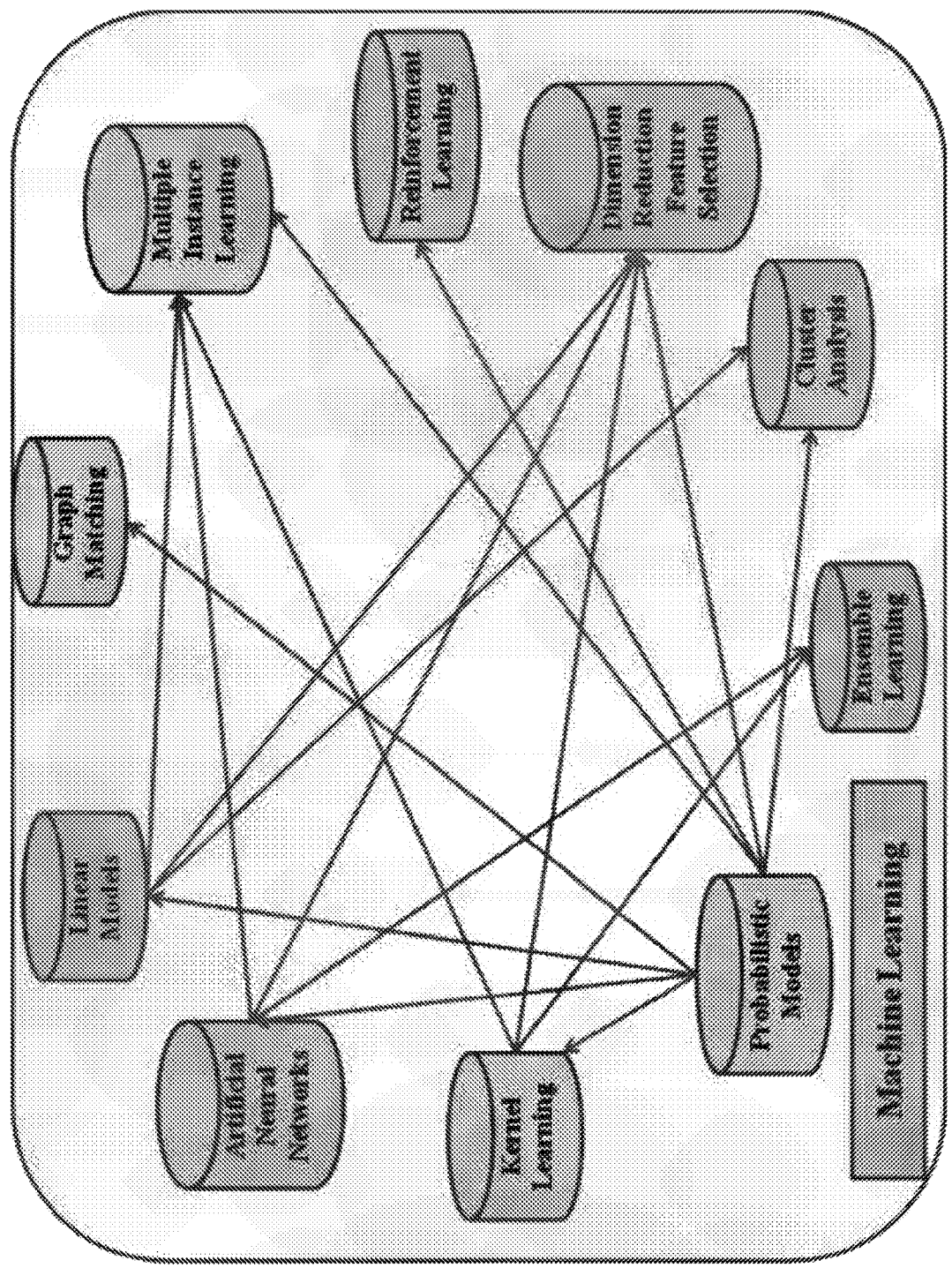
FIG. 63, depicts various techniques for Machine Learning with Medical Imaging.
Figure 64:
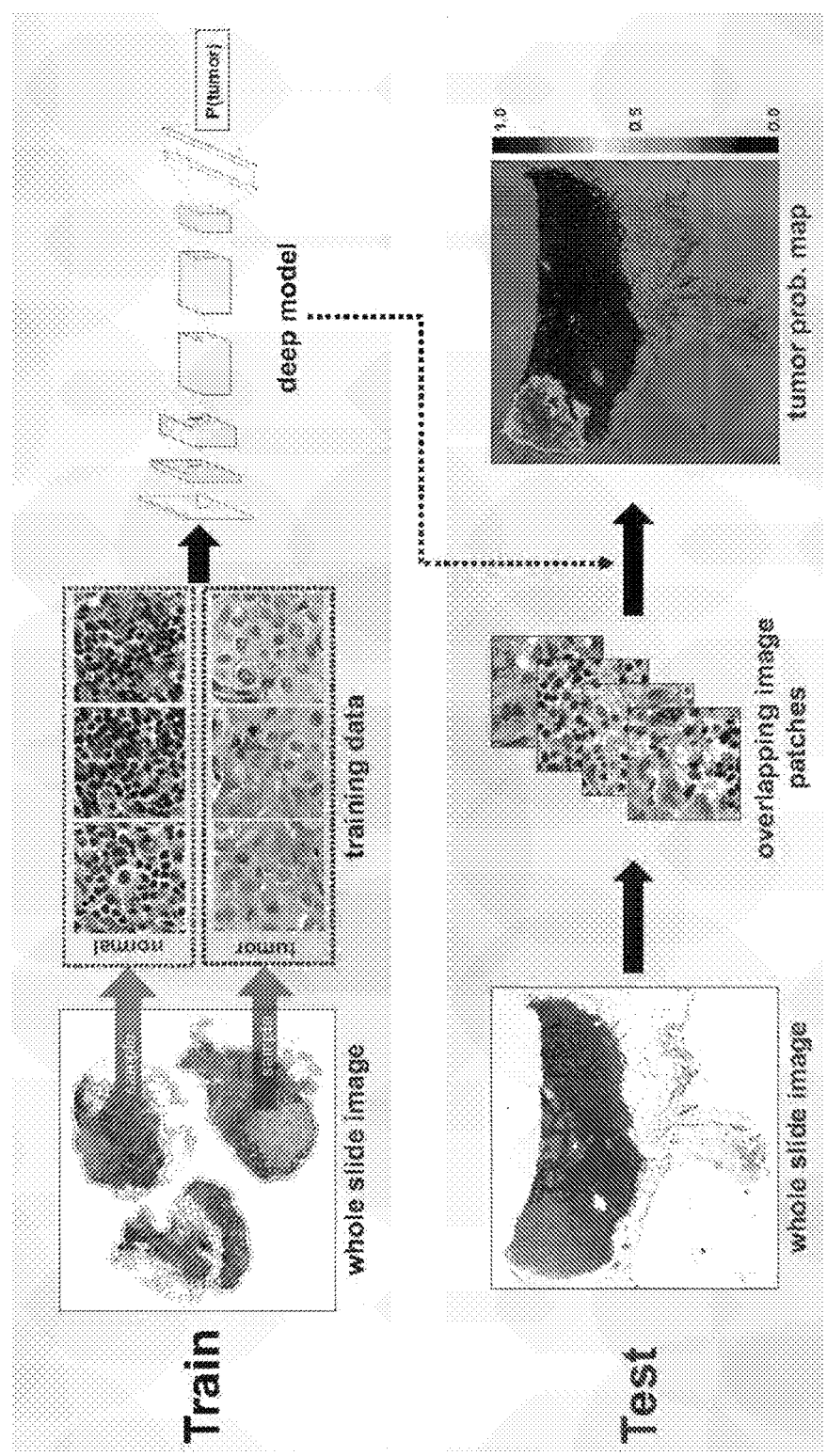
FIG. 64, depicts a Framework for Cancer Metastasis Detection with Deep Learning Models and Whole Slide Imaging.
Figure 65:
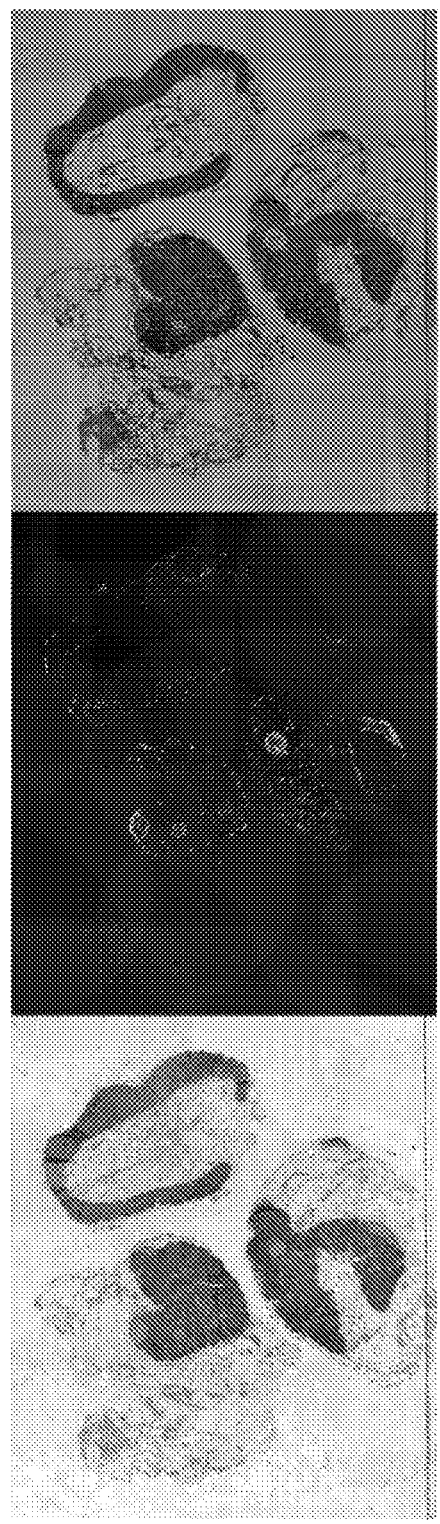
FIG. 65, depicts visualization of Tumor Region Detection with Slide/Heatmap Overlays.
Figure 66:
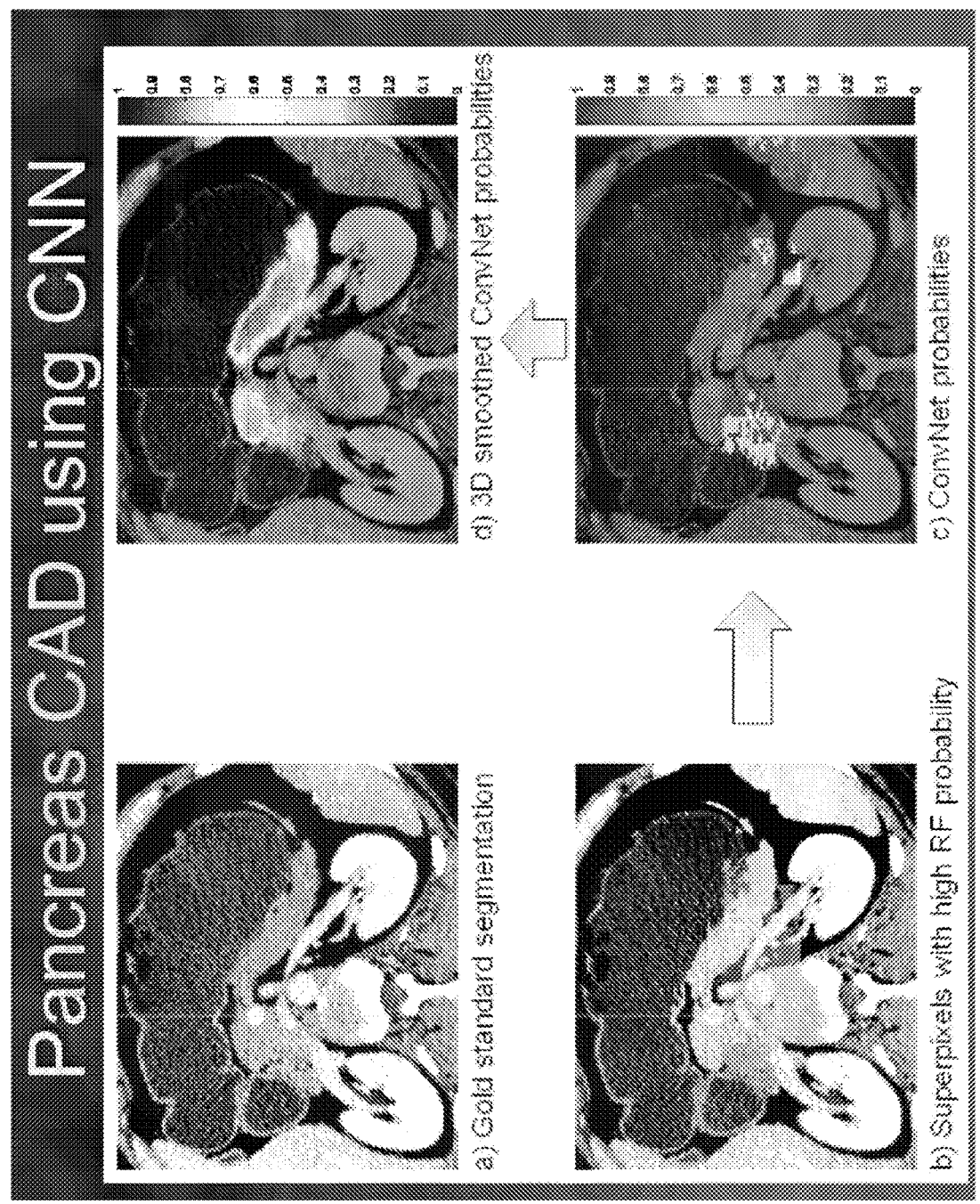
FIG. 66, depicts Pancreatic Cancer Computer Assisted Detection with Convolutional Neural Networks.
Figure 67:
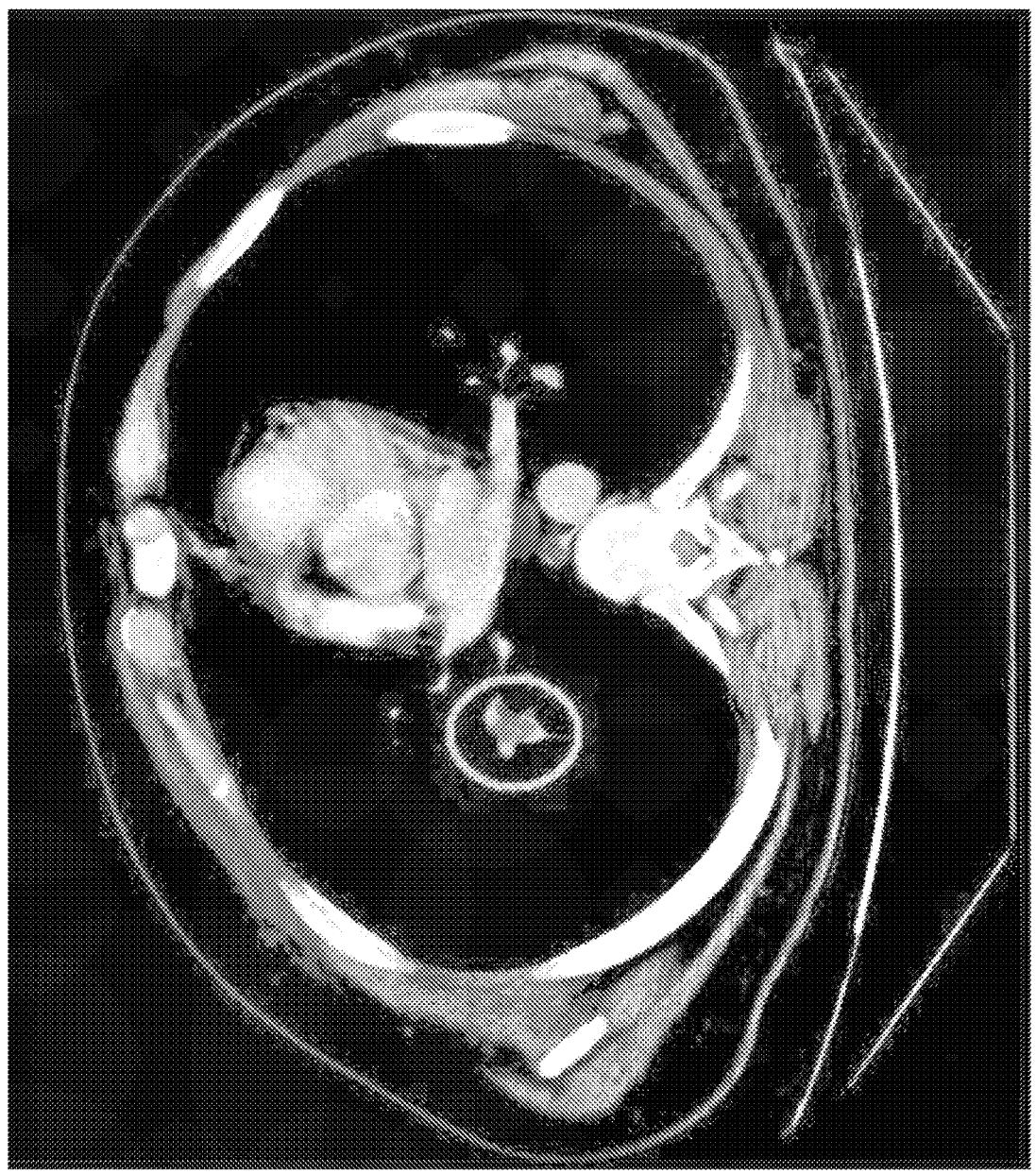
FIG. 67, depicts Pulmonary Embolism Identification with Machine Learning.
Figure 68:
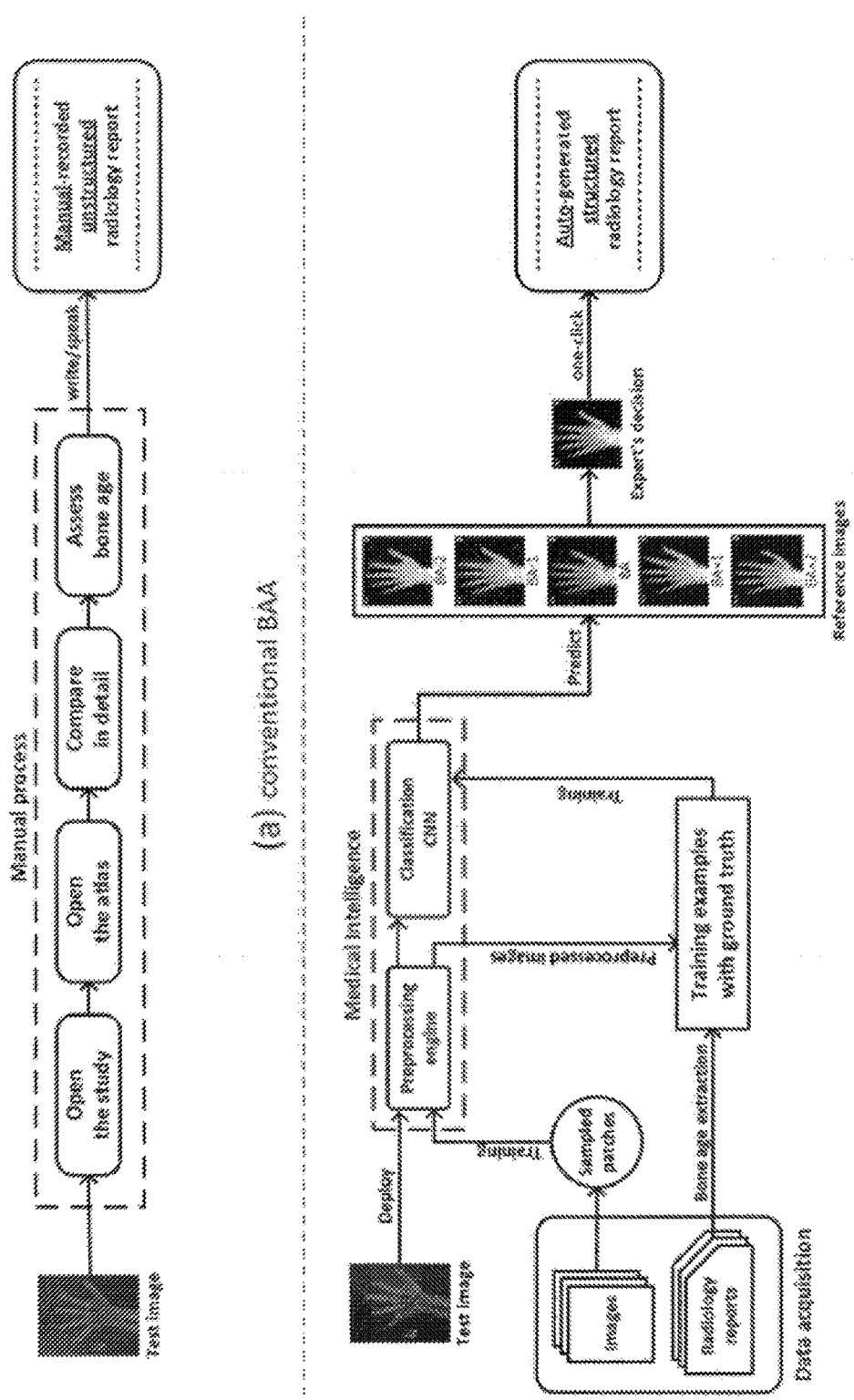
FIG. 68, depicts Bone Age Assessment with Deep Learning Systems.
Figure 69:
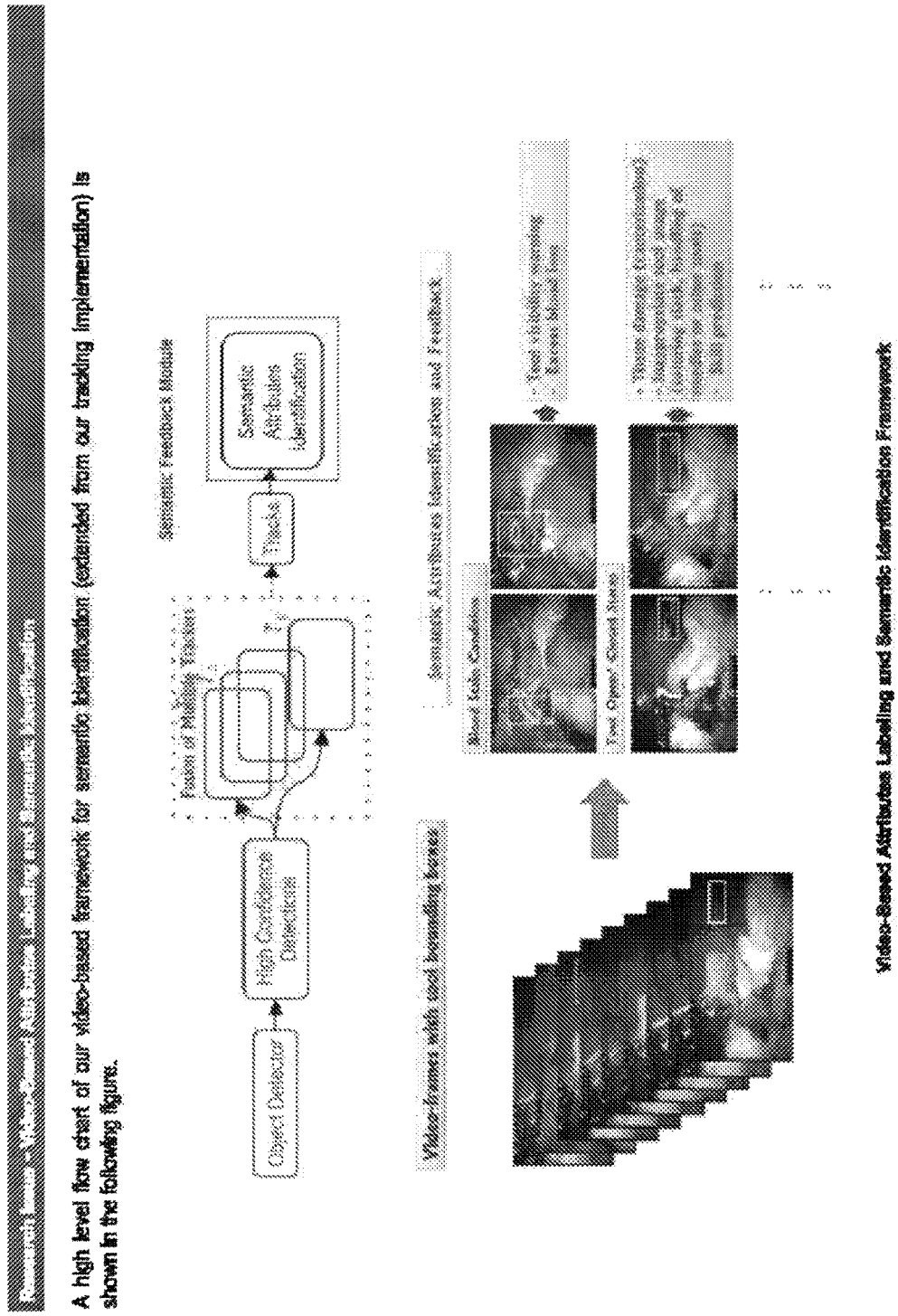
FIG. 69, depicts Video-based Attributes Labeling and Semantic Identification.
Figure 70:
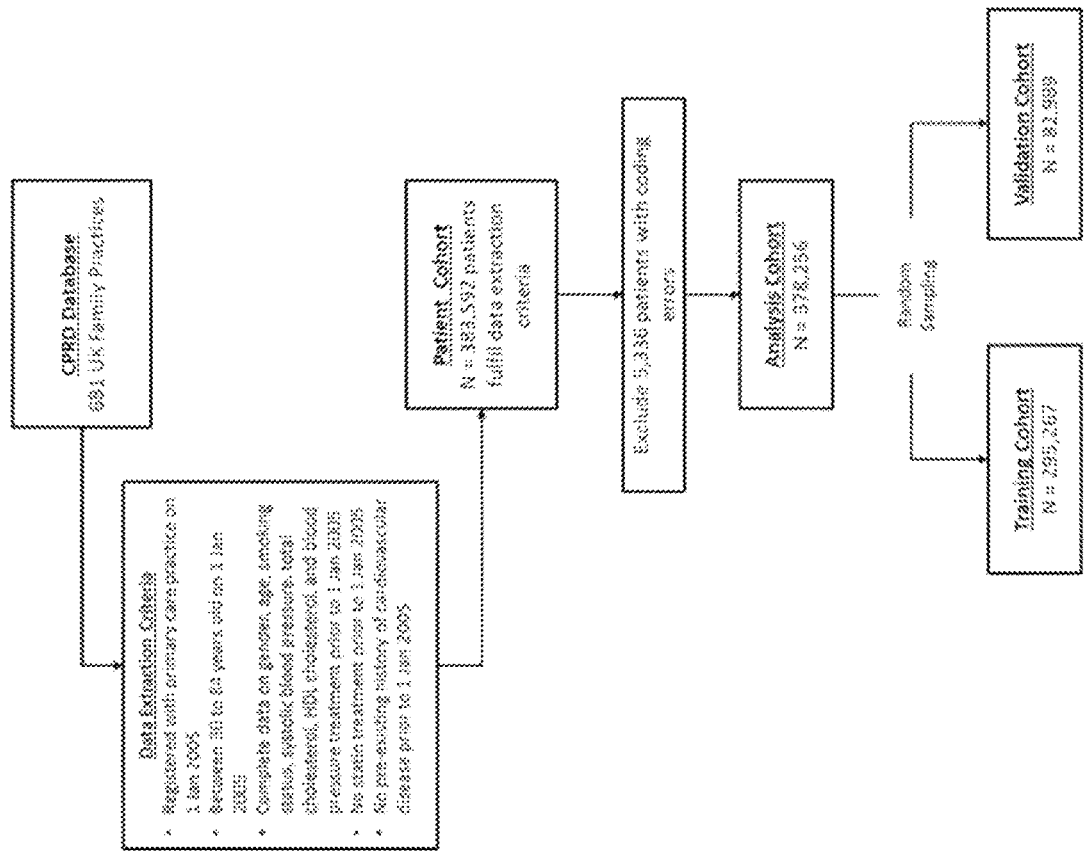
FIG. 70, depicts Data Extraction for Training Machine Learning Systems with Medical Outcomes.
Figure 71:
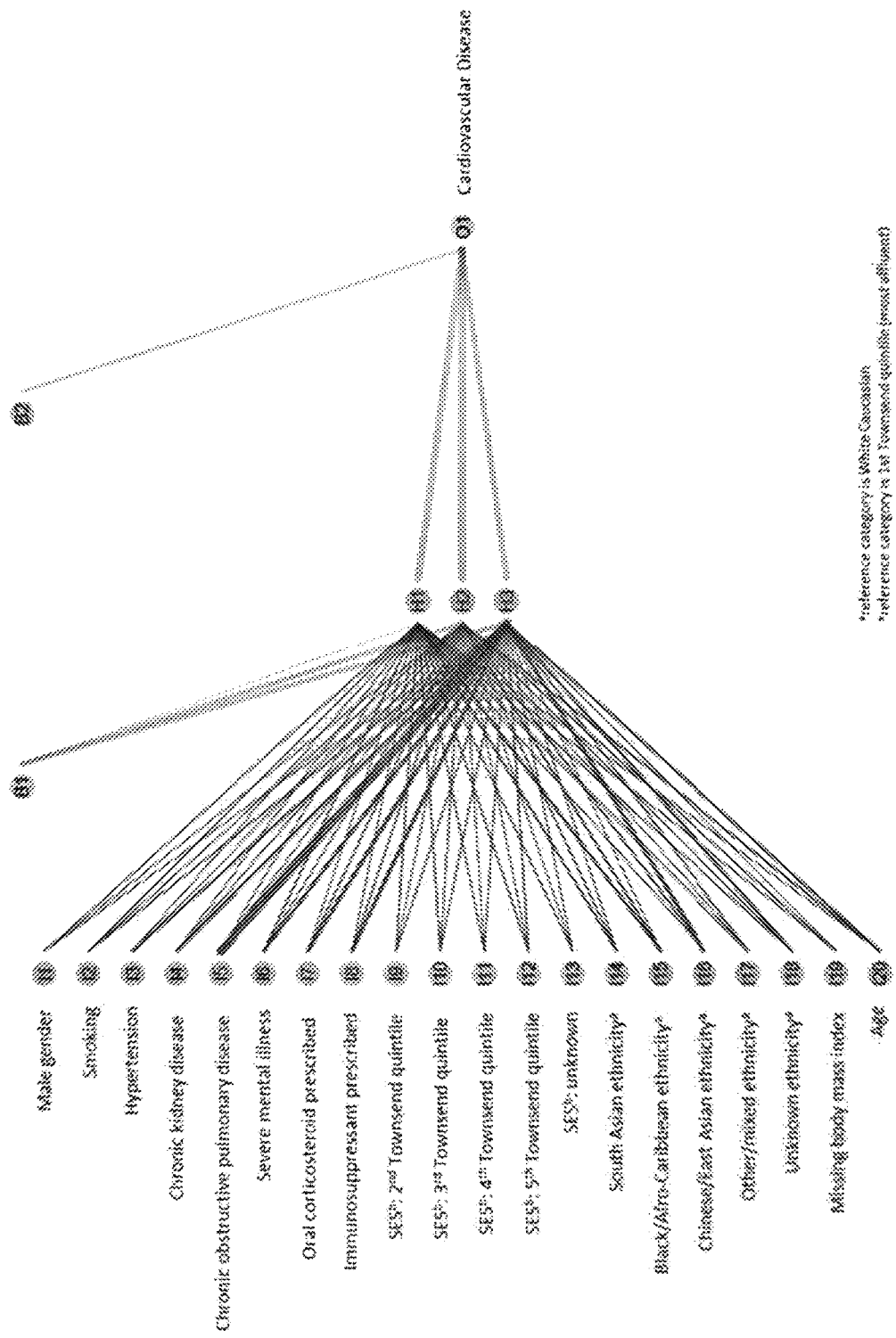
FIG. 71, depicts illuminating "black-box" understanding of Machine Learning results developed from Neural Networks [e.g., XAI—Explainable Artificial Intelligence].
Figure 72:
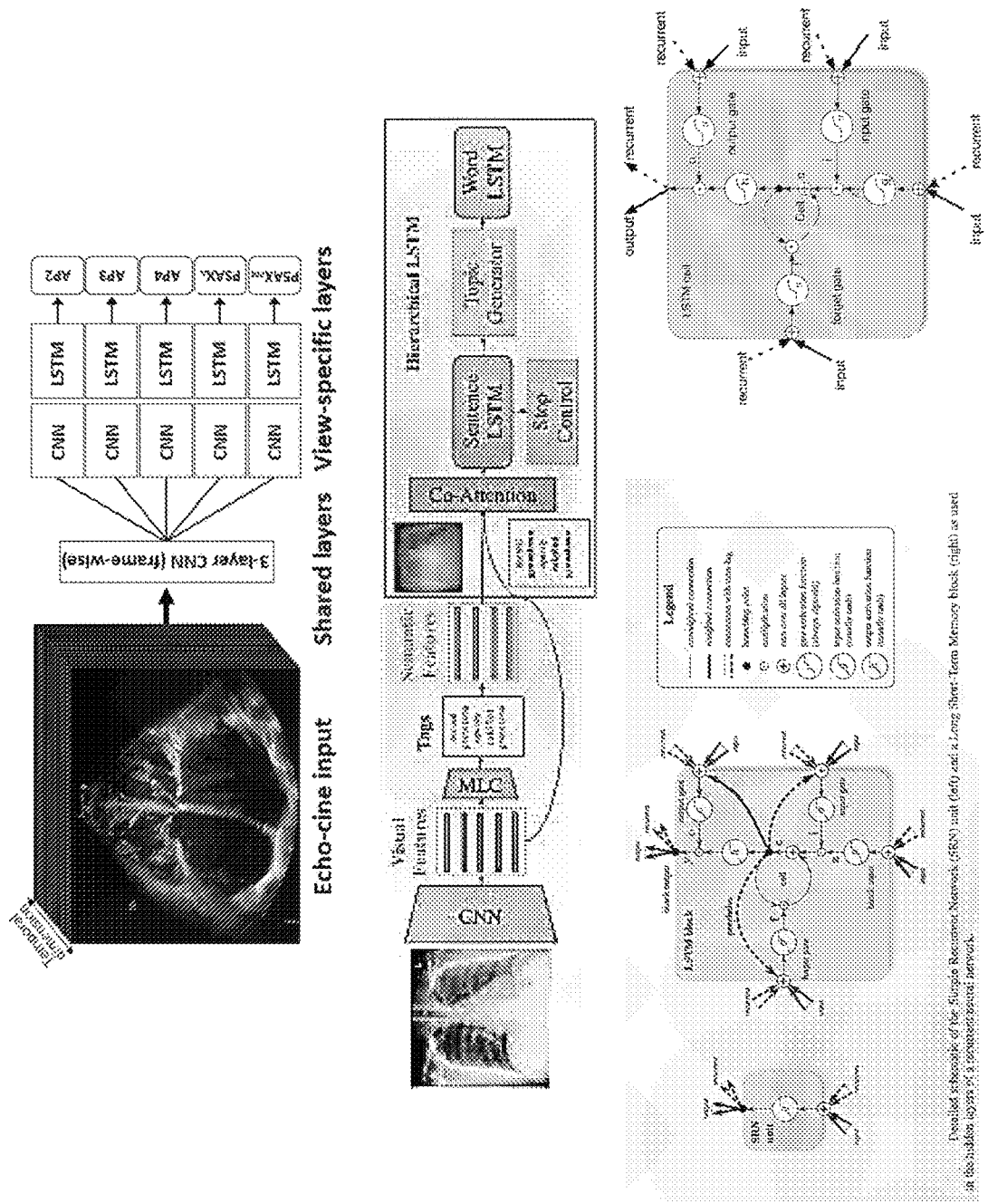
FIG. 72, depicts Convolutional and Recurrent Neural Networks with Long Short Term Memory [LSTM] in Medical Imaging.
Figure 73:
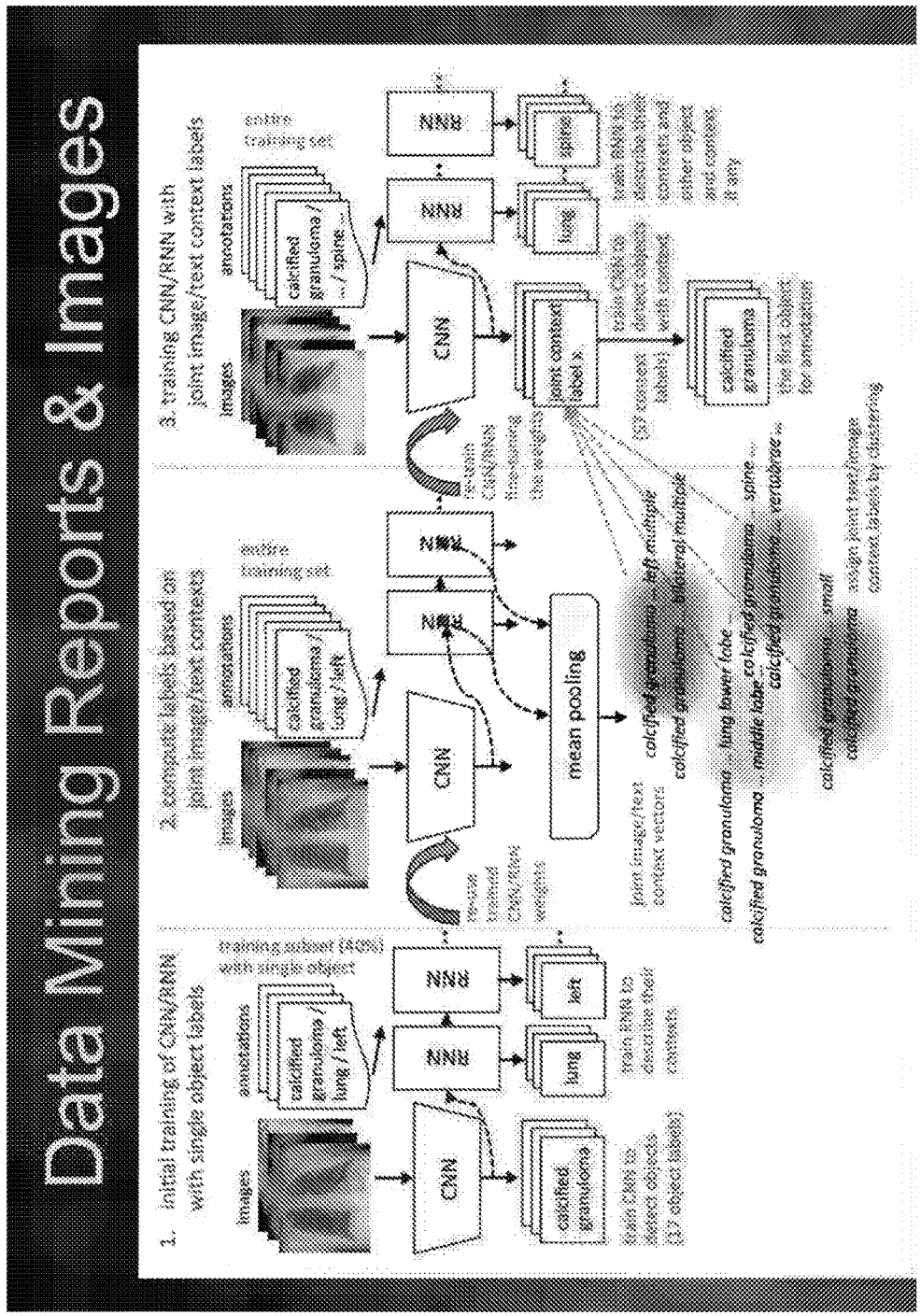
FIG. 73, depicts Data Mining, Training and Labeling with Annotated Medical Images using Convolutional and Recurrent Neural Networks with LSTM.
Figure 74:
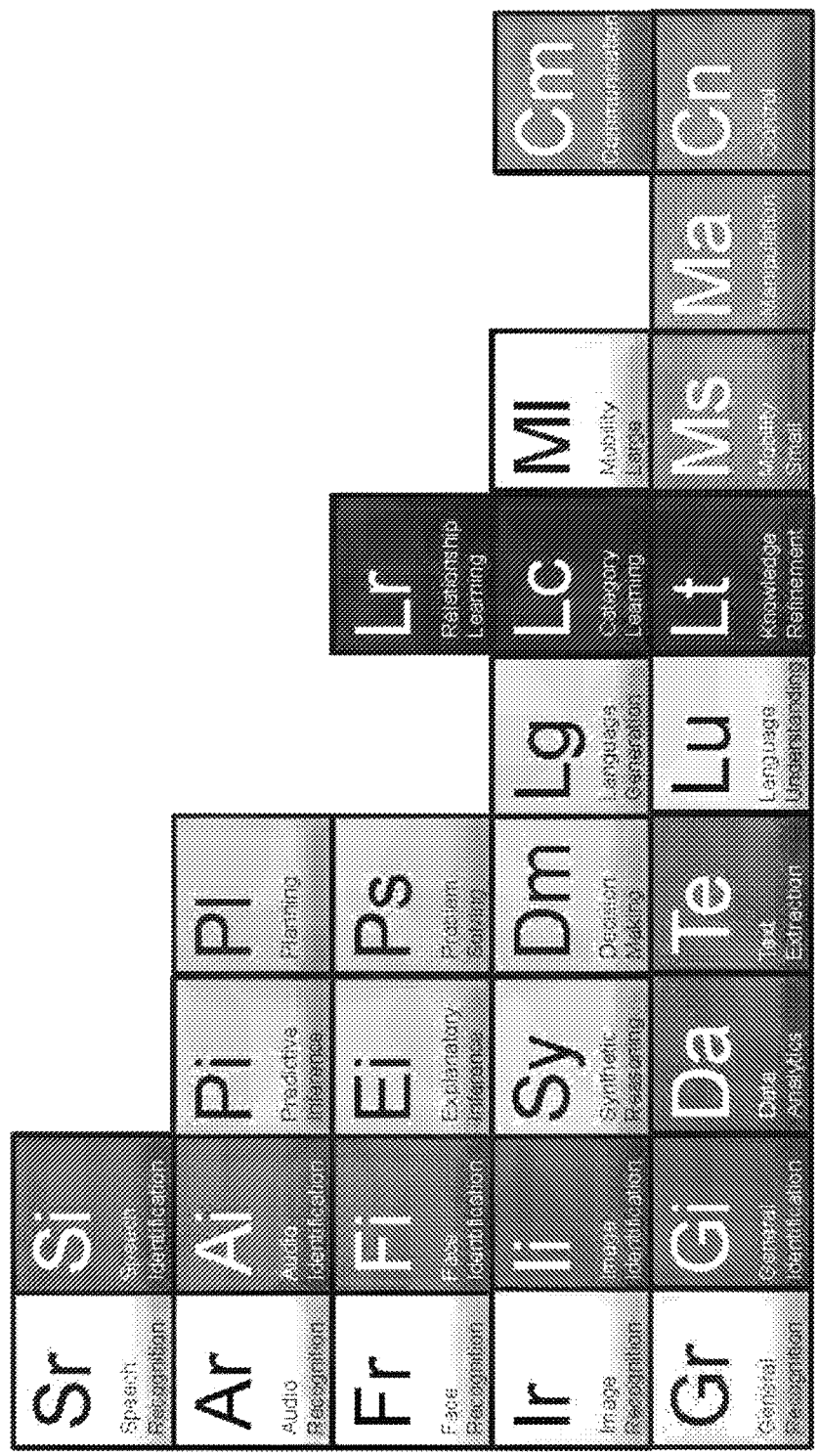
FIG. 74, depicts a Periodic Table of Artificial Intelligence with "Elementary" PAIR Techniques [Perceive-Assess-Infer-Respond].
Figure 75:
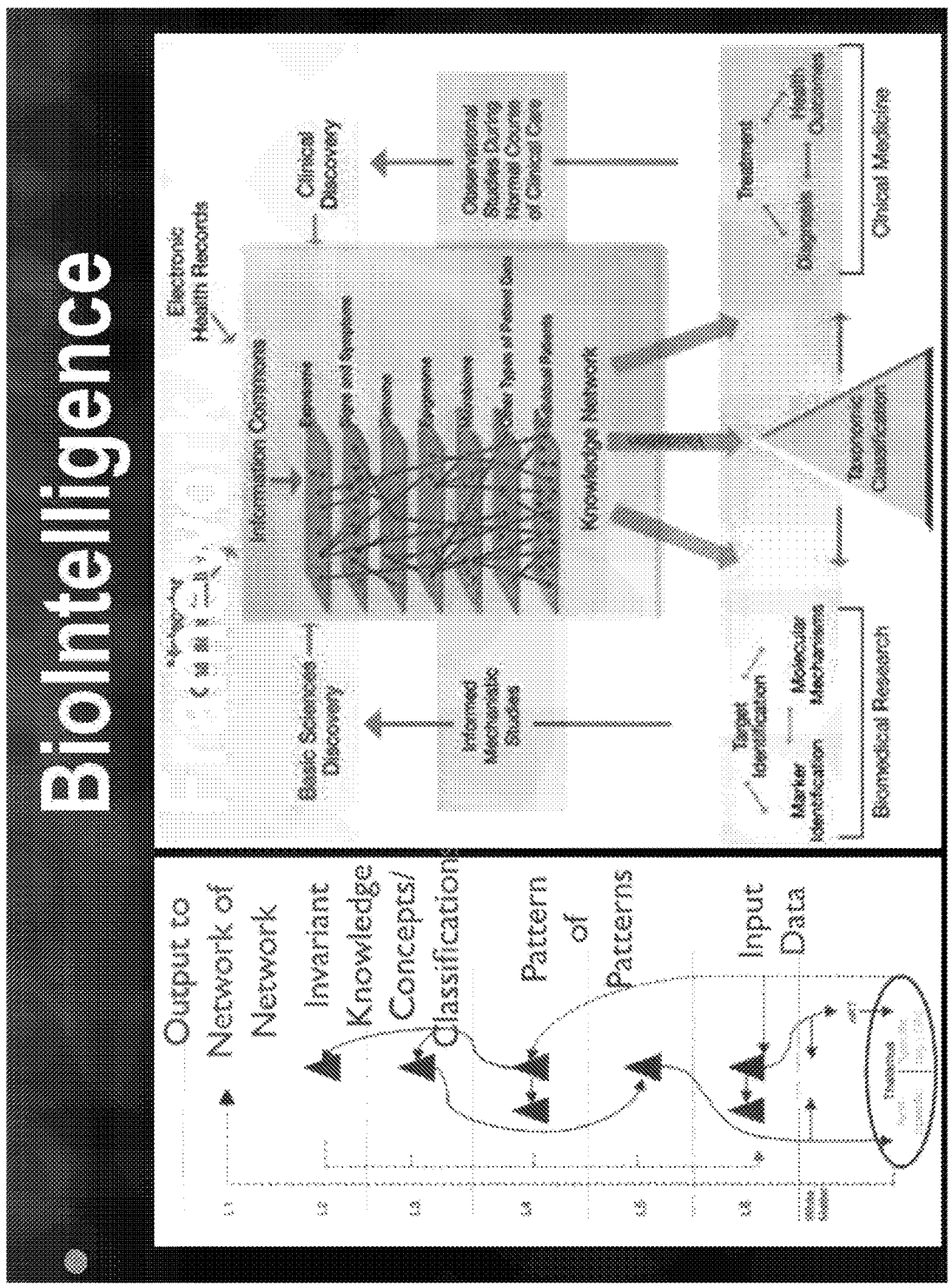
FIG. 75, depicts implementing Data-Information-Knowledge Networks with Machine Learning for BioIntelligence.
Figure 76:
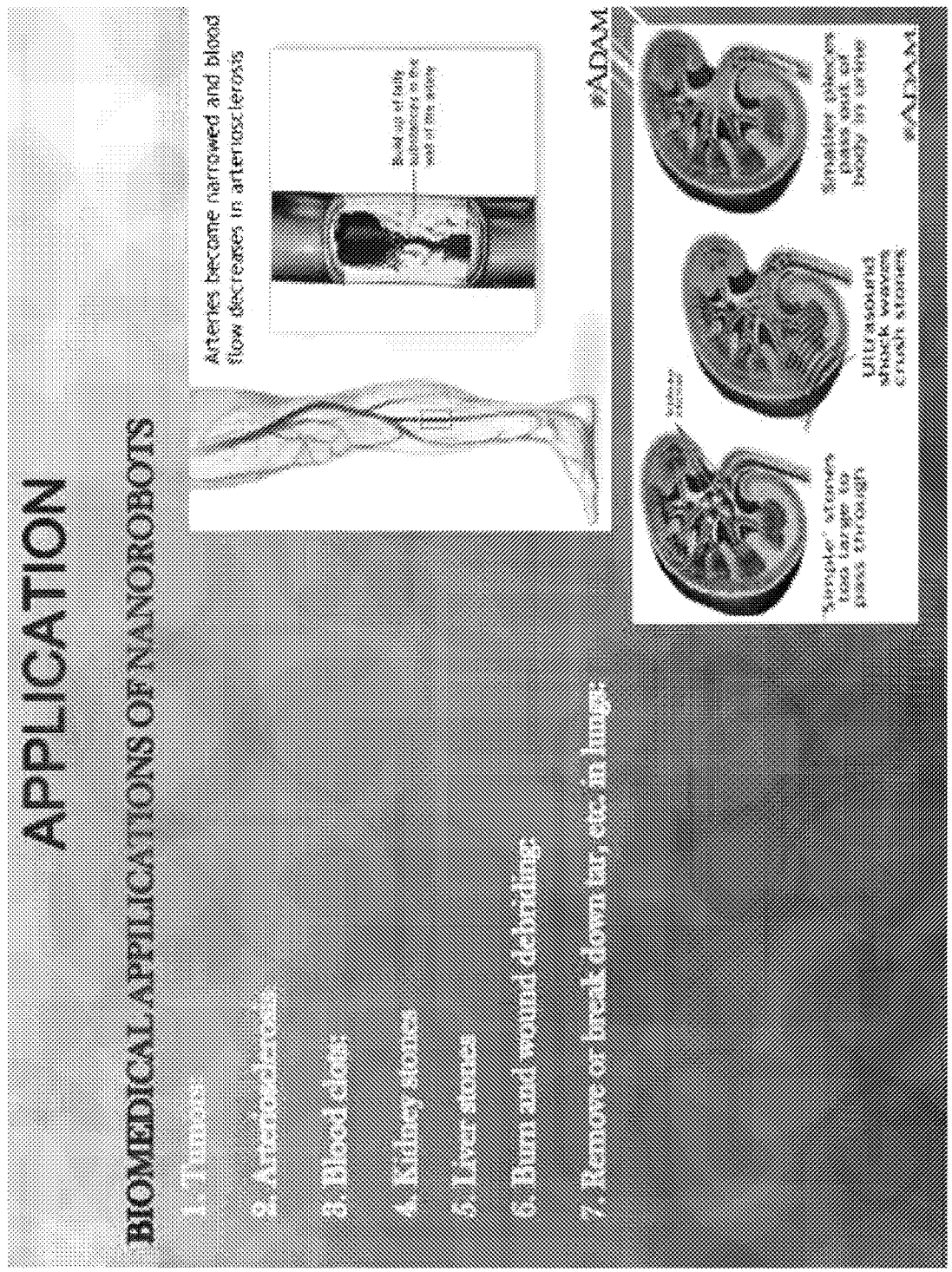
FIG. 76, depicts various biomedical applications for Nanorobotics.
Figure 77:
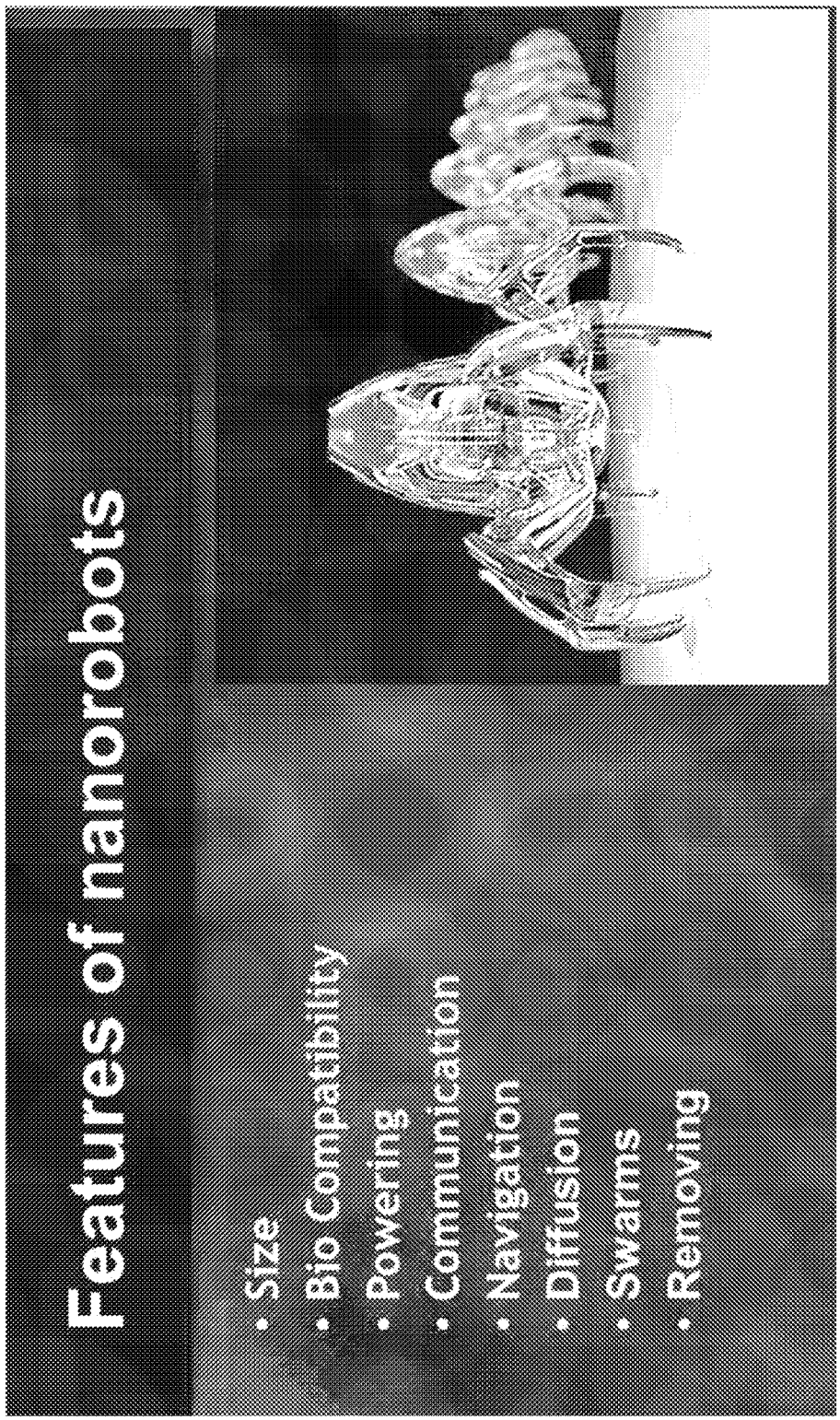
FIG. 77, depicts several typical features of Nanorobots.
Figure 78:
FIG. 78, depicts monitoring Nanorobotic agents designed to treat cancer.
Figure 79:
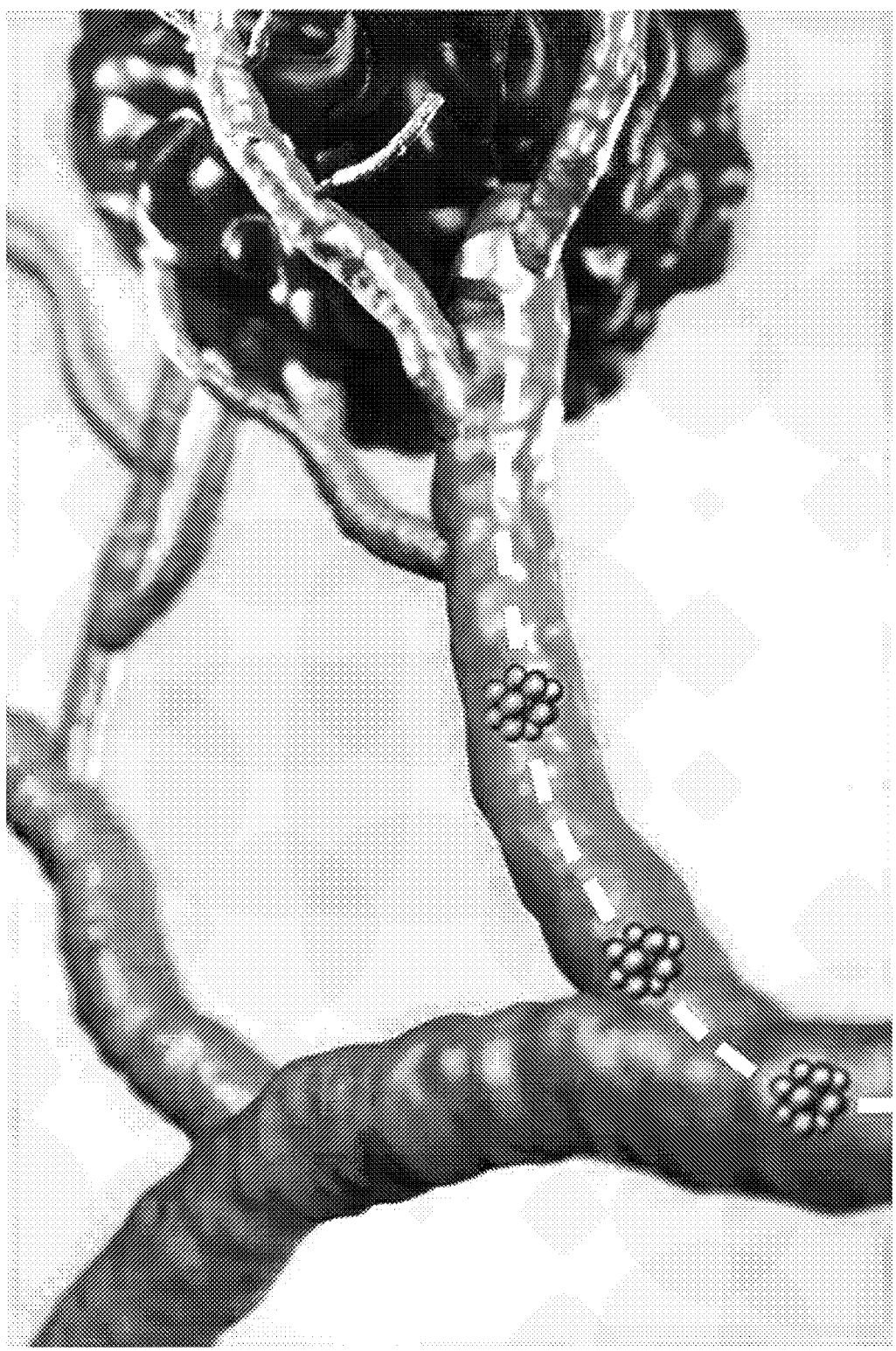
FIG. 79, depicts medical micro robots actuated by clinical MIII scanners.
Figure 80:
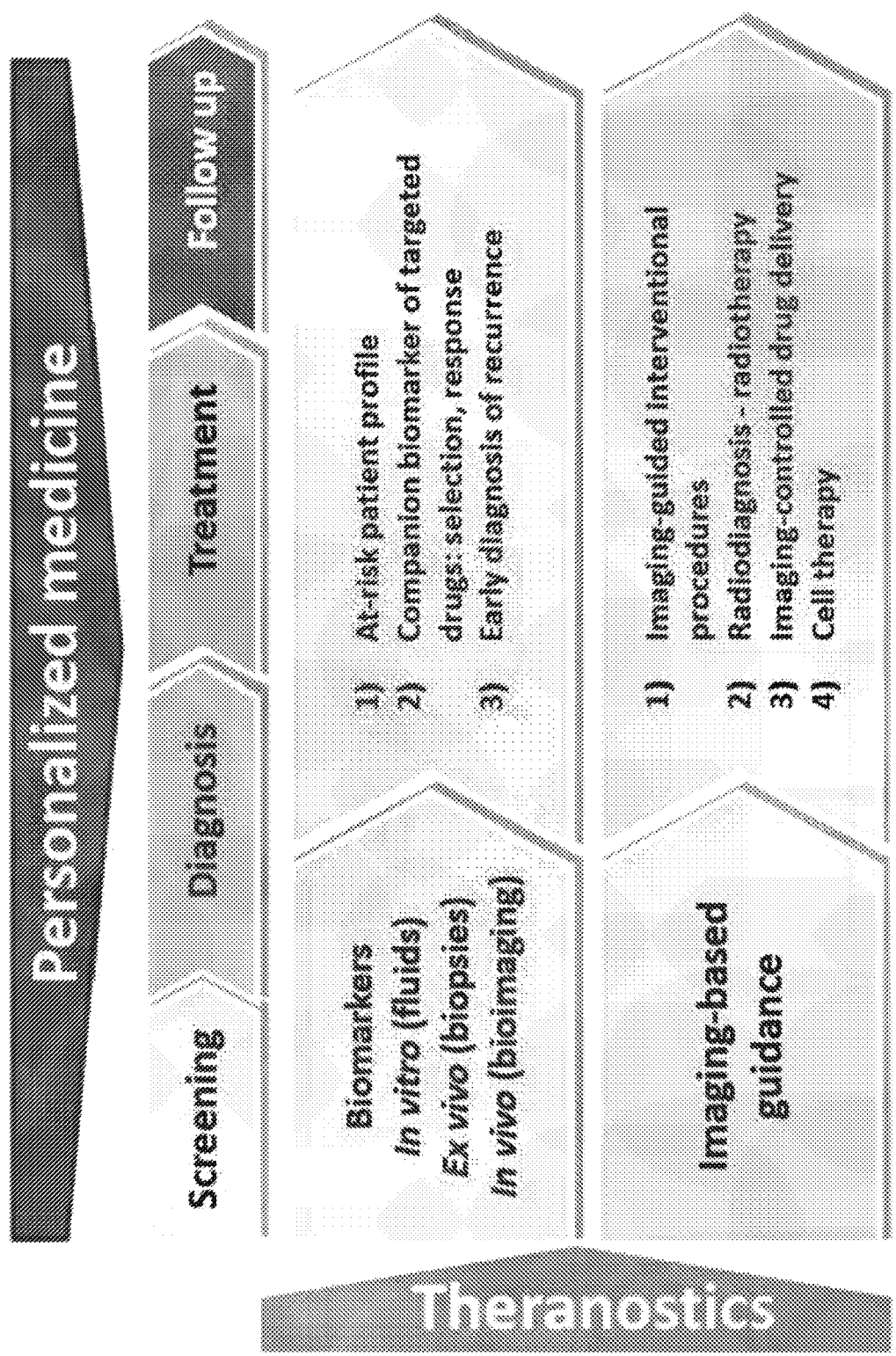
FIG. 80, depicts Personalized Precision Targeted Theranostic Nanomedicine.
Figure 81:
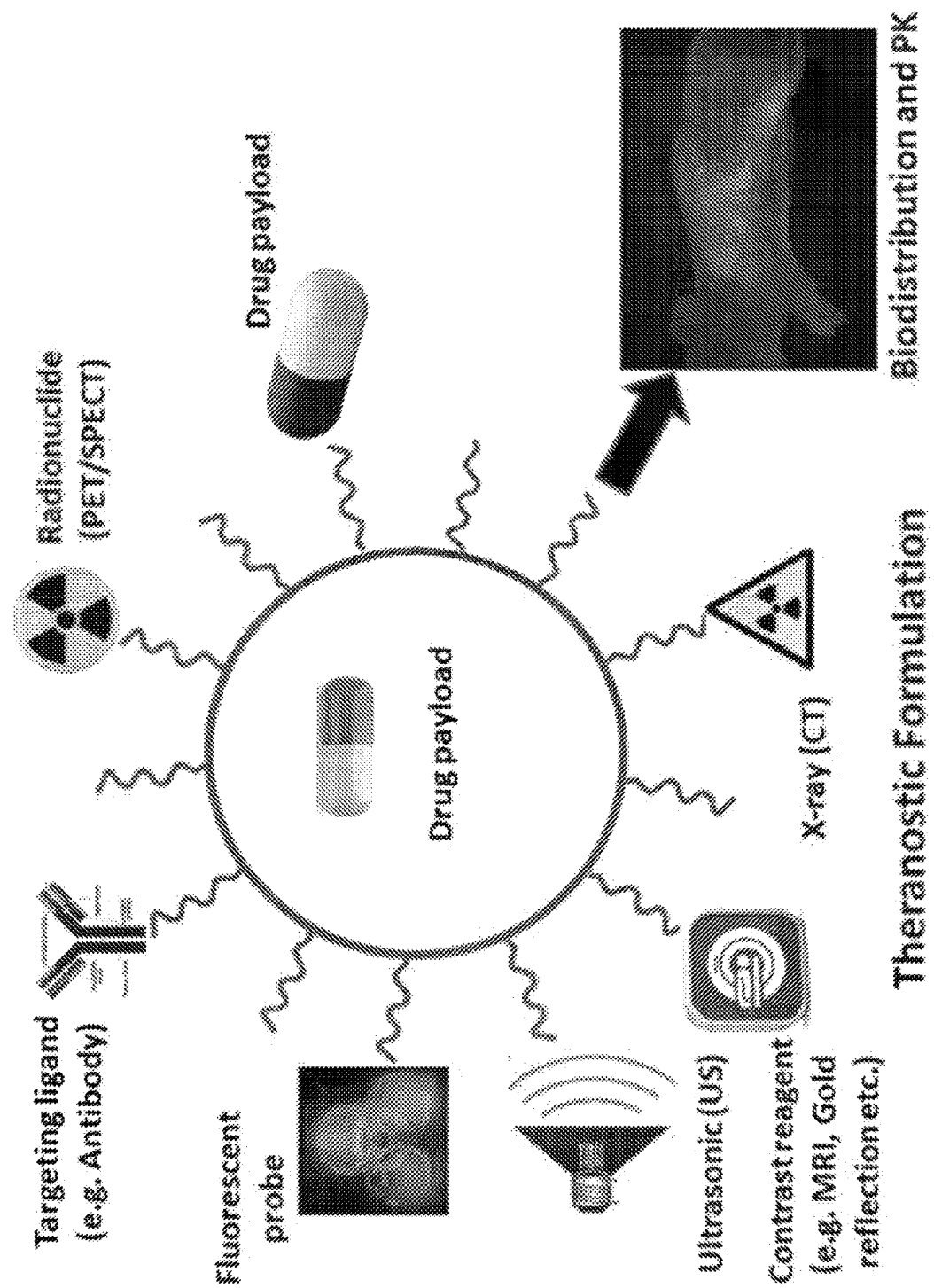
FIG. 81, depicts Imagery Guided Precision Theranostics with Targeted Drug Payloads.
Figure 82:
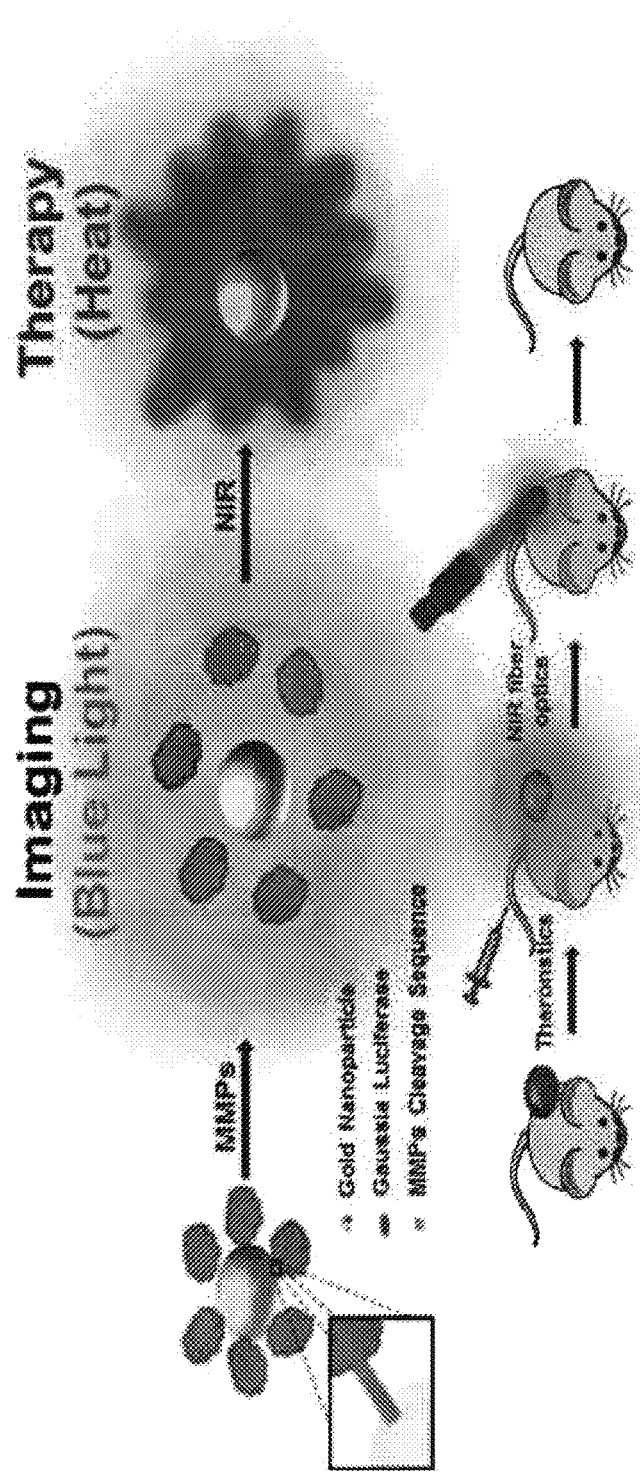
FIG. 82, depicts Nanoparticle-based Imaging Diagnostics and Therapy.
Figure 83:
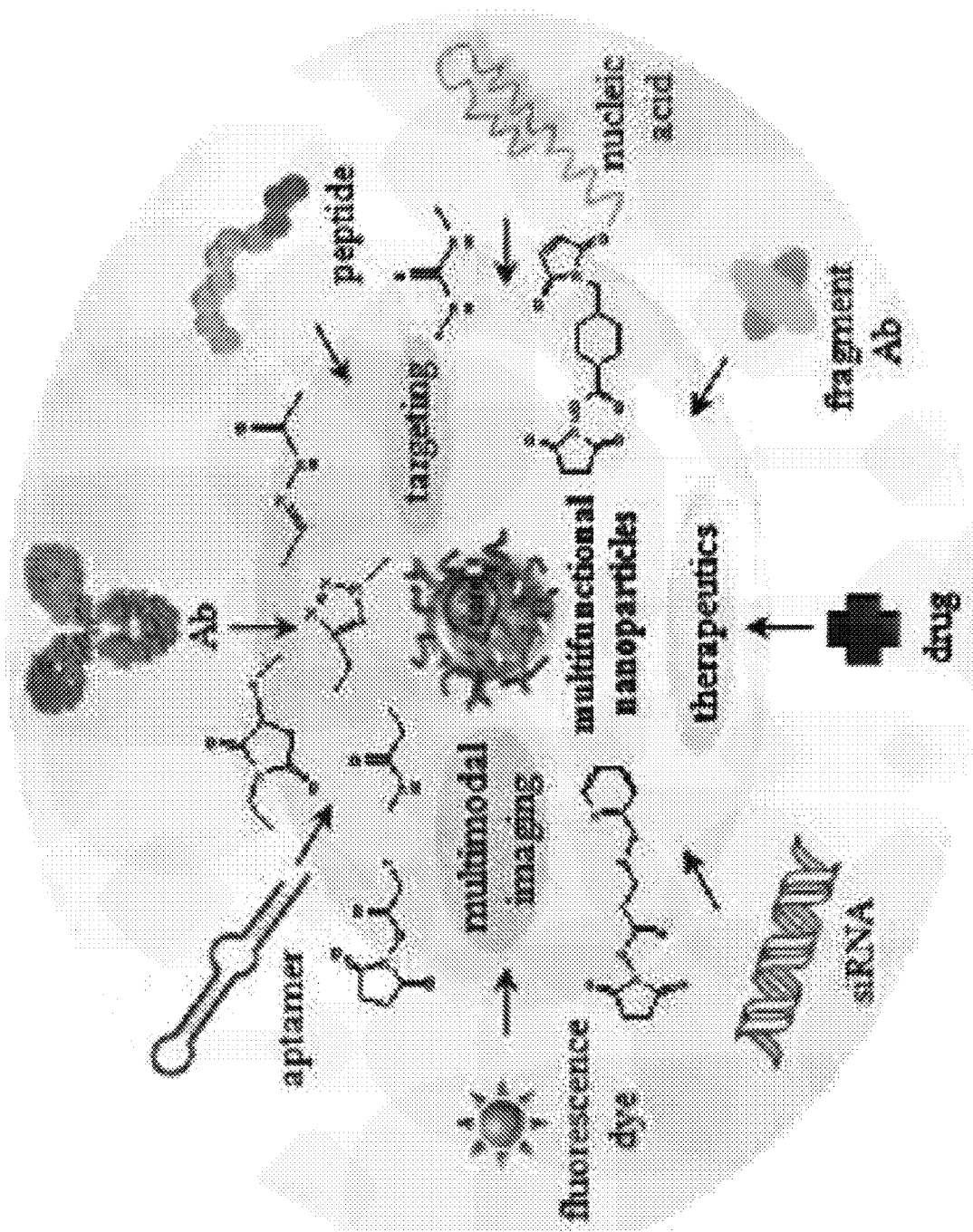
FIG. 83, depicts Multifunctional Nanoparticles for Theranostic Nanomedicine.
Figure 84:
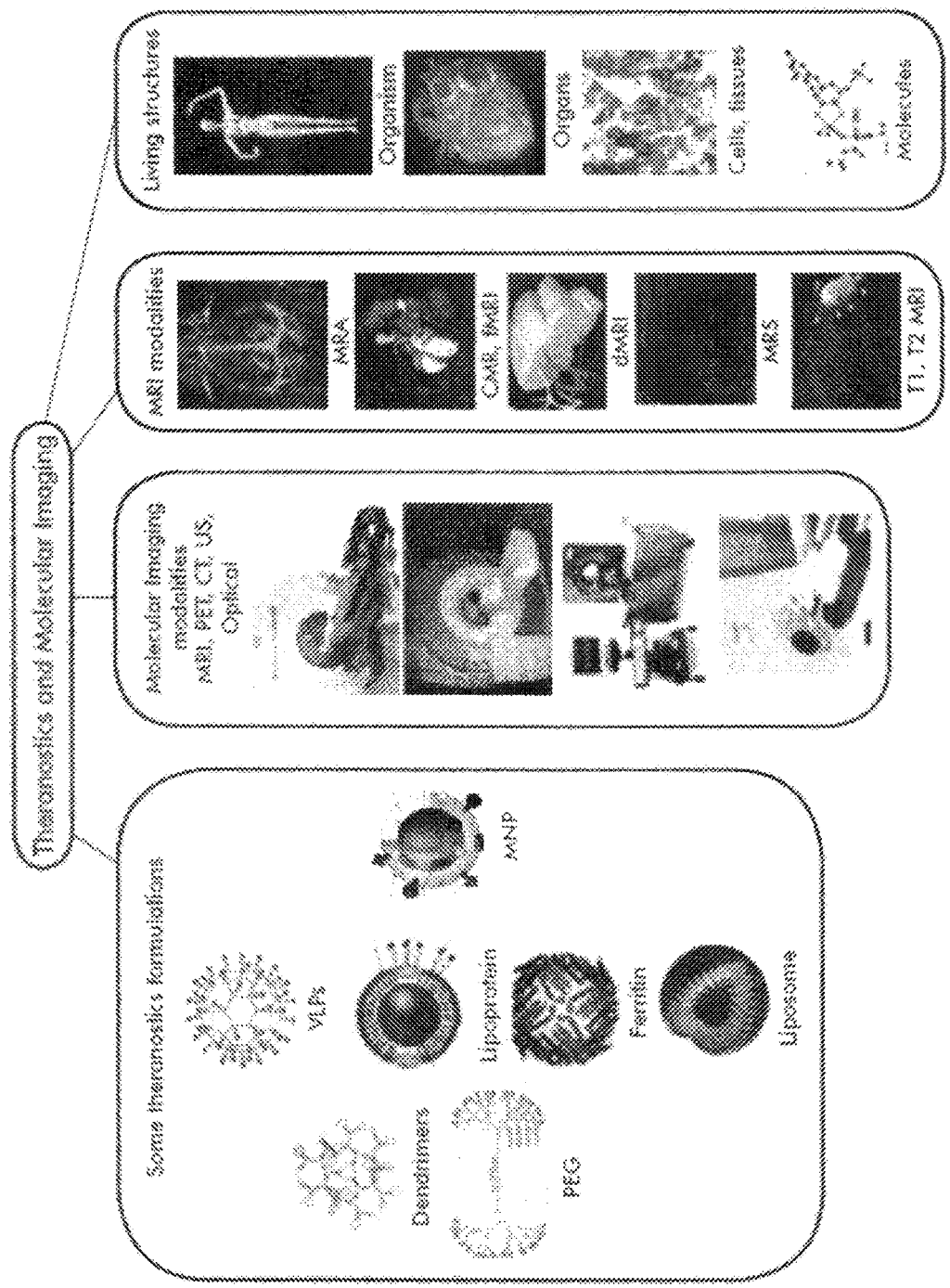
FIG. 84, depicts Integrating Theranostics Techniques with Molecular Imaging Modalities.
Figure 85:
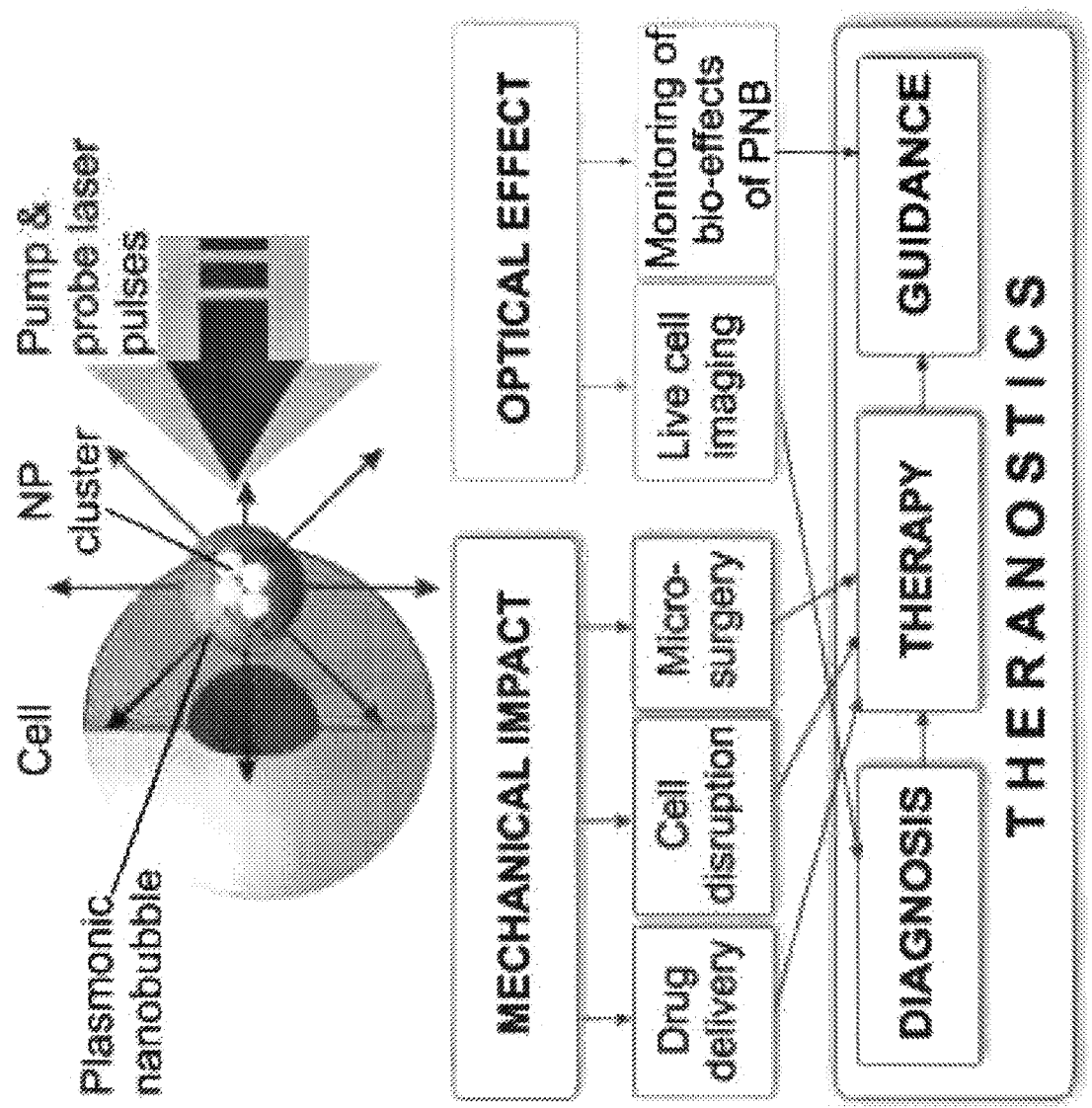
FIG. 85, depicts Drug Delivery, Cell Destruction and Micro-Surgery with in vivo Imaging Theranostics.

Various techniques for machine learning with medical imaging are specified in FIG. 63, including among others, artificial neural networks, ensemble learning and multiple instance learning. Other applications for machine learning in medicine are depicted in FIG. 74, a Periodic Table of Artificial Intelligence with "Elementary" PAIR Techniques [Perceive-Assess-Infer-Respond]. Those AI applications include speech, audio and image recognition; data analytics, inference and reasoning; text extraction, problem solving and decision making; language understanding and generation; knowledge refinement, category and relationship learning [semantics]; as well as communications, manipulation and control.

Other embodiments of the invention may include, but are not limited to, various combinations of algorithms, applications, tools and techniques for machine learning in medicine, e.g., deep learning, transfer learning, reinforcement learning, convolutional neural networks, recurrent neural networks, LSTM networks, natural language processing and augmented analytics, as well as those specified above.

The principle preferred embodiments and modes of operation of the present invention have been described in the forgoing specification. The invention which is intended to be protected herein, however, is not to be construed as limited to the particular embodiments disclosed, since these embodiments are to be regarded as illustrative rather than restrictive. Variations and changes may be made by others without departing from the spirit of this invention. Accordingly, it is expressly intended that all such variation and changes which fall within the spirit and scope of the claims be embraced thereby.

CROSS-REFERENCE TO RELATED APPLICATIONS

This application is Continuation-in-part of U.S. application Ser. No. 16/450,974 filed Jun. 24, 2019 entitled:
"Cognitive Collaboration with Neurosynaptic Imaging Networks, Augmented Medical Intelligence and Cybernetic Workflow Streams"
naming as inventor James Paul Smurro, which is incorporated herein by reference in its entirety.

This application is Continuation-in-part of U.S. application Ser. No. 15/731,201 filed May 2, 2017 entitled:
"Cognitive Collaboration with Neurosynaptic Imaging Networks, Augmented Medical Intelligence and Cybernetic Workflow Streams"
naming as inventor James Paul Smurro, which is incorporated herein by reference in its entirety.

This application is Continuation-in-part of U.S. application Ser. No. 14/544,807 filed Feb. 18, 2015 entitled:

"Multimodal Cognitive Communications and Collaborative Knowledge Exchange with Visual Neural Networking and Packetized Augmented Intelligence"
naming as inventor James Paul Smurro, which is incorporated herein by reference in its entirety.

This application Claims Priority from U.S. Provisional Application 61/967,323 filed Mar. 15, 2014 entitled:
"Network systems apparatus and method of use adapted for tele-visual communications and collaboration with streaming medical imagery and clinical informatics by networked teams of minds, machines, languages and tools, including recursively annotating, tagging, encapsulating and saving shared tele-visual communications, collaborations, imagery and informatics together as clinical cognitive vismemes in standard known file formats for interoperable delivery of personalized medicine"
naming as inventor James Paul Smurro, which is incorporated herein by reference in its entirety.

This application is Continuation-in-part of U.S. application Ser. No. 13/999,688 filed Mar. 15, 2014 entitled:
"System and method for recursive cognitive enrichment with collaborative network exchange of multimodal multistream digital communications across neurosynaptic butterfly networks"
naming as inventor James Paul Smurro, which is incorporated herein by reference in its entirety.

This application Claims Priority from U.S. Provisional Application 61/852,625 filed Mar. 15, 2013 entitled:
"Network apparatus system and method of use adapted for viewing recursively annotating and tagging, saving and retrieving, consulting and collaborating with semantically searchable clinical cognitive vismemes, together with encapsulated metadata and dicomized image-waveforms, over visual neural networks for early detection, diagnosis, prognosis, treatment, measurement and monitoring of disease, including delivery of precision personalized medicine across interconnected knowledge networks"
naming as inventor James Paul Smurro, which is incorporated herein by reference in its entirety.

This application may be related to the following commonly assigned and commonly filed U.S. patent applications, each of which is incorporated herein by reference in its entirety:
1. U.S. Pat. No. 8,924,864 B2 entitled "System and method for collaboratively communicating on images and saving those communications and images in a standard known format", naming as inventors Mariotti et al, issued Dec. 30, 2014.
2. U.S. patent application 20140176661 A1 entitled "System and method for surgical telementoring and training with virtualized telestration and haptic holograms, including metadata tagging, encapsulation and saving multi-modal streaming medical imagery together with multi-dimensional [4-d] virtual mesh and multi-sensory annotation in standard file formats used for digital imaging and communications in medicine (dicom)", naming as inventors Smurro et al, published Jun. 26, 2014.

What is claimed is:

1. A network system enabling multichannel multiplexed communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, and heterogeneous networked teams composed thereof, the network system enabling both synchronous and asynchronous multimodal clinical communications, collaboration, consultation and instruction, including recursive cognitive enrichment and collaborative knowledge exchange, with streaming imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, allowing each participant cognitive collaborant to capture, retrieve and concurrently view at least one source of streaming medical modality imagery data, and at least one or more sources of heterogeneous streaming imagery data, medical and non-medical streaming imagery data, and combinations thereof including images, video, modality imagery, audio, video and haptic wave forms and files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting clinical documents and key performance indicators, including indicators of quality of care, as well as indicators of clinical, operational and financial performance, both live and archived streaming imagery data, enabling both synchronous and asynchronous multimodal clinical communications, collaboration, consultation and instruction, as well as recursive cognitive enrichment and collaborative knowledge exchange, with streaming imagery data in collaboration sessions practiced by and among at least one or more participant cognitive collaborants during various stages of medical disease and injury management, including detection, diagnosis, prognosis, treatment, measurement, monitoring and reporting, as well as workflow optimization with operational analytics for outcomes, performance, results, resource utilization, resource consumption and costs, each participant cognitive collaborant able to view, curate, annotate and tag the heterogeneous streaming imagery data, comprising a tele-visual imagery informatics management system including,
at least one or more tele-visual imagery informatics management system clini-docks, wherein each clini-dock is adapted for independent acquisition and transmission of signals from other sources of streaming imagery data at native, enhanced or reduced resolutions and native enhanced or reduced frame rates, used for the acquisition and transmission of, live or archived streaming imagery data, including images, video, modality imagery, audio, video and haptic wave forms and files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, analog or digital video signals in standard or non-standard resolutions, medical or non-medical imagery, in compressed or uncompressed imagery formats;
at least one or more tele-visual imagery informatics management system clini-pod network servers, wherein each server is a neurosynaptic network node comprising at least one streamer, splitter, router, server and storage device enabling at least one or more participant cognitive collaborants, including persons, machines, devices, neural networks, robots and algorithms, and heterogeneous networked teams composed thereof, to concurrently view, communicate, collaborate, consult and instruct among participant cognitive collaborants, including curation, annotation and tagging, using at least one or more sources of streaming imagery data acquired and transmitted by tele-visual imagery informatics management system clini-docks, including live streaming imagery data, archived streaming imagery data, appended streaming imagery metadata, including appended semantic metadata and annotations, cognitive collaborant annotations, and archived collaborated imagery files during a synchronous or asynchronous collaboration session, establishing and maintaining channel communications for each and all of the sources of streaming imagery data for at least one or more participant cognitive collaborant during a collaboration session, enabling at least one or more participant cognitive collaborants in at least one or more locations, to concurrently view, communicate, collaborate, consult and instruct among participant cognitive collaborants using at least one or more sources of live streaming imagery data, archived streaming imagery data, appended streaming imagery metadata, cognitive collaborant annotations, and archived collaborated imagery files, including curation, annotation and tagging from each participant cognitive collaborant during a collaboration session, managing and controlling at least one or more associated databases, and privileges for authorization, authentication, identity management, security, access, publication and distribution for viewing, communicating, collaborating, consulting and instructing among participant cognitive collaborants, including managing and controlling security tokens providing access for cognitive collaborants maintained in security metadata repositories, blockchain metadata repositories and blockchain data ledgers, managing and controlling privileges for at least one or more participant cognitive collaborants to view, curate, annotate, tag, encapsulate, save, store, retrieve and distribute live streaming imagery data, archived streaming imagery data, appended streaming imagery metadata, including appended semantic metadata and annotations, cognitive collaborant annotations, and archived collaborated imagery files for each participant cognitive collaborant during collaboration sessions, enabling both synchronous and asynchronous bidirectional communications with combinations of at least one or more local area networks, at least one or more wide area networks, including internet, and at least one or more streaming imagery data repositories during at least one or more collaboration sessions, enabling identification, tracking and monitoring of participant cognitive collaborants by assignment of unique colors for annotations of streaming imagery data, archived collaborated imagery files and cognitive collaborant annotations, including telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, enabling colorized telestration, annotation and masking of colorized attention maps and colorized prediction bases for explainable artificial intelligence by participant cognitive collaborants by assignment of unique colors for annotations of streaming imagery data, archived collaborated imagery files and cognitive collaborant annotations, including telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations; and at least one or more tele-visual imagery informatics management system clini-ports allowing at least one or more participant cognitive collaborants, each, capturing live streaming imagery data, capturing associated live streaming imagery metadata, including semantic metadata and annotations, retrieving archived streaming imagery data, retrieving archived associated imagery metadata, including archived semantic metadata and annotations, and transporting live streaming imagery data, transporting associated live streaming imagery metadata, including semantic metadata and annotations, and transporting live streaming imagery data, associated live streaming metadata, including semantic metadata and annotations, archived streaming imagery data, associated archived streaming metadata, including archived semantic metadata and annotations, into collaboration sessions, concurrently viewing, communicating, collaborating, consulting and instructing among participant cognitive collaborants using at least one or more sources of streaming imagery data, curating, annotating and tagging streaming imagery data, including telestrations, drawings, illustrations, alpha-numeric text annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, and encapsulating streaming imagery data and associated streaming imagery metadata, including semantic metadata and annotations, together with cognitive collaborant annotations in native, single file format structures, and saving said streaming imagery data and said associated streaming imagery metadata, including semantic metadata and annotations, together with said cognitive collaborant annotations in at least one or more collaborated imagery files during collaboration sessions, including asynchronous or synchronous collaborations with at least one or more participant cognitive collaborants, communicating, collaborating, consulting and instructing, including viewing, curating, annotating and tagging, using at least one or more sources of streaming imagery data shared among at least one or more participant cognitive collaborants with a multi-channel stream viewer that enables capture, retrieval and concurrent viewing of both live and archived medical imagery streams together with associated metadata, including semantic metadata and annotations, during various stages of medical disease and injury management, including detection, diagnosis, prognosis, treatment, measurement, monitoring and reporting, as well as workflow optimization with operational analytics for outcomes, performance, results, resource utilization, resource consumption and costs, independently adding sources of streaming imagery data, adjust, enhance or reduce resolutions or frame rates of streaming imagery data with a multi-channel communications control interface, and independently view those additional channels of streaming imagery data and independently select which of those channels to bring into a collaboration session, conveying instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, image annotations, wave form annotations, video annotations, augmented reality imagery annotations, 3D/4D imagery annotations, haptic annotations, document annotations, outcomes annotations, performance annotations, results annotations, resource consumption annotations, resource utilization annotations and costs annotations, and not reliant upon any external communications network.

2. The network system of claim 1 for the acquisition and transmission of heterogeneous sources of streaming imagery data, enabling both synchronous and asynchronous multimodal clinical communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, and heterogeneous networked teams composed thereof, each participant cognitive collaborant able to view, curate, annotate and tag the heterogeneous streaming imagery data, including medical video, medical modality imagery, medical wave form imagery, and clinical documents during various stages of medical disease and injury management, including detection, diagnosis, prognosis, treatment, measurement, monitoring and reporting, as well as workflow optimization with operational analytics for outcomes, performance, results, resource utilization, resource consumption and costs, encapsulating and saving collaborated annotations and tags together with streaming imagery data, relevant imagery metadata, including semantic metadata and annotations, including appended imagery metadata and appended semantic metadata and annotations, from the collaboration session in native, single file format structures, known as collaborated imagery files, storing collaborated imagery files from all participant cognitive collaborants locally in media libraries or image data repositories on their respective computer storage devices, in image data repositories on televisual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieving collaborated imagery files from all participant cognitive collaborants stored locally in media libraries or image data repositories on their respective computer storage devices, in image data repositories on televisual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files.

3. The network system of claim 1 for the acquisition and transmission of medical streaming imagery data, including medical images, medical video, medical modality imagery, medical wave form imagery, clinical maps, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, the network system preserving the clinical integrity of medical streaming imagery data from medical devices, systems and equipment cleared for medical use, including clinical diagnostic purposes, care delivery and patient monitoring, enabling both synchronous and asynchronous multimodal clinical communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, and heterogeneous networked teams composed thereof, including viewing, curating, annotating and tagging streaming medical imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, including recursive cognitive enrichments thereof, for use with medical devices, equipment, systems, image and data repositories, in native, single file format structures, including those compliant with standards for digital imaging and communications in medicine.

4. The network system of claim 1 for enabling both synchronous and asynchronous multimodal clinical communications, collaboration, consultation and instruction, as well as recursive cognitive enrichment and collaborative knowledge exchange, with streaming imagery data during collaboration sessions, among participant cognitive collaborants, including persons, machines, devices, neural networks, robots and algorithms, and heterogeneous networked teams composed thereof, together with collaborated imagery files created from cognitive collaborant annotations, session metadata and medical streaming imagery data during collaboration sessions, practiced by and among at least one or more participant cognitive collaborants, including persons, machines, devices, neural networks, robots and algorithms, and heterogeneous networked teams composed thereof, including data cleared for clinical diagnostic purposes, that can be viewed, curated, annotated, tagged, encapsulated and saved together as collaborated medical imagery files and cleared for use with approved medical devices, equipment, systems, image and data repositories, in native, single file format structures, including those compliant with standards for digital imaging and communications in medicine.

5. The network system of claim 1 for archived collaborated imagery files that can be retrieved for use together with streaming imagery data during synchronous or asynchronous collaboration sessions, revised, appended, viewed, curated, annotated, tagged, encapsulated and saved in native, single file format structures, including those compliant with standards for digital imaging and communications in medicine, during collaboration sessions practiced by and among at least one or more participant cognitive collaborants, including persons, machines, devices, neural networks, robots and algorithms, and heterogeneous networked teams composed thereof, and made available for use together with streaming imagery data during current or subsequent collaboration sessions.

6. A method enabling multichannel multiplexed communications, collaboration, consultation and instruction, as well as recursive cognitive enrichment and collaborative knowledge exchange, with streaming imagery data practiced by and among at least one or more participant cognitive collaborants, including persons, machines, devices, neural networks, robots and algorithms, and heterogeneous networked teams composed thereof, the network system enabling both synchronous and asynchronous multimodal clinical communications, collaboration, consultation and instruction, as well as recursive cognitive enrichment and collaborative knowledge exchange, with streaming imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, allowing each participant cognitive collaborant to capture, retrieve and concurrently view at least one source of streaming medical modality imagery data, and at least one or more sources of heterogeneous streaming imagery data, medical and non-medical streaming imagery data, and combinations thereof including images, video, modality imagery, audio, video and haptic wave forms and files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, both live and archived streaming imagery data, enabling both synchronous and asynchronous multimodal clinical communications, collaboration, consultation and instruction, as well as recursive cognitive enrichment and collaborative knowledge exchange, with streaming imagery data in collaboration sessions practiced by and among at least one or more participant cognitive collaborants during various stages of medical disease and injury management, including detection, diagnosis, prognosis, treatment, measurement, monitoring and reporting, as well as workflow optimization with operational analytics for outcomes, performance, results, resource utilization, resource consumption and costs, each participant cognitive collaborant able to view, curate, annotate and tag the heterogeneous streaming imagery data, comprising a tele-visual imagery informatics management system consisting of the following essential components:

at least one or more tele-visual imagery informatics management system clini-docks, wherein each clini-dock is adapted for independent acquisition and transmission of signals from other sources of streaming imagery data at native, enhanced or reduced resolutions and native, enhanced or reduced frame rates, used for the acquisition and transmission of, live or archived streaming imagery data, including images, video, modality imagery, audio, video and haptic wave forms and files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, analog or digital video signals in standard or non-standard resolutions, medical or non-medical imagery, in compressed or uncompressed imagery to formats;

at least one or more tele-visual imagery informatics management system clini-pod CNS network servers, wherein each server is a neurosynaptic network node comprising at least one streamer, splitter, router, server and storage device that enables at least one or more participant cognitive collaborants, including persons, machines, devices, neural networks, robots and algorithms, and heterogeneous networked teams composed thereof, to concurrently view, communicate, collaborate, consult and instruct among participant cognitive collaborants using at least one or more sources of streaming imagery data acquired and transmitted by tele-visual imagery informatics management system clini-docks, including live streaming imagery data, archived streaming imagery data, appended streaming imagery metadata, including appended semantic metadata and annotations, cognitive collaborant annotations, and archived collaborated imagery files during a synchronous or asynchronous collaboration session,
  enables concurrent collaboration including viewing, curation, annotation and tagging with each and all of the one or more sources of streaming imagery data acquired and transmitted by tele-visual imagery informatics management system clini-docks,
  establishes and maintains channel communications for each and all of the one or more sources of streaming imagery data each participant cognitive collaborant wishes to view, monitor and collaborate with,
enables at least one or more participant cognitive collaborants to concurrently view, communicate, collaborate, consult and instruct, including curation, annotation and tagging, with live streaming imagery data, archived imagery data, appended imagery metadata, including appended semantic metadata and annotations, collaborated annotations, and archived collaborated imagery files during a synchronous or asynchronous collaboration session,
enables at least one or more participant cognitive collaborant in multiple locations, some of whom may be located remotely to the sources of streaming imagery data, to concurrently view, communicate, collaborate, consult and instruct, including curation, annotation and tagging, with live streaming imagery data, archived imagery data, appended imagery metadata, including appended semantic metadata and annotations, collaborated annotations, and archived collaborated imagery files from each participant cognitive collaborant during the collaboration session,
dynamically manages and controls with at least one or more associated databases, authorization, authentication, identity management, security, and access, publication and distribution privileges for viewing, communicating, collaborating, consulting and instructing, and cognitive collaborant privileges, including curation, annotation, tagging, encapsulation, saving, storage, retrieval and distribution of live streaming imagery data, archived imagery data, appended imagery metadata, including appended semantic metadata and annotations, collaborated annotations, and archived collaborated imagery files for each participant cognitive collaborant during collaboration sessions, including managing and controlling security tokens providing access for cognitive collaborants maintained in security metadata repositories, blockchain metadata repositories and blockchain data ledgers,
enables both synchronous and asynchronous bidirectional communications with at least one or more local area networks, at least one or more wide area networks (internet) including imagery data repositories and combinations thereof during multiple collaboration sessions,
  enables identification, tracking and monitoring of participant cognitive collaborants by assignment of unique colors for annotations of streaming imagery data, archived collaborated imagery files and cognitive collaborant annotations, that include telestrations, drawings, illustrations, alpha-numeric text annotations, as well as cognitive collaborant annotations combined with alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations,
  enables colorized telestration, annotation and masking of colorized attention maps and colorized prediction bases for explainable artificial intelligence by participant cognitive collaborants by assignment of unique colors for annotations of streaming imagery data, archived collaborated imagery files and cognitive collaborant annotations, including telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, costs annotations, resource consumption annotations and resource utilization annotations; and
at least one or more tele-visual imagery informatics management system clini-ports that allows for multiple participant cognitive collaborants, each of whom can
  capture live streaming imagery data together with associated imagery metadata, including semantic metadata and annotations, and bring into the collaboration session,
  retrieve archived streaming imagery data together with associated imagery metadata, including semantic metadata and annotations, and bring into the collaboration session,
  concurrently view, communicate, collaborate, consult and instruct with streaming imagery data,
enables curation, annotation and tagging that streaming imagery data with collaborated annotations that include telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations,
enables encapsulation and saving collaborated streaming imagery data and archived imagery metadata, including archived semantic metadata and annotations, together with appended imagery metadata, including appended semantic metadata and annotations, and collaborated annotations and from each collaboration session, including asynchronous or synchronous collaboration with at least one or more participant cognitive collaborants, in native, single file format structures, known as collaborated imagery files, enables multimodal clinical communications, collaboration, consultation and instruction, including viewing, curating, annotating and tagging, using at least one or more sources of streaming imagery data shared among at least one or more participant cognitive collaborants with a multi-channel stream viewer that enables capture, retrieval and concurrent viewing of both live and archived medical imagery streams together with associated metadata during various stages of medical disease and injury management, including detection, diagnosis, prognosis, treatment, measurement, monitoring and reporting, as well as workflow optimization with operational analytics for outcomes, performance, results, resource utilization, resource consumption and costs, enables independently adding sources of streaming imagery data, adjust, enhance or reduce resolutions or frame rates of streaming imagery data with a multi-channel communications control interface, and independently view those additional channels of streaming imagery data and independently select which of those channels to bring into a collaboration session, enables conveying instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, and not reliant upon any external communications network.

7. The method of claim 6 for the acquisition and transmission of heterogeneous sources of streaming imagery data, enabling both synchronous and asynchronous multimodal clinical communications, collaboration, consultation and instruction, as well as recursive cognitive enrichment and collaborative knowledge exchange, during collaboration sessions practiced by and among at least one or more participant cognitive collaborants, including persons, machines, devices, neural networks, robots and algorithms, and heterogeneous networked teams composed thereof, persons, each participant cognitive collaborant able to view, curate, annotate and tag the heterogeneous streaming imagery data, including medical video, medical modality imagery, medical wave form imagery, and clinical documents during various stages of medical disease and injury management, including detection, diagnosis, prognosis, treatment, measurement, monitoring and reporting, as well as workflow optimization with operational analytics for outcomes, performance, results, resource utilization, resource consumption and costs, as well as encapsulate and save collaborated annotations and tags together with the heterogeneous streaming imagery data, including medical video, medical modality imagery, medical wave form imagery, and clinical documents, and save collaborated annotations together with streaming imagery data, relevant imagery metadata, including semantic metadata and annotations, and appended imagery metadata, including appended semantic metadata and annotations, from the collaboration session in native, single file format structures, known as collaborated imagery files;

storing collaborated imagery files from all participant cognitive collaborants locally in media libraries or image data repositories on their respective computer storage devices, in image data repositories on televisual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieving collaborated imagery files from all participant cognitive collaborants stored locally in media libraries or image data repositories on their respective computer storage devices, in image data repositories on televisual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files.

8. The method of claim 6 for the acquisition and transmission of medical streaming imagery data, including medical images, medical video, medical modality imagery, medical wave form imagery, clinical maps, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, the method preserving the clinical integrity of medical streaming imagery data from medical devices systems and equipment cleared for medical use, including clinical diagnostic purposes, care delivery and patient monitoring, enabling both synchronous and asynchronous multimodal clinical communications, collaboration, consultation, instruction, as well as recursive cognitive enrichment and collaborative knowledge exchange, practiced by and among at least one or more participant cognitive collaborants, including persons, machines, devices, neural networks, robots and algorithms, and heterogeneous networked teams composed thereof, including viewing, curation, annotation and tagging of streaming medical imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, including recursive cognitive enrichments thereof, for use with medical devices, equipment, systems, image and data repositories, in native, single file format structures, including those compliant with standards for digital imaging and communications in medicine.

9. The method of claim 6 for enabling both synchronous and asynchronous multimodal clinical communications, collaboration, consultation and instruction, as well as recursive cognitive enrichment and collaborative knowledge exchange, with streaming imagery data in collaboration sessions among participant cognitive collaborants, including persons, machines, devices, neural networks, robots and algorithms, and heterogeneous networked teams composed thereof, together with collaborated imagery files created from cognitive collaborant annotations, session metadata and medical streaming imagery data during collaboration sessions, practiced by and among at least one or more participant cognitive collaborants, including persons, machines, devices, neural networks, robots and algorithms, and heterogeneous networked teams composed thereof, including data cleared for clinical diagnostic purposes, that can be viewed, curated, annotated, tagged, encapsulated and saved together as collaborated medical imagery files and cleared for use with approved medical devices, equipment, systems, image and data repositories, including those compliant with standards for digital imaging and communications in medicine.

10. The method of claim 6 for archived collaborated imagery files that can be retrieved for use together with streaming imagery data during synchronous or asynchronous collaboration sessions, revised, appended, viewed, curated, annotated, tagged, encapsulated and saved in native, single file format structures, including those compliant with standards for digital imaging and communications in medicine, during collaboration sessions, practiced by and among at least one or more participant cognitive collaborants, including persons, machines, devices, neural networks, robots and algorithms, and heterogeneous networked teams composed thereof, and made available for use together with streaming imagery data during current or subsequent collaboration sessions.

11. The method of claim 6 adapted for recursive cognitive enrichment and collaborative mind-machine knowledge exchange between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

12. The method of claim 6 adapted for informatics-enriched learning, specialist skills acquisition and accelerated knowledge exchange with multimodal clinical instruction by and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

13. The method of claim 6 adapted for cognitively-enriched enterprise imaging with streaming imagery informatics between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

14. The method of claim 6 adapted for collaborative precision medicine with multiomic data analytics between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicator of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

15. The method of claim 6 adapted for informatics-enriched imagery guided intervention, including robotic-assisted surgery, between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

16. The method of claim 6 adapted for machine learning with medical imaging, including deep learning, transfer learning, reinforcement learning, convolutional neural networks, recurrent neural networks, long short term memory networks and natural language processing, between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

17. The method of claim 6 adapted for precision guided biomedical nanorobotics between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

18. The method of claim 6 adapted for personalized precision targeted theranostic nanomedicine between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

19. The method of claim 6 adapted for managing clinical knowledge with networked metadata repositories, including semantic metatdata repositories, between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

20. The method of claim 6 adapted for cognitive engineering with networked prediction machines, including augmented mind-machine decision making and augmented analytics with network-connected edge devices, between and among participant cognitive collaborants, including persons, machines, devices, neural networks, robots and algorithms, and heterogeneous networked teams composed thereof, with neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

21. A method enabling multichannel multiplexed communications, collaboration, consultation and instruction, as well as recursive cognitive enrichment and collaborative knowledge exchange, with streaming imagery data by participant cognitive collaborants, including persons, machines, devices, neural networks, robots and algorithms, and heterogeneous networked teams composed thereof, with modular and scalable clusters of gateway streamer servers configured to support multiple network topologies, including peer-to-peer, hub-and-spoke, mesh chord and core-spine-leaf networks, as well as in 2-tier, 3-tier, or N-tier application architectures, and heterogeneous network combinations thereof, each gateway streamer server enabling neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, and combinations thereof, and together with images, video, modality imagery, waveforms, audio and haptic files, multiomic—phenotypic, genomic, metabolomic, pathomic, radiomic, radiopathomic and radiogenomic—maps and clinical data sets, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

* * * * *